US006326479B1

(12) United States Patent
Gildea et al.

(10) Patent No.: US 6,326,479 B1

(45) Date of Patent: Dec. 4, 2001

(54) SYNTHETIC POLYMERS AND METHODS, KITS OR COMPOSITIONS FOR MODULATING THE SOLUBILITY OF SAME

(75) Inventors: Brian D. Gildea, Billerica; James M. Coull, Westford, both of MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

(21) Appl. No.: 09/225,048

(22) Filed: Jan. 4, 1999

Related U.S. Application Data

(60) Provisional application No. 60/072,772, filed on Jan. 27, 1998.

(51) Int. Cl.[7] .............................. C12Q 1/68; C07H 19/00; C07H 21/00; C07H 21/02; C07H 21/04

(52) U.S. Cl. ........................... 536/23.1; 435/6; 435/91.1; 536/22.1; 536/25.3

(58) Field of Search ..................... 435/6, 91.1; 536/22.1, 536/23.1, 25.3

(56) References Cited

U.S. PATENT DOCUMENTS

| | | | |
|---|---|---|---|
| Re. 34,069 | 9/1992 | Koester | 536/27 |
| 4,415,732 | 11/1983 | Caruthers | 536/27 |
| 4,458,066 | 7/1984 | Caruthers | 536/27 |
| 4,500,707 | 2/1985 | Caruthers | 536/27 |
| 4,659,774 | 4/1987 | Webb | 525/24.2 |
| 4,725,677 | 2/1988 | Koester | 536/27 |
| 4,786,724 | 11/1988 | Letsinger | 536/27 |
| 4,923,901 | 5/1990 | Koester | 521/53 |
| 4,980,460 | 12/1990 | Molko | 536/23 |
| 5,034,506 | 7/1991 | Summerton | 528/391 |
| 5,047,524 | 9/1991 | Andrus | 536/27 |
| 5,071,974 | 12/1991 | Groody | 536/27 |
| 5,112,962 | 5/1992 | Letsinger | 536/27 |
| 5,142,047 | 8/1992 | Summerton | 544/118 |
| 5,164,491 | 11/1992 | Froehler | 536/27 |
| 5,171,679 | 12/1992 | Huber | 435/188 |
| 5,175,209 | 12/1992 | Beattie | 525/54.11 |
| 5,185,444 | 2/1993 | Summerton | 544/81 |
| 5,198,540 | 3/1993 | Koester | 536/25.3 |
| 5,204,455 | 4/1993 | Froehler | 536/22.1 |
| 5,204,456 | 4/1993 | Molko | 536/25.33 |
| 5,218,103 | 6/1993 | Caruthers | 536/25.33 |
| 5,219,764 | 6/1993 | Huber | 436/536 |
| 5,243,038 | 9/1993 | Ferrari | 536/23.1 |
| 5,262,530 | 11/1993 | Andrus | 536/25.31 |
| 5,268,306 | 12/1993 | Berger | 436/527 |

(List continued on next page.)

FOREIGN PATENT DOCUMENTS

| | | |
|---|---|---|
| 0839830A1 | 5/1998 | (EP) . |
| WO 92/20702 * | 11/1992 | (WO) . |
| WO96/04000 | 2/1996 | (WO) . |
| WO96/40709 | 12/1996 | (WO) . |
| WO98/03542 | 1/1998 | (WO) . |

OTHER PUBLICATIONS

Nielsen et al. "Strand displacement binding of a duplex-forming homopurine PNA to a homopyrimidine duplex DNA target" J. Am. Chem. Soc.118, pp. 2287–2288, 1996.*

Christensen, L. et al, Solid–phase synthesis of peptid nucleic acids. J. Peptide Science 3, 175–183 (1995).

(List continued on next page.)

*Primary Examiner*—Jezia Riley
(74) *Attorney, Agent, or Firm*—Brian D. Gildea

(57) ABSTRACT

This invention pertains to solubility enhanced polymers and methods, kits and compositions which enhance the aqueous solubility of said polymers. One set of preferred methods, kits and compositions embody or utilize phosphorous containing synthons and are most useful for modulating the solubility of synthetic nucleic acids and synthetic nucleic acid analogs. A second set of preferred methods, kits and compositions are most useful for modulating the aqueous solubility of peptides, other polyamides and most preferably peptide nucleic add (PNA) polymers.

94 Claims, 11 Drawing Sheets

$^{1}E-(O-(CK_2)_t)_g$ and $^{1}F-(O-(CL_2)_r)_s$ NH (I) + $Z^1-O-Y^1$ / $((CJ_2)_mO_n)_o$ (II) → $^{1}E-(O-(CK_2)_t)_g$, $^{1}F-(O-(CL_2)_r)_s$ $N-Z^1-((CJ_2)_mO_n)_o-Y^1-OH$ (III) —Phos-Mty→ $^{1}E-(O-(CK_2)_t)_g$, $^{1}F-(O-(CL_2)_r)_s$ $N-Z^1-((CJ_2)_mO_n)_o-Y^1-O\text{-Phos-Grp}$ (IV)

U.S. PATENT DOCUMENTS

| | | | |
|---|---|---|---|
| 5,278,302 | 1/1994 | Caruthers | 536/24.5 |
| 5,281,701 | 1/1994 | Vinayak | 536/25.34 |
| 5,348,868 | 9/1994 | Reddy | 435/91.1 |
| 5,380,833 | 1/1995 | Urdea | 536/22.1 |
| 5,391,667 | 2/1995 | Dellinger | 526/264 |
| 5,391,723 | 2/1995 | Priest | 536/23.1 |
| 5,419,966 | 5/1995 | Reed | 428/406 |
| 5,446,137 | 8/1995 | Maag | 536/23.1 |
| 5,453,496 | 9/1995 | Caruthers | 536/24.5 |
| 5,476,925 | 12/1995 | Letsinger | 536/23.1 |
| 5,480,790 | 1/1996 | Tischer | 435/188 |
| 5,527,675 | 6/1996 | Coull | 435/6 |
| 5,539,082 * | 7/1996 | Nielsen et al. | 530/300 |
| 5,623,049 | 4/1997 | Löbberding | 530/300 |
| 5,714,331 | 2/1998 | Buchardt | 435/6 |
| 5,719,262 | 2/1998 | Buchardt | 530/300 |
| 5,736,336 | 4/1998 | Buchardt | 435/6 |
| 5,773,571 | 6/1998 | Nielsen | 530/300 |
| 5,786,461 | 7/1998 | Buchardt | 536/18.7 |
| 5,955,571 | 9/1999 | Schwemler et al. | 530/300 |
| 5,985,563 | 11/1999 | Hyldig-Nielsen et al. | 435/6 |

OTHER PUBLICATIONS

Dueholm, K.L. et al, Synthesis of peptide nucleic acid monomers containing the four natural nucleobases: thymine, cytosine, adenine, and guanine and their oligomerization. J. Org. Chem. 59, 5767–5773 (1994).

Hacia, J.G. et al, Design of modified oligodeoxyribonucleotide probes to detect telomere repeat sequences in FISH assays. Nucl. Acids Res. 27, 4034–4039 (1999).

Gildea, B.D. et al, PNA Solubility Enhancers. Tet. Lett. 39, 7255–7258 (1998).

Boumrah, D. et al, Spacer molecules in peptide sequences: incorporation into analogues of atrial natriuretic factor. Tet. Lett. 32, 7735–7738 (1991).

Boumrah, D. et al, Spacer molecules in peptide sequences: incorporation into analogues of atrial natriuretic factor. Tetrahedron 53, 6977–6992 (1997).

Kynclova, E. et al, Novel method for coupling of poly(ethyleneglycol) to carboxylic acid moieties of proteins. J. Mol. Recog. 9, 664–651 (1996).

Lu, Y.–A. et al, Pegylated peptides I: solid–phase synthesis of N –pegylated peptides using Fmoc strategy. Peptide Res. 6, 140–146 (1993).

Martinez, A. et al, Branched poly(ethylene glycol) linkers. Macromol. Chem. Phys. 198, 2489–2498 (1997).

Armitage, B. et al, Hairpin–forming peptide nucleic acid oligomers. Biochem. 37, 9417–9425 (1998).

Arya, D.P. et al, Replacement of the negative phosphodiester linkages of DNA by positive S–methylthiourea linkers: a novel approach to putative antisense agents, J. Am. Chem. Soc. 120, 6619–6620 (1998).

Bergmann, F. et al, Solid phase Synthesis of directly linked PNA–DNA hybrids. Tett. Lett. 36, 6823–6826 (1995).

Cantin, M. et al, Synthesis of the monomeric building blocks of Z–olefinic PNA (Z–OPA) containing the bases adenine and thymine. Tett. Lett. 38, 4211–4214 (1997).

Ciapetti. P. et al, Synthesis of N–Fmoc– –Amino acids carrying the four DNA nuclebases in the side chain. Tetrahedron 53, 1167–76 (1997).

Corey, D.R. 48000–Fold acceleration of hybridation by chemically modified oligonucleotides. J. Am. Chem. Soc. 117, 9373–9374 (1995).

Corey, D.R. et al, Accelerated hybridization of peptide nucleic acid oligomers to targetted sequences within duplex DNA. FASEB Journal 9, A1391 (1995).

Corey, D.R. Peptide nucleic acids: expanding the scope of nucleic acid recognition. TIBTECH 15, 224–229 (1997).

de Mesmaeker, A. et al, Backbone modifications in oligonucleotides and peptide nucleic acid systems. Curr. Opin. Struc. Biol. 5, 343–355 (1995).

Diederichsen, U. Alany–PNA homoduplex: A–T pairing with the N–7–regiosomer of adenine. Bioorg. & Med. Chem. Lett. 8, 165–168 (1998).

Diederichsen, U. et al, Self–Pairing PNA with alternating alanyl/homoalanyl backbone. Tett. Lett. 37, 475–478 (1996).

Dueholm, K.L. et al, Chemistry, properties and applications of PNA. New J. Chem. 21, 19–31 (1997).

Egholm, M. et al, Peptide nucleic acids (PNA): oligonucleotide analoges with an achiral peptide backbokne. J. Am. Chem. Soc. 114, 1895–1897 (1992).

Egholm, M. et al, PNA hybridizes to complementary oligonucleotides obeying the Watson–Crick hydrogen bonding rules. Nature 365, 566–568 (1993).

Fujii, M. et al, Nucleic acid analog peptide (NAAP) 2, synthesis and properties of novel DNA analog peptides containing nucleobase linked β–aminoalanine. Bioorg. & Med. Chem. Lett. 7, 637–640 (1997).

Hyrup, B. et al, Peptide Nucleic Acids (PNA): Synthesis, properties and potential applications. Bioorg. Med. Chem. 4, 5–23 (1996).

Jordan, S. et al, New hetero–oligomeric peptide nucleic acids with improved binding properties to complementary DNA. Bioorg. & Med. Chem. Lett. 7, 687–690 (1997).

Koshkin, A.A. et al, Novel convenient syntheses of LNA [2.2.1] bicyclo nucleosides. Tett. Lett. 39, 4381–4384 (1998).

Koshkin, A.A. et al, LNA (Locked Nucleic Acids): synthesis of the adenine, cytosine, guanine, 5–methylcytosine, thymine and uracil bicyclonucleoside monomers, oligomerisation, and unprecedented nucleic acid recognition, Tetrahedron 54, 3607–3630 (1998).

Krotz, A.H. et al, Synthesis of “retro–inverse” peptide nucleic acids: 2. Oligomerization and stability. Tett. Lett. 36, 6941–6944 (1995).

Lagriffoul, P.–H. et al, the synthesis, co–oligomerization and hybridization of the thymine–thymine heterodimer containing PNA. Bioorg. & Med. Chem. Lett. 4, 1081–1082 (1994).

Lagriffoule, P. et al, Peptide nucleic acids with a conformationally contrained chiral cyclohexyl–derived backbone. Chem. Eur. J. 3, 912–919 (1997).

Lesnik, E. et al, Triplex formation between DNA and mixed purine–pyrimidine PNA analog with lysines in backbone. Nucleosides & Nucleotides 16, 1775–1779 (1997).

Lester, A. et la, PNA array technology. Presented at Biochip Technologies Conference in Annapolis (1997).

Lowe, G. et al, Amino acids bearing nucleobases for the synthesis of novel peptide nucleic acids, J. Chem. Soc., Perkin Trans. 1, 4, 539–546 (1997).

Lowe, G. et al, Dipeptides bearing nucleobases for the synthesis of novel peptide nucleic acids. J. Chem. Soc., Perkin Trans. 1, 4, 547–554 (1997).

Lowe, G. et al, Solid–phase synthesis of novel peptide nucleic acids. J. Chem. Soc., Perkin Trans. 1, 4, 555–560 (1997).

Nielsen, P.E. et al, Peptide nucleic acids (PNAs): Potential antisense and anti–gene agents. Anti–Cancer Drug Design 8, 53–63 (1993).

Orum, H. et al, Peptide Nucleic Acid, Nucleic Acid Amplification Technologies: Application to Disease Diagnostics. (ed. Lee, Morse, Olsvik) pp. 29–48 (1997).

PerSeptive Biosystems Promotional Literature: Bio ConSepts, Publication #NL612 (1996).

PerSeptive Biosystems Promotional Literature: Practical PNA, Review (1995).

PerSeptive Biosystems Promotional Literature: Practical PNA, vol. 1, Iss. 2 (1995).

PerSeptive Biosystems 1997–1998 Synthesis Products Catalog. pp. 44–46.

Petersen, K.H. et al, Synthesis and oligomerization of $N^{\delta}$Boc–N –(thymin–1–ylacetyl)ornithine. Bioorg. & Med. Chem. Lett. 6, 793–796 (1996).

Peyman, A. et al, Phosphonic ester nucleic acids (PHONAs): oligonucleotide analogues with an achiral phosphonic acid ester backbone. Angew. Chem. Int. Ed. Engl. 35, 2636–2638 (1996).

Stetsenko, D.M. et al, New approach to solid phase synthesis of polyamide nucleic acids analogues (PNA) and PNA–DNA conjugates. Tett. Lett. 37, 3571–3574 (1996).

Tomac, S. et al, Ionic effects on the stability and conformation of peptide acid complexes. J. Am. Chem. Soc. 118, 5544–5552 (1996).

Uhlmann, E. et al, Synthesis and properties of PNA/DNA chimeras. Angew. Chem. Int. Ed. Engl. 35, 2632–2635 (1996).

van der Laan, A.C. et al, An approach towards the synthesis of oligomers containing a N–2–hydroxyethyl–aminomethylphosphonate backbone: a novel PNA analogue. Tett. Lett. 37, 7857–7860 (1996).

Varma, R. Synthesis of oligonucleotide analogues with modified backbones. Synlett. 9, 621–37 (1993).

Weber, P.J.A. et al, A fast and inexpensive method for N–terminal fluorescein–labeling of peptides. Bioorg. & Med. Chem Lett. 8, 597–600 (1998).

Weiler, J. et al, Hybridization based DNA screening on peptide nucleic acid (PNA) oligomer arrays. Nucl. Acids Res. 25, 2792–2799 (1997).

* cited by examiner

I
+
V
VI

I
+
VII
VIII
Deprotect
IX

I
+
X
XI
Deprotect
XII

Fmoc-aeg-OH
1
11
12
13

HCl
Fmoc-aeg-OH
14
16
17
18

Figure 5

Comparative Synthesis: Crude Products

A

No Modification

B

C-Terminal "E"

C

C-Terminal "+"

Flu-OO-CTG-CCT-CCC-GTA-GGA-?

HPLC Purified PNA

Solution Labeling With Cy3 Of An Otherwise Insoluble PNA Oligomer

Sequence = Cy3-OE-TTA-GGG-TTA-GGG-TTA-GGG-TTA-GGG-EE-$NH_2$

HOMO G 7-MER
Injected: 49.5 OD
Recovered: 2.2 OD
Purity: > 95 %
AU
0.800
0.600
0.400
0.200
0.000
0.00
10.00
20.00
30.00
Minutes
Sequence = Flu-OEE-GGG-GGG-G-EE-NH2

Flluorescein Labeled HomoPurine PNA Oligomer
Inj. 60 OD
Rec. 3.7 OD
> 90% Pure
AU
0.0600
0.0400
0.0200
0.0000
0.00
10.00
20.00
30.00
Minutes
Sequence = Flu-OE-AGA-AGA-AGA-AGA-AGA-E-NH2

Figure 10A

UniFlu UniFlu + UniFlu E

Figure 10B

UniFlu UniFlu + UniFlu E

Sequence = Flu-OO-CTG-CCT-CCC-GTA-GGA-?

UV Tm Data
P3N
P4N
PNAD
Normalized Data
100%
90%
80%
70%
60%
50%
40%
30%
20%
10%
0%
50
60
70
80
90
100
Temp (C)

SYNTHETIC POLYMERS AND METHODS, KITS OR COMPOSITIONS FOR MODULATING THE SOLUBILITY OF SAME

CROSS REFERENCE TO RELATED APPLICATIONS

This application claims the benefit of U.S. Provisional Patent Application Serial No. 60/072,772 filed on Jan. 27, 1998.

BACKGROUND OF THE INVENTION

1. Field of the Invention

This invention is related to the field of synthetic polymers. More specifically, this invention relates to methods, kits and compositions suitable for modulating the solubility of synthetic polymers and, in particular, peptide nucleic acid (PNA) oligomers.

2. Description of the Related Art

Peptides and nucleic acids are naturally occurring compositions which are increasingly utilized in research, diagnostic and therapeutic applications. Though naturally occurring peptides and nucleic acids are generally soluble in aqueous solutions, the solubility of individual compositions of differing sequence can vary substantially, with certain compositions exhibiting little or no solubility in aqueous solution. Additionally, the introduction of products and methods for the synthetic production of peptides and nucleic acids has made available sequence variations which are not known to, or may in fact not, exist in nature. The absence of certain biopolymer sequences in nature may at least partially be due to the limited solubility of the composition.

The limited solubility of certain peptide and nucleic acid oligomers can prohibit what would otherwise be a useful research, diagnostic or therapeutic application for that polymer. Therefore, methods and compositions suitable for improving the solubility of peptides and nucleic acids in aqueous solutions may prove essential to the enablement of new technology which utilizes peptides and nucleic acids which otherwise have little intrinsic water solubility. However, compositions which modulate the solubility of synthetic polymers should preferably be simple and achiral since the effectiveness of complex macromolecules such as nucleic acids and peptides in research, diagnostic or therapeutic applications can be adversely affected by the size, complexity or chirality of attached ligands.

Peptide nucleic acids (PNAs) are non-naturally occurring polyamides (also properly characterized as pseudopeptides) which can hybridize to nucleic acids (DNA and RNA) with sequence specificity. (See: U.S. Pat. Nos. 5,539,082, 5,527,675, 5,623,049, 5,714,331, 5,736,336, 5,773,571 or 5,786,571 and Egholm et al., *Nature* 365: 566–568 (1993)). PNAs are candidates for investigation as alternatives/substitutes to nucleic acid probes in probe-based hybridization assays because they exhibit several desirable properties. In preferred embodiments, PNAs are achiral polymers which hybridize to nucleic acids to form hybrids which are more thermodynamically stable than a corresponding nucleic acid/nucleic acid complex (See: Egholm et al., *Nature* 365: 566–568 (1993)). Being non-naturally occurring molecules, they are not known to be substrates for the enzymes which are known to degrade peptides or nucleic acids. Therefore, PNAs should be stable in biological samples, as well as, have a long shelf-life. Unlike nucleic acid hybridization which is very dependent on ionic strength, the hybridization of a PNA with a nucleic acid is fairly independent of ionic strength and is favored at low ionic strength under conditions which strongly disfavor the hybridization of nucleic acid to nucleic acid (See: Egholm et. al., *Nature*, p. 567). The effect of ionic strength on the stability and conformation of PNA complexes has been extensively investigated (See: Tomac et al., *J. Am. Chem. Soc.* 118: 5544–5552 (1996)). Sequence discrimination is more efficient for PNA recognizing DNA than for DNA recognizing DNA (See: Egholm et al., *Nature*, p. 566). However, the advantages in point mutation discrimination with PNA probes, as compared with DNA probes, in a hybridization assay appears to be somewhat sequence dependent (See: Nielsen et al. *Anti-Cancer Drug Design* 8: 53–65 (1993) and Weiler et al., *Nucl. Acids Res.* 25: 2792–2799 (1997)). As an additional advantage, PNAs hybridize to nucleic acid in both a parallel and antiparallel orientation, though the antiparallel orientation is preferred (See: Egholm et al., *Nature*, p. 566).

PNAs are synthesized by adaptation of standard peptide synthesis procedures in a format which is now commercially available. (For a general review of the preparation of PNA monomers and oligomers please see: Dueholm et al., *New J. Chem.* 21: 19–31 (1997) or Hyrup et. al., *Bioorganic & Med. Chem.* 4: 5–23 (1996)). Labeled and unlabeled PNA oligomers can be purchased (See: PerSeptive Biosystems Promotional Literature: BioConcepts, Publication No. NL612, Practical PNA, *Review* and Practical PNA, Vol 1, Iss. 2) or prepared using the commercially available products.

Limited aqueous solubility and a tendency toward self-aggregation has been a long established and well documented restriction on applications of PNA (See for example: Lee, Morse & Olsvik, *Nucleic Acid Amplification Technologies: Application to Disease Diagnositics*, Chapter 3 by Ørum et al., BioTechniques Book Div. of Eaton Publishing (1997) pp. 29–48, at p. 40, lns. 14–26; Corey, D. R., *TIBTECH*, 15: 224–229, June (1997) at p. 225, col. 1, ln. 37 to col. 2, ln. 2; p. 226, col. 2, lns. 24–30 and p. 229, col. 1, lns. 14–33; Lesnik et al., *Nucleosides & Nucleotides*, 16: 177–51779 (1997) at p. 1775, lns 1–5; Peyman et al., *Angew. Chem. Int. Ed. Engl.*, 35: 2636–2638 (1996) at p. 2636, col. 1, lns. 13–24; van der Laan et al., *Tetrahedron Letters*, 37: 7857–7860 (1996) at p. 7857, lns. 1–10; Bergman et al., *Tetrahedron Letters*, 36: 6823–6826 (1995) and Egholm et al., *J. Am. Chem. Soc.*, 114: 1895–1897 (1992). The solubility properties of PNA oligomers in aqueous solution is known to be very sequence dependent. Purine-rich PNA oligomers are known to be particularly difficult to purify and/or characterize at least partially due to their limited solubility. Similarly, the solubility of PNA tends to decrease as the polymer length increases thereby resulting in a preference for shorter PNAs. Self-aggregation is another property which tends to limit the utility of PNA oligomers. Because certain PNA oligomers cannot be adequately purified or characterized, there are presently a large number of potentially useful PNA sequence variations which are unavailable for evaluation in research, diagnostic or therapeutic applications.

By way of example, the product literature of a commercial vendor of custom PNA oligomers states "For most applications an oligomer of 12–15 is optimal. Longer PNA oligomers, depending on the sequence, tend to aggregate and are difficult to purify and characterize" (See: Guidelines For Sequence Design of PNA Oligomers: PerSeptive Biosystems, Inc. Promotional Literature; 1997–1998 Synthesis Products Catalog, col. 2, lns. 6–11, p. 45). Additionally, this document sets forth several rules for the design of a PNA oligomer which will avoid these limitations. Under the heading "Specific Design Rules" (col. 3, lns. 1–18), the text reads "Length: We will not synthesize any sequences with more than 18 bases, not including linkers, amino acids and labels. Purine Content: Purine rich PNA oligomers tend to aggregate and have low solubility. To avoid that follow these specific guidelines: 1. Of any stretch of 10 bases in the sequence do not have more than 6 purines 2. NO more than 4–5 purines in a row, specifically no more than 3 G's in a row". The vendor suggests that one consider analyzing the other strand if it is otherwise impossible to comply with the limitations set forth in guidelines 1 and 2.

A number of modifications have been made to peptide nucleic acids (PNAs) in order to improve their aqueous solubility or minimize polymer self-aggregation. A commonly used modification of PNA which was first used by the inventors involves the incorporation of one or more positively charged terminal lysine residues (See: Egholm et al., *J. Am. Chem. Soc.*, 114: 1895–1897 (1992) at p. 1896, col. 1, ln. 23 to col. 2, ln. 2). The inventors of PNA, as well as others, have also advocated the preparation of PNAs having backbone modifications which comprise one or more alkyl amine groups (See: U.S. Pat. No. 5,719,262 and Lesnik et al., *Nucleosides & Nucleotides*, 16: 1775–1779 (1997)). Though these modifications improve aqueous solubility, they also introduce chiral atoms to which are linked moieties having nucleophilic primary amine groups which are positively charged at physiological pH. The introduction of chiral centers into PNA can alter the hybridization properties of the polymer (See: Lee, Morse & Olsvik, *Nucleic Acid Amplification Technologies: Application to Disease Diagnositics*, Chapter 3 by Ørum et al., BioTechniques Book Div. of Eaton Publishing (1997) pp. 29–48, at p. 33, ln. 4, to p. 34, ln. 12). Additionally, nucleophilic moieties and particularly primary and secondary amino groups must be protected during synthesis and their presence can complicate synthesis, labeling and/or purification. Though positively charged PNAs may exhibit improved hybridization kinetics (See: Corey et al., *J. Am. Chem. Soc.*, 117: 9373–9374 (1995) and Corey et al., FASEB Journal, 9, A1391 (1995)), positively charged groups may also result in non-nucleobase specific interactions which may lead to increased background in a hybridization-based assays.

Another approach to overcoming the limited solubility and self-aggregation of PNA has been to modify the backbone to incorporate negatively charged phosphate moieties (See: Peyman et al., *Angew. Chem. Int. Ed. Engl.*, 35: 2636–2638 (1996) and van der Laan et al., *Tetrahedron Letters*, 37: 7857–7860 (1996)). However, one of the most advantageous properties of PNA is the neutral backbone which allows for nucleic acid hybridization which is fairly independent of ionic strength and is favored at low ionic strength under conditions which strongly disfavor the hybridization of nucleic acid to nucleic acid. Backbone modifications which re-introduce a negative charge will likely negate this advantageous property.

Still another approach to overcoming the limited solubility and self-aggregation of PNA has been to prepare PNA-DNA chimeras wherein the negative charge on the DNA part of the chimera reduces the tendency toward self-aggregation and thus improves solubility (See: Uhlmann et al., *Angew. Chem. Ed. Engl.*, 35: 2632–2635 (1996) at p. 2632, col. 2, lns. 33–35). However, PNA-DNA chimeras are segmented molecules which exhibit hybrid properties. For example, the Tm of chimeras examined by Uhlmann et al. were approximately half way between the Tm of the DNA/DNA hybrid and the PNA/DNA hybrid (See: Uhlmann et al., *Angew. Chem. Ed. Engl.*, 35: 2632–2635 (1996) at FIG. 4).

Though not expressly designed or sold to improve PNA solubility, applicants have noted that a commonly used ether-based, achiral hydrophilic straight chain linker (8-amino-3,6-dioxaoctanoic acid) can be used to minimally improve the aqueous solubility of PNA oligomers and particularly PNAs labeled with hydrophobic moieties such as fluorescein and rhodamine dyes. However, the 8-amino-3,6-dioxaoctanoic acid linker moiety is not branched, does not maintain the proper spacing for nucleobase to nucleobase interactions, does not branch from the backbone (typically made part of the backbone) and furthermore, conveys only a very limited improvement in aqueous solubility to the PNA oligomer.

Because the utility of a particular PNA oligomer in a research, diagnostic or therapeutic application will generally be specifically related to its sequence, the above mentioned limitations on sequence diversity may prove to be an Achilles Heel of this newly developed and very promising technology. Therefore, it would be useful to provide methods, kits and compositions suitable for improving the aqueous solubility of PNA oligomers and/or reducing their tendency toward self-aggregation so that a greater number of pure PNA oligomers are available for use in research, diagnostic and therapeutic applications. The preferred methods, kits and compositions will exhibit little or no adverse effects on the hybridization properties or physical characteristics of the PNA oligomer. Thus, the most preferred solubility enhancing modifying moieties will be achiral, non-nucleophilic and uncharged at physiological pH or achiral, non-nucleophilic and positively charged at physiological pH.

Any methods, kits and compositions which enhance the solubility of PNA oligomers, should also be equally useful in improving the solubility of peptides or polyamide and/or reducing or eliminating self-aggregation of the polymer. With certain variations, similar compositions should find utility for the modification of nucleic acids and nucleic acid analogs.

SUMMARY OF THE INVENTION

As previously discussed, the limited solubility of PNA oligomers, and particularly purine-rich oligomers, is well documented in the chemical literature. Though not exclusively a problem associated with purine-rich sequences, it has been observed that the solubility/self-aggregation properties of PNA oligomers are a sequence specific phenomenon which tends to be particularly problematic when preparing purine-rich, and particularly G-rich PNAs. Given these limitations which were encountered when attempting to synthesize, purify and characterize certain desired PNA oligomers, applicants were compelled to invent a means to overcome the limitations of the prior art to thereby obtain the purified PNAs of desired nucleobase sequence which they required. Guided by the discussion contained herein it will become apparent to those of skill in the art that the compositions developed by applicants, or modifications thereof, will find utility in improving the solubility of synthetic polymers such as peptides, other polyamides, nucleic acids, nucleic acid analogs and particularly the nucleic acid analogs which comprise a neutral backbone.

In one embodiment, this invention pertains to branched or multiply branched compositions useful for improving the solubility of synthetic polymers and/or which minimize or eliminate polymer self-aggregation. These branched or multiply branched solubility enhancing compositions may, depending of the nature of the starting materials, generate soluble polymers having modifying moieties which are positively charged or uncharged (at physiological pH), nucleophilic or non-nucleophilic and chiral or achiral, though they are preferably achiral. A preferred combination of the aforementioned variables is a branched or multiply branched modifying moiety which is uncharged, non-nucleophilic and achiral. Another preferred combination of the aforementioned variables is a branched or multiply branched modifying moiety which is positively charged, non-nucleophilic and achiral. Certain compositions of this invention are particularly well suited for modifying synthetic nucleic acids and its synthetic analogs while other compositions are better suited for the modification of peptides, PNAs and other polyamides.

For the modification of synthetic nucleic acids and its analogs, this invention provides several branched or multiply branched compositions or polymer synthons which are suitable for use in standard nucleic acid assembly methodologies. Preferred compositions shall be phosphoramidite derivatives and preferably, β-cyanoethylphosphoramidites. One very useful β-cyanoethylphosphoramidite is a multiply branched synthon having the formula:

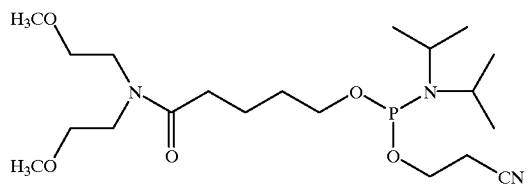

Because they enhance the solubility of nucleic acids, these compositions are particularly well suited for improving the solubility of nucleic acid analogs in which the sugar phosphate backbone has been modified so that the analog backbone is uncharged.

In another embodiment, this invention also relates to synthetic nucleic acid and nucleic acid analogs which are modified with simple, branched or multiply branched compositions to thereby improve polymer solubility and/or minimize or eliminate polymer self-aggregation.

For the modification of polyamides, peptide and PNAs, this invention provides several branched or multiply branched compositions or polymer synthons which are particularly well suited for incorporation during chemical assembly. When used to prepare modified PNA oligomers, applicants have observed unprecedented improvement in solubility and reduction in polymer self-aggregation. Consequently, for the first time known by applicants, it is possible to isolate purified PNA oligomers which do not adhere to the synthesis and sequence limitations well known in the art. Furthermore, using dot blot and Fluorescent In Situ Hybridization (PNA-FISH) formats (See for example: FIGS. 10A and 10B), applicants have demonstrated that PNAs which are modified with the preferred compositions of this invention exhibit hybridization properties which are not detectably different from the unmodified PNA oligomers. Thermal melting experiments have further confirmed that the preferred solubility enhancing moieties of this invention do not appreciably affect the Tm of polymer hybrids (See: Example 17). Interestingly however, further experimentation has demonstrated that the presence of the solubility enhancers can improve upon the cooperativity of the melting and reannealing transition without significantly affecting Tm (See: Example 18). In addition to the observed improvements in purity and ease of characterization, applicants have additionally observed improvements in polymer recovery when utilizing conventional chromatographic procedures for purification (See: Example 19). Taken as a whole, the data demonstrates that the PNAs which are modified with preferred modifying moieties exhibit no adverse affects on hybridization properties as compared with the unmodified polymers but are significantly more soluble in aqueous solution.

For the modification of peptides, polyamides and PNAs, suitably protected amino acids are typically used as the branched or multiply branched polymer synthons. One particularly useful synthon suitable for the modification of peptides, polyamides and PNAs, abbreviated herein as Fmoc-"E"aeg-OH, is the achiral, multiply branched, non-nucleophilic ether (compound 13) having the formula illustrated in FIG. 3A. Upon polymer modification, the modifying moiety is an ether moiety (herein referred to as "E") which is achiral, multiply branched, uncharged and non-nucleophilic.

Another particularly useful synthon suitable for modifying peptides, polyamides and PNAs, abbreviated herein as Fmoc-"+"aeg-OH, is the achiral, multiply branched, non-nucleophilic zwitterion (compound 18) having the formula illustrated in FIG. 3B. Upon polymer modification, the modifying moiety is an ether moiety (herein referred to as "+") which is achiral, multiply branched, non-nucleophilic and positively charged at physiological pH.

In another embodiment, this invention pertains to methods for improving the solubility of synthetic polymers such as nucleic acids, nucleic acid analogs, peptide polyamides and particularly PNA oligomers. The method comprises reacting the polymer, a monomeric subunit of a polymer or a synthesis support upon which a synthetic polymer is to be assembled, with one or more branched or multiply branched compositions or synthons useful for improving the solubility of synthetic polymers and/or which can minimize or eliminate polymer self-aggregation. Non-limiting examples of branched and multiply branched compositions suitable for the practice of the methods of this invention are described herein.

In still another embodiment, this invention relates to synthetic nucleic acids, nucleic acid analogs, polyamides, peptides, and particularly PNA oligomers, which have been modified with the compositions or methods described herein. Preferably, the synthetic polymers have been modified with simple branched or simple multiply branched compositions described herein.

In one preferred embodiment, the modified polymer comprises one or more achiral, multiply branched, non-nucleophilic, uncharged (neutral) ether modifying moieties (herein identified as "E") having the formula:

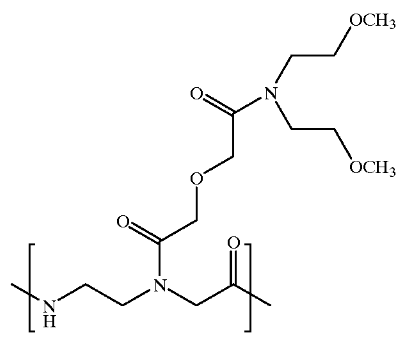

In another preferred embodiment, the polymers of this invention comprise one or more achiral, multiply branched, non-nucleophilic, positively charged (at physiological pH)

ether modifying moieties (herein identified as "+") having the formula:

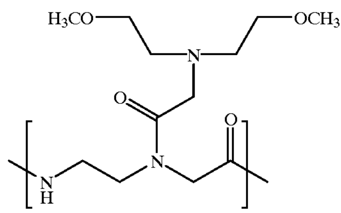

The modified polymers of this invention may exist immobilized to supports including polymer arrays (e.g. the polymer may exist on the support on which it is assembled or may have been removed from the synthesis support, deprotected, purified, and re-immobilized to another support), as lyophilized powders or be dissolved or suspended in aqueous solution.

Moreover, this invention specifically relates to modified PNA oligomers and more preferably those modified PNA oligomers having a purine nucleobase content of 75% or greater in a PNA oligomer having 8 or more nucleobases. Likewise, this invention also relates to purified, unlabeled or labeled, modified PNA oligomers having four or more sequential G residues (nucleobases) in a PNA oligomer having 6 or more nucleobases. This invention additionally relates to purified, labeled or unlabeled, modified PNA oligomers having 6 or more sequential purine residues. As an extreme example of a purine-rich PNA oligomer, this invention relates to purified, labeled or unlabeled, homopurine modified PNA oligomers comprising 6 or more nucleobases.

In still another embodiment, the compositions of this invention may also be offered in a kit or the methods used in combination with a kit. Preferred kits of this invention will comprise branched or multiply branched synthons so that one of ordinary skill in the art may easily utilize them during chemical assembly to thereby modify a synthetic polymer. Other preferred kits of this invention will comprise polymers which have been modified with one or more branched or multiply branched modifying moieties to thereby improve aqueous solubility of the polymer and/or decrease or eliminate polymer self-aggregation. Preferably, the kits comprise simple branched or simple multiply branched compositions described herein.

The kit-based compositions of this invention shall preferably be suitable for direct use in the chemical assembly of the polymer whether or not an automated instrument is utilized. Preferred kits of this invention will comprise Fmoc-"E"aeg-OH and/or Fmoc-"+"aeg-OH. Alternatively, the kit shall comprise a synthesis support to which a composition (e.g. Fmoc-"E"aeg-OH and/or Fmoc-"+"aeg-OH) or polymer comprising a modifying moiety has been covalently linked.

Consequently, when using the compositions, kits and/or methods described herein, it is now possible to routinely purify and characterize both labeled and unlabeled PNA oligomers having a purine content of 75% or greater. Additionally, it is now possible to routinely purify and characterize both labeled and unlabeled PNA oligomers having four or more sequential G residues. Furthermore, it is now possible to routinely purify and characterize labeled and unlabeled PNA oligomers having 6 or more sequential purine residues, including homopurine PNAs of at least 15 residues in length.

Guided by the teachings set forth herein, those of ordinary skill in the art will appreciate that the possession and/or practice of the embodiments of this invention will afford important features and advantages not presently known but which shall improve the state of the art. Several noteworthy features and advantages are summarized as follows:

Unique Features and Advantages of the Methods, Kits and Compositions of this Invention 1. Improved aqueous solubility of polymers and particularly peptide nucleic acid polymers.
2. Minimize or eliminate polymer self-aggregation of polymers and particularly peptide nucleic acid polymers.
3. Facilitate synthesis, purification and analysis of many insoluble polymers and particularly purine-rich PNA polymers labeled with hydrophobic labels.
4. Produces little or no modification of the Tm of a hybrid between a modified PNA oligomer and a nucleic acid as compared with the hybrid formed with the unmodified PNA and a nucleic acid.
5. May improve the cooperativity of the melting and reannealing transitions of a hybrid formed from a modified PNA oligomer and a polymer or polymer segment comprising a complementary nucleobase sequence as compared with a hybrid wherein the PNA oligomer is unmodified.
6. Preferred PNA solubility enhancing compositions are achiral ethers and/or alcohols which comprise positively charged tertiary amines or uncharged moieties wherein the modifying moiety branches from the polymer backbone (e.g. a side chain).
7. Preferred PNA solubility enhancing compositions maintain subunit to subunit spacing which has been demonstrated to be the most favorable spacing so that the PNA exhibits optimal hybridization properties (i.e. comprise an N-[2-(aminoethyl)]glycine backbone).

BRIEF DESCRIPTION OF THE DRAWINGS

FIGS. 5A–5C are HPLC chromatograms of a crude unmodified PNA oligomer and two modified PNA oligomers having either a C-terminal "E" or "+" moiety.

FIGS. 10A I–III are electronic images of membranes upon which dot blot assays were performed to compare the function of PNA oligomers which were unmodified or C-terminally modified with either of "E" or "+".

FIGS. 10B I–III are electronic images of photographs of PNA-FISH assays with *E. Coli* which were used to compare the function of PNA oligomers which were unmodified or C-terminally modified with either of "E" or "+".

DESCRIPTION OF THE PREFERRED EMBODIMENTS

Figure 1A:
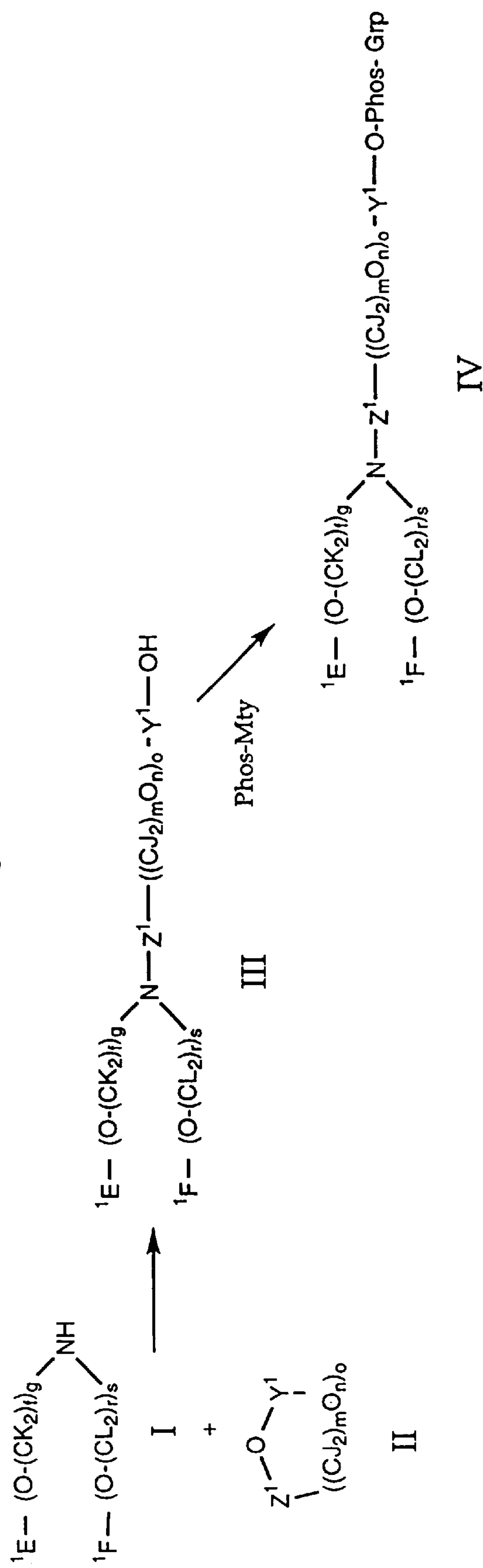
FIG. 1A is a general schematic for the synthesis of nucleic acid synthons.

1. Definitions a. As used herein a "branched composition" shall mean a non-natural ether and/or alcohol which comprises at least one atom to which is covalently linked at least three different atoms independently selected from the group consisting of carbon, nitrogen, sulfur and oxygen. Without limitation, the branched composition typically does not comprise a primary or secondary amino groups but may comprise a tertiary amine because a tertiary amine is by comparison non-nucleophllic.

b. As used herein a "multiply branched composition" shall mean a non-natural ether and/or alcohol which comprises at least two different atoms to each of which are covalently linked at least three different atoms independently selected from the group consisting of carbon, nitrogen, sulfur and oxygen. Without limitation, the multiply branched composition typically does not comprise a primary or secondary amino groups but may comprise a tertiary amine because a tertiary amine is by comparison non-nucleophilic.

c. As used herein a "modifying moiety" shall mean an ether and/or alcohol moiety which is linked to a polymer or polymer synthon and which comprises at least one atom to which is covalently linked at least three atoms independently selected from the group consisting of carbon, nitrogen, sulfur and oxygen. Without limitation, the modifying moiety typically does not comprise a primary or secondary amino groups but may comprise a tertiary amine because a tertiary amine is by comparison non-nucleophilic.

d. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

e. As used herein, the term "nucleobase sequence" is any segment of a polymer which comprises nucleobase containing subunits. Non-limiting examples of suitable polymers or polymers segments include oligonucleotides, oligoribonucleotides, peptide nucleic acids, nucleic acid analogs, nucleic acid mimics or chimeras.

f. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to those nucleic acid mimics described in the following publications: Diderichsen et al., *Tett. Lett.* 37:475–478 (1996); Fujii et al., *Bioorg. Med. Chem. Lett.* 7:637–627 (1997); Jordan et al., *Bioorg. Med. Chem. Lett.* 7:687–690 (1997); Krotz et al., *Tett. Lett.* 36:6941–6944 (1995); Lagriffoul et al., *Bioorg. Med. Chem. Lett.* 4:1081–1082 (1994); Lowe et al., *J. Chem. Soc. Perkin Trans.* 1, (1997) 1:539–546; Lowe et al., *J. Chem. Soc. Perkin Trans.* 11:547–554 (1997); Lowe et al., *J. Chem. Soc. Perkin Trans.* 11:555–560 (1997); Petersen et al., *Bioorg. Med. Chem. Lett.* 6:793–796 (1996); Diederichsen, U., *Bioorganic & Med. Chem. Lett.*, 8: 165–168 (1998); Cantin et al., *Tett. Lett.*, 38: 4211–4214 (1997); Ciapetti et al., *Tetrahedron*, 53: 1167–1176 (1997); Stetsenko et al, *Tett. Lett.*, 37: 3571–3574 (1996) and Lagriffoule et al., Chem. Eur. J., 3: 912–919 (1997).

In preferred embodiments, a PNA is a polymer comprising two or more subunits of the formula:

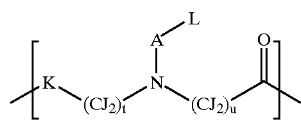

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$— and a group of the formula; —$(CJ_2)_s$C(O)—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin and fluorescein. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

g. As used herein, the term "purine-rich" shall refer to a synthetic polymer, and particularly a PNA oligomer or modified PNA oligomer, characterized by having a purine:purine+pyrimidine ratio of 0.75 or greater.

h. As used herein, the term "modified PNA oligomer" shall refer to a PNA oligomer to which is linked one or more modifying moieties which improve aqueous solubility or otherwise reduce or eliminate polymer self-aggregation including, but not limited to, the modifying moieties described herein. Without limitation, the "modified PNA oligomer" will preferably be modified with one or more of the branched or multiply branched modifying moieties described herein.

i. As used herein, the term "chimera" or "chimeric oligomer" shall mean an oligomer comprising two or more linked subunits which are selected from different classes of subunits. For example, a PNA/DNA chimera would comprise at least two PNA subunits linked to at least one 2'-deoxyribonucleic acid subunit (For methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues of nucleic acids.

j. As used herein, the term "linked polymer" shall mean a polymer comprising two or more polymer segments which are linked by a linker. The polymer segments which are linked to form the linked polymer are selected from the group consisting of an oligodeoxynucleotide, an oligoribonucleotide, a peptide, a polyamide, a peptide nucleic acid and a chimera.

2. Detailed Description

Nucleic Acid Synthesis and Modification

Nucleic acid oligomer (oligonucleotide and oligoribonucleotide) synthesis has become routine. For a detailed description of nucleic acid synthesis please see *Gait, M. J., Oligonucleotide Synthesis: a Practical Approach. IRL Press, Oxord England.* Preferably, nucleic acid oligomers are synthesized on supports in what is known as solid phase synthesis. Alternatively, they are synthesized in solution. Synthesis is typically accomplished by repetitive addition of monomeric subunits (nucleotide or ribonucleotide) commonly referred to as synthons or monomers. A synthesis cycle comprises all the steps (chemical transformations) required to add a monomeric subunit to the oligomer being assembled.

The most common nucleic acid synthesis supports consist of controlled pore glass and other inorganic supports (e.g. 4,415,732, 4,458,066, 4,725,677 and RE 34,069, polystyrene beads (e.g. 4,923,901) and membranes (e.g. 5,262,530). Reagents required to perform a step (chemical transformations) in the chemical assembly cycle can be easily brought into contact with the support and then removed using a flow through system. When brought into contact with the support on which the oligomer is immobilized, the desired chemical transformation of the nucleic acid oligomer occurs. Synthesis cycles can be repeated until the oligomer is the desired length. Because the monomer (synthons) are chosen in each synthetic cycle, the sequence of the oligomer is controlled and known. Thus, the process of assembly using solid phase synthesis is, and has been, automated for many years.

Suitably protected nucleotides are the synthons (monomers) used to assemble nucleic acid oligomers. Those of skill in the art of nucleic acid synthesis would recognize that suitably protected DNA and RNA synthons generally have the formulas illustrated below:

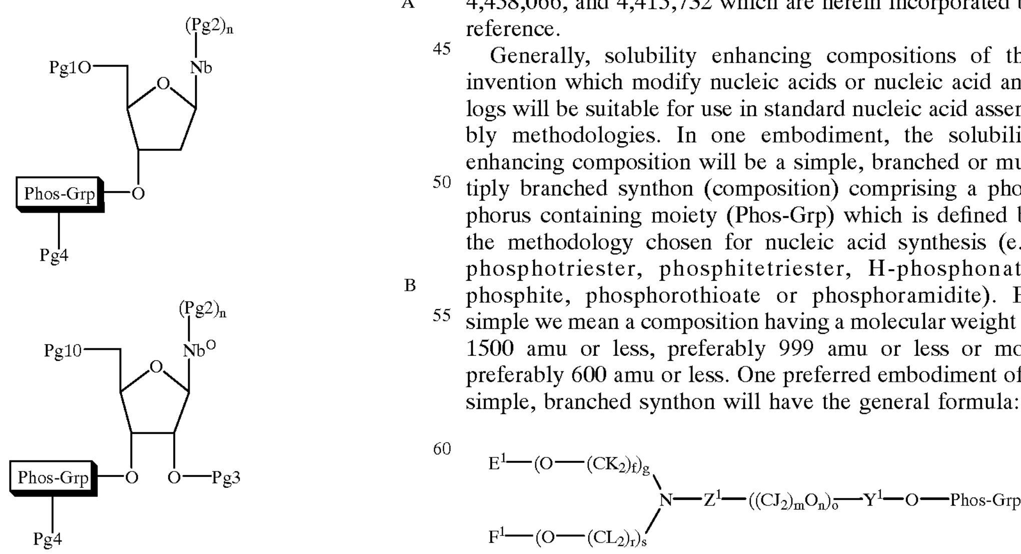

As illustrated, the synthons comprise a ribose (RNA; compound B) or deoxyribose (DNA; compound A) sugar subunit and an attached nucleobase (Nb). There is a 5'-hydroxyl protecting group, Pg1, and optionally one or more protecting groups (Pg2) protecting the nucleophilic functional groups of the nucleobase. The integer n, is the number of nucleobase protecting groups (Pg2s). Typically the nucleobase protecting groups (Pg2s) protect exocyclic amine groups wherein n is the number of exocyclic amine groups in the nucleobase. The synthons represented by compounds A and B are remarkably similar with the primary difference being the presence (RNA) or absence (DNA) of a 2'-hydroxyl group of the sugar subunit. The 2'-hydroxyl group is protected with a protecting group, Pg3, during the chemical assembly of RNA. The Phos-Grp is a branched phosphorus containing moiety which is suitable for reaction with the hydroxyl group of a nudeoside, nucleotide or oligomer. The Phos-Grp is optionally protected with a protecting group, Pg4. Non-limiting examples of phosphorus containing groups (Phos-Grps) known in the art of nucleic acid synthesis include phosphotriesters, phosphitetriester, H-phosphonates, phosphites, phosphorothioate and phosphoramidites. Phosphoramidites are the preferred phosphorus containing group (Phos-Grp). Oligonucleotides synthesis with phosphoramidites was described by Caruthers et al. in U.S. Pat. Nos. 4,415,732 and 4,458,066. Most modern commercial methods and reagents for nucleic acid synthesis utilize phosphorarnidite chemistries generally described by Koester et al. in U.S. Pat. No. 4,725,677 and RE 34,069, wherein the phosphoramidite is a β-cyanoethyl (Pg4) phosphoramidite (Phos-Grp).

Consequently, those of ordinary skill in the art will recognize that both labeled, unlabeled or oligonucleotides (DNA, RNA and synthetic analogues thereof) are readily available. They can be synthesized using commercially available instrumentation and reagents or they can be purchased from commercial vendors of custom manufactured oligonucleotides. Patents which discuss various compositions, supports and methodologies for the synthesis and labeling of nucleic acids include: 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198,540, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732 which are herein incorporated by reference.

Generally, solubility enhancing compositions of this invention which modify nucleic acids or nucleic acid analogs will be suitable for use in standard nucleic acid assembly methodologies. In one embodiment, the solubility enhancing composition will be a simple, branched or multiply branched synthon (composition) comprising a phosphorus containing moiety (Phos-Grp) which is defined by the methodology chosen for nucleic acid synthesis (e.g. phosphotriester, phosphitetriester, H-phosphonate, phosphite, phosphorothioate or phosphoramidite). By simple we mean a composition having a molecular weight of 1500 amu or less, preferably 999 amu or less or most preferably 600 amu or less. One preferred embodiment of a simple, branched synthon will have the general formula:

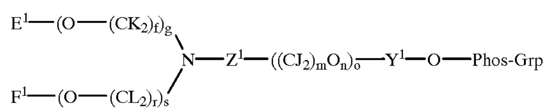

As used herein, the moiety $Z^1$ is selected from the group consisting of: —C(O)— and —C(S)—. The moiety $Y^1$ is a group having the formula: —$(CI_2)_e$—, wherein e is a whole number from 1 to 10. Each of the moieties, $E^1$ and $F^1$, are independently selected from the group consisting of Pg5 and $R^1$. The number o is a whole number from 0 to 10. Each number n is independently 0 or 1. Each number f, g, m, r and s is independently a whole number from 1 to 10. Each I, J, K and L is independently selected from the group consisting of: H, X and $R^1$. Each $R^1$ is independently selected from the group consisting of: —$CD^3$, —$CD^2CD^3$, —$CD_2CD_2CD_3$, —$CD_2CD(CD_3)_2$, and —$C(CD_3)_3$. Each moiety D is independently selected from the group consisting of —H, —O—Pg5 and X. Each Pg5 is independently a hydroxyl protecting group. Non-limiting examples of preferred hydroxyl protecting groups include trityl protecting groups (e.g. triphenylmethyl, 4-methoxytriphenylmethyl, 4,4'-dimethoxytriphenylmethyl), silyl protecting groups (e.g. trimethylsilyl, triethylsilyl, tert-butyldimethylsilyl, triisopropylsilyl and trimethylsilylethyl) and carbonate protecting groups (e.g. benzhydroloxycarbonyl (Bhoc), tert-butyloxycarbonyl (t-boc). Each atom X is independently selected from the group consisting of F, Cl, Br and I. The Phos-Grp moiety will be a group suitable reaction with the nucleic acid under conditions typically used for the nucleic acid synthesis methodology chosen. Non-limiting examples of a preferred Phos-Grp include phosphotriester, phosphitetriester, H-phosphonate, phosphite, phosphorothioate or phosphoramidite groups. Most preferably the Phos-Grp shall be a phosphoramidite, and particularly a β-cyanoethylphosphoramidite. One very useful β-cyanoethylphosphoramidite is a simple, multiply branched compound having the formula:

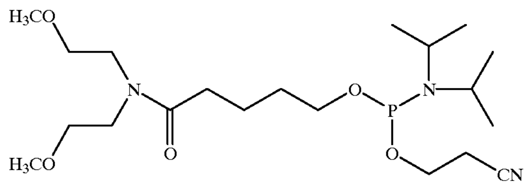

With reference to FIG. 1A, a method for the synthesis of preferred branched or multiply branched compositions suitable for modifying synthetic oligonucleotides with solubility enhancing moieties is presented. With reference to the Figure, a secondary amine I is reacted with a lactone (or thio lactone) II to thereby generate the alcohol III. If one of the starting materials (i.e. I or II) is liquid, this reaction may be performed without the addition of a solvent, provided care is taken when mixing the reagents. Alternatively, a non-nucleophilic solvent such as dichloromethane, diethylether, tetrahydrofuran, dioxane or N,N'-dimethylformamide can be used to mediate the reaction between components I and II. Often it will be preferable to include a non-nucleophilic base such as triethylamine or N,N'-diisopropylethylamine in the reaction to neutralize any excess acid which might otherwise be present during the reaction. Typically, the reaction will proceed at ambient temperature but may be heated if the reagents are slow to react.

With reference to the Figure, the alcohol III is then reacted with an appropriate phosphorus containing moiety (Phos-Mty) to thereby prepare synthon IV. The Phos-Mty will be selected depending on the nature of the preferred nucleic acid synthesis methodology. The reaction conditions used to react the alcohol III with the Phos-Mty shall be consistent with those typically used to convert suitably protected nucleosides to synthons used in the nucleic acid synthesis methodology chosen (e.g. a H-phosphonate or phosphoramidite synthon).

For example, a preferred Phos-Mty is 2'-cyanoethyl-N,N-diisopropyl-chlorophosphoramidite which is used to convert the alcohol III to a β-cyanoethylphos-phoramidite IV. Typically a β-cyanoethylphosphoramidite of this invention is prepared by the reaction of an alcohol (e.g. compound III) with 2'-cyanoethyl-N,N'-diisopropyl-chlorophosphoramidite in an anhydrous non-nucleophilic solvent (e.g. tetrahydrofuran) in the presence of an organic non-nucleophilic base (e.g. triethylamine or N,N'-diisopropylethylamine) at or below ambient temperature.

Figure 1B:
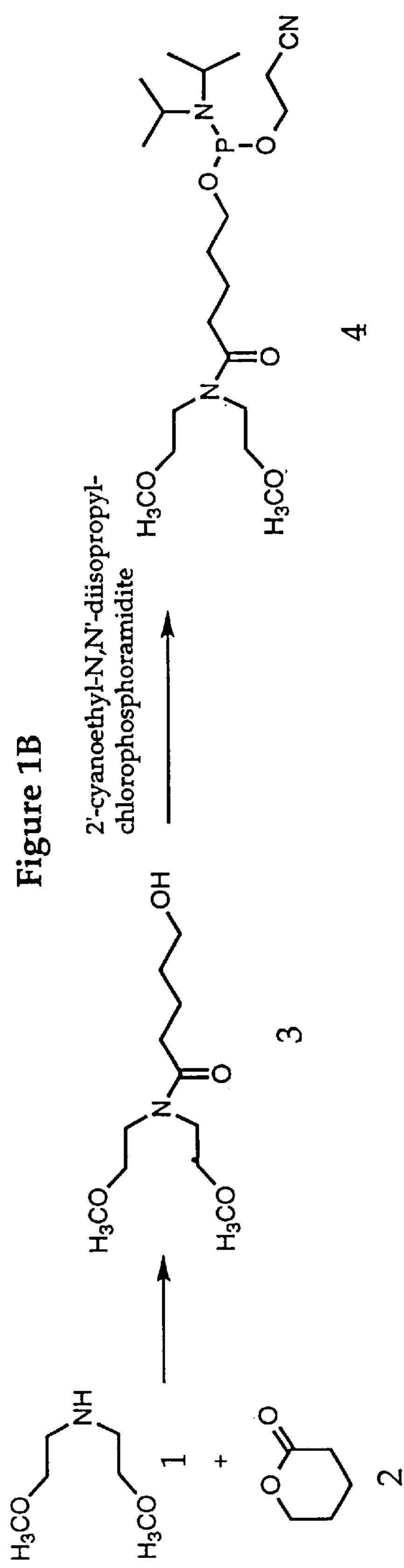
FIG. 1B is a schematic for the synthesis of preferred nucleic acid synthons.

With reference to FIG. 1B, preparation of an exemplary synthon is illustrated. The secondary amine 1 reacts with the lactone 2 to form the alcohol 3. The alcohol 3 is then reacted with 2'-cyanoethyl-N,N'-diisopropyl-chlorophosphoramidite to thereby yield the preferred β-cyanoethylphosphoramidite 4.

When incorporated in the nucleic acid, the compositions of this invention may be nucleophilic or non-nucleophilic depending on the nature of the starting materials chosen. For example, the secondary amine I (See: FIG. 1A) may optionally contain one or more protected hydroxyl groups (moieties $E^1$ or $F^1$) which, upon removal of the protecting group (Pg5), will generate a modifying moiety having one or more hydroxyl groups (a nucleophilic group). Alternatively, the moieties $E^1$ or $F^1$ comprise alkyl groups ($R^1$) which generate modifying ether moieties which are non-nucleophilic. Having the benefit of this description, one of ordinary skill in the art will recognize the advantages and disadvantages associated with nucleophilic and non-nucleophilic groups and will therefore choose compositions with appropriate branched or multiply branched moieties which are suitable for preparing a solubility enhanced synthetic nucleic acids or nucleic acid analogs.

When incorporated in the nucleic acid or nucleic acid analog, the compositions of this invention may be chiral or achiral depending on the nature of the starting materials chosen. For example, the substituents K and L of the secondary amine I (See: FIG. 1A) may be chosen to thereby generate a modifying moiety having one or more chiral centers. Alternatively, the substituents J and $Y^1$ of the lactone II, may be chosen to thereby generate a modifying moiety having one or more chiral centers. Preferably, however, the starting materials are achiral so that the modified nucleic acids or modified nucleic acid analogs prepared do not exist as enantomeric or diasteriomeric mixtures which are themselves generally difficult to purify or characterize.

Consequently, in another embodiment, the invention relates to kits comprising compositions suitable for enhancing the solubility of synthetic nucleic acids and particularly nucleic acid analogs. Preferred branched or multiply branched compositions which are included in the kits of this invention have the formula:

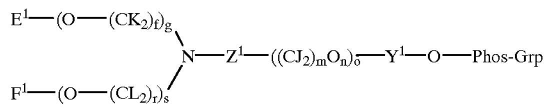

wherein, $E^1$, $F^1$, J, K, L, $Z^1$, $Y^1$, Phos-Grp, e, f, g, m, n, o, r and s have been previously defined. Synthon 4 is a preferred composition to be included in the kits of this invention.

Because they enhance the solubility of nucleic acids, these compositions are particularly well suited for improving the solubility of modified nucleic acids and particularly nucleic acid analogues which contain modified backbones.

Varma et al. summarize numerous nucleic acid analogs in a comprehensive review article (See: Varma et al., *Synlett*, 9: 621–637 (September, 1993)). Non-limiting examples of nucleic acid analogs include the alternative Phosphate-Containing Linkages such as Phosphorothioates, Phosphorodithioates, Methylphosphonates, Phosphoramidates and Phosphate esters. In other oligonucleotide analogs the phosphate backbone has been replaced. Non-limiting examples of analogs containing a Phosphate Free-Backbone include those polymers having Carbonate linkages, Carboxymethyl linkages, Acetamide linkages, Carbamate linkages (including morpholino compounds such as those described in U.S. Pat. Nos. 5,185,444, 5,034,506 and 5,142,047, herein incorporated by reference), Thioether linkages, Sulfonate linkages, Sulfonamide linkages, Sulfamate linkages, Sulfide linkages, Sulfoxide linkages, Sulfone linkages, Formacetal and Thioformacetal linkages, Methyhydroxylamine linkages, N-cyanoguanidine linkages and alkylsilyl linkages.

Similarly, De Mesmaeker et al. summarize numerous nucleic acid analogs in a comprehensive review article. As used herein those polymers referred to in Tables 1 and 2 by De Mesmaeker et al. shall be nucleic acid analogs. However, PNAs are independently characterized (not nucleic acid analogs) since they " . . . do not bear any structural resemblance to natural oligonucleotides, other than the nucleic acid bases present on the acetic acid side chains." (See. De Mesmaeker et al., *Current Opinion in Structural Biology*, 5: 343–355 (1995) at p. 349, col. 1, lns. 43–47).

The term nucleic acid analog(s) shall also apply to polymers referred to as LNA (See: Koshkin et al., *Tett. Lett.*, 39: 4381–4384 (1998) and Koshkin et al., *Tetrahedron*, 54: 3607–3630 (1998) as well as Arya et al., *J. Am. Chem. Soc.*, 120: 6619–6620 (1998).

Generally, nucleic acid analogs differ from nucleic acid mimics in that nucleic acid analogs retain at least one structural feature of the sugar phosphate backbone of a natural nucleic acid whereas nucleic acid mimics comprise a backbone which is such a radical departure from the natural nucleic acid that the presence of nucleobases is the only common structural feature between an natural nucleic acid and a nucleic acid mimic.

As a group, nucleic acid analogs are generally less soluble than are naturally occurring nucleic acids. The polymers comprising uncharged backbones tend to be the least water soluble. Consequently, this invention is particularly directed to nucleic acid analogs which are modified with branched or multiply branched compositions to thereby improve water solubility or minimize or eliminate polymer self-aggregation.

Consequently, embodiments of this invention also pertain to modified nucleic acid oligomers and particularly modified oligonucleotide analogues comprising branched of multiply branched modifying moieties which have been incorporated using the compositions previously described (e.g. IV or 4) and methodologies known to those of ordinary skill in the art. Preferably, the modifying moieties are simple, branched or multiply branched moieties. Preferred modified nucleic acids and nucleic acid analogs of this invention shall comprise one or more modifying moieties having the formula:

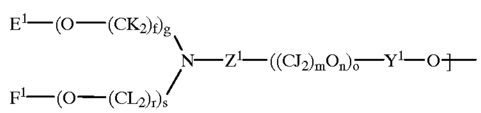

wherein, $E^1$, $F^1$, J, K, L, $Y^1$, $Z^1$, e, f, g, r, s, m, n, and o have been previously defined. An exemplary modifying moiety is a group having the formula:

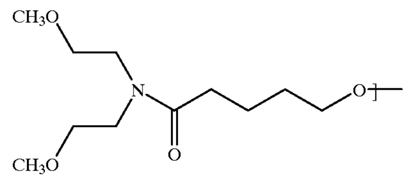

Polyamide, PNA & Peptide Synthesis:

Like nucleic acid synthesis, peptides, polyamides and peptide nucleic acids are typically assembled in a stepwise cyclic process from monomeric subunits. Polyamide, peptide and PNA assembly is routinely performed on a synthesis support or performed in solution. Chemicals and instrumentation for the support bound automated chemical assembly of peptides and polyamides have long been known and commercially available. Methods and compositions for the chemical assembly of PNAs are known (See: U.S. Pat. Nos. 5,539,082, 5,527,675, 5,623,049, 5,714,331, 5,736,336, 5,773,571 or 5,786,571, all of which are herein incorporated by reference). Chemicals and instrumentation for the support bound automated synthesis of peptide nucleic acids are also now commercially available (See: PerSeptive Biosystems Product and Promotional Literature).

Suitably protected amino acid synthons are the monomeric subunits typically used to assemble polyamides, PNAs and peptides. Because of their structural similarity, the protecting groups, synthesis supports, activation chemicals and synthetic methodologies are typically the same or similar for the assembly of polyamides, peptides and PNAs.

Because a PNA oligomer is a polyamide (or pseudopeptide), it has a C-terminus (carboxyl terminus) and an N-terminus (amino terminus). For the purposes of the design of a hybridization probe suitable for antiparallel binding to a nucleic acid target (the preferred orientation), the N-terminus of the PNA probe is the equivalent of the 5'-hydroxyl terminus of an equivalent DNA or RNA probe.

PNA, Peptide and Polyamide Labeling or Modification:

Because the synthetic chemistry of assembly is essentially the same, any method commonly used to label/modify a peptide can usually also be used to label/modify a PNA or other polyamide. Generally the methods for labeling or modification described in this section can be used to modify most amine containing polymers but for simplicity, reference will typically be made only to PNA, peptide and polyamides. For example, a polyamide, PNA or peptide may be modified by condensation of a suitable carboxylic acid moiety with the N-terminus or side chain nucleophilic group (e.g. amine, hydroxyl or thiol) of the polymer during chemical assembly. Such condensation reactions are well known in the art of organic chemistry. Alternatively, if polymer assembly is to be continued after N-terminal modification or labeling, typically a suitably protected amino acid synthon is used so that the amino group of this synthon can be used to further extend the polymer.

Preferred compositions of this invention which are suitable for modifying PNA, peptides, and other polyamides will comprise a branched or multiply branched composition or synthon which is condensed or reacted with a nucleophihc group of the polymer. Preferred compositions of this invention will exist as branched or multiply branched suitably protected amino acid synthons (composition) which can be incorporated at any position of the polymer sequence without terminating polymer assembly. More specifically, one embodiment of this invention is related to simple, branched or multiply branched compositions (or synthons) which can be used to modify polyamides, peptides and particularly PNA oligomers, to thereby enhance solubility and/or reduce or eliminate polymer self-aggregation.

Typically, the N-terminus of the polymer (e.g. peptide, PNA or polyamide) is labeled or modified by reaction or condensation with a labeling reagent (e.g. a reactive fluorophore such as 5(6)carboxyfluorescein-NHS) or modifying moiety (e.g. a Branched Acid Composition, Branched Hydroxyl Composition, Branched Alkyl Halide Composition or Suitably Protected Multiply Branched Amino Acid Synthon as described herein). One or more spacer moieties can optionally be introduced between the label or modifying moiety and the oligomer. Generally, the spacer moiety is incorporated prior to performing the labeling reaction. However, the spacer may be embedded within the label or modifying moiety and thereby be incorporated during the labeling or modification reaction.

Similarly, the polymer can be extended with an amino acid spacer moiety before a desired labeling or modification is performed (e.g. Expedite™ PNA Linker; a.k.a. Fmoc-8-amino-3,6-dioxaoctanoic acid). Generally, spacers are used to minimize the adverse effects that bulky labeling/modifying reagents might have on the interactions of the polyamide, peptide or PNA oligomer with other molecules of interest (e.g. the hybridization properties of a PNA oligomer with a target nucleic acid).

Similarly, the C-terminal end of a polyamide may also be modified with one or more labels (e.g. a fluorophore) or modifying moieties (e.g. a Branched Acid Composition, Branched Hydroxyl Composition, Branched Alkyl Halide Composition or Suitably Protected Multiply Branched Amino Acid Synthon as described herein). Generally, the C-terminal end of a polyamide is modified by first condensing one or more of the desired labeling reagents or modifying moieties with the support upon which the polymer is to be assembled. Suitably protected amino acids are the preferred labeling reagents of modifying moieties (e.g. Expedite™ PNA Linker; a.k.a. Fmoc-8-amino-3,6-dioxaoctanoic acid, Fmoc-"E"aeg-OH, Fmoc-"+"aeg-OH, N-α-(Fmoc)-N-ε-(t-boc)-L-lysine-OH and/or N-α-(Fmoc)-N-ε-(dabcyl)-L-Lysine-OH). Once the support has been appropriately modified with the desired combination of linkers and/or modifying moieties, the polymer is then assembled using the terminal amino group of the support bound labeling reagent or modifying moiety as an anchor. Once completely assembled, the polymer is then, cleaved deprotected and optionally purified using the standard methodologies.

Alternatively, a functional group on the assembled, or partially assembled polymer is labeled or modified with a suitable moiety while the polymer is still support bound. This method requires that an appropriate protecting group be incorporated into the oligomer to thereby yield a reactive functional group to which the label or modifying moiety is linked (by reaction or condensation) but has the advantage that the label (e.g. a fluorophore) or modifying moiety (e.g. a Branched Acid Composition, Branched Hydroxyl Composition or Branched Alkyl Halide Composition, as described herein) can be attached to any position within the polymer. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from polymer by treatment of the resin under mildly acidic conditions. Consequently, the labeling reagent or modifying moiety can then be condensed with the ε-amino group of the lysine anino acid. After complete assembly and appropriate labeling or modification, the polymer is then cleaved from the support, deprotected and purified using well known methodologies.

By still another method, the label (e.g. a fluorophore) or modifying moiety (e.g. a Branched Acid Composition, Branched Hydroxyl Composition, Branched Alkyl Halide Composition or Suitably Protected Multiply Branched Amino Acid Synthon as described herein) is attached to the polymer after it is fully assembled and cleaved from the support. This method is preferable where the label or modifying moiety is incompatible with the cleavage, deprotection or purification regimes commonly used to manufacture the oligomer. By his method, the polymer will generally be labeled or modified in solution by the reaction of a functional group on the polymer and a functional group on the labeling reagent or modifying moiety. Those of ordinary skill in the art will recognize that the composition of the coupling solution will depend on the nature of oligomer and the label or modifying moiety. The solution may comprise organic solvent, water or any combination thereof. Generally, the organic solvent will be a polar non-nucleophilic solvent. Non limiting examples of suitable organic solvents include acetonitrile, tetrahydrofuran, dioxane, methyl sulfoxide and N,N'-dimethylformamide.

For solution reactions, generally the functional group on the polymer to be labeled or modified will be an amine and the functional group on the label or modifying moiety will be a carboxylic acid or activated carboxylic acid. Non-limiting examples of activated carboxylic acid functional groups include N-hydroxysuccinimidyl esters. In aqueous solutions, the carboxylic acid group of either of the polymer or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably, the pH during the condensation is in the range of 4–10. When an arylamine is condensed with the carboxylic acid, preferably the pH is in the range of 4–7. When an alkylamine is condensed with a carboxylic acid, preferably the pH is in the range of 7–10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using biological buffers such as N-[2-hydroxyethyl]piperazine-N'-[2-ethanesulfonic acid (HEPES) or 4-morpholineethane-sulfonic acid (MES) or inorganic buffers such as sodium bicarbonate.

Spacer/Linker Moieties:

Spacers are typically used to minimize the adverse effects that bulky labeling reagents or modifying moieties might have on hybridization properties of a polymer such as a PNA or nucleic acid probe. Linkers typically induce flexibility and randomness into a polymer or otherwise link two or more polymer segments. Preferred spacer/flexible linker moieties consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid) or alkyloxy diacids (e.g. diglycolic acid). The spacer/linker moieties may also enhance the solubility of the polymer.

Preferably, a spacer/linker moiety comprises one or more linked compounds having the formula: $—Y—(O_m—(CW_2)_n)_o—Z—$. The group Y is a single bond or a group having the formula selected from the group consisting of: $—(CW_2)_p—$, $—C(O)(CW_2)_p—$, $—C(S)(CW_2)_p—$ and $—S(O_2)(CW_2)_p$. The group Z has the formula NH, $NR^2$, S or O. Each W is independently H, $R^2$, $—OR^2$, F, Cl, Br or I; wherein, each $R^2$ is independently selected from the group consisting of: $—CX_3$, $—CX_2CX_3$, $—CX_2CX_2CX_3$, $—CX_2CX(CX_3)_2$, and $—C(CX_3)_3$. Each X is independently H, F, Cl, Br or I. Each m is independently 0 or 1. Each n, o and p are independently integers from 0 to 10. In the most preferred embodiment, the spacer/flexible linker comprises two linked 8-amino-3,6-dioxaoctanoic acid moieties. Thus, preferably Y is $—C(O)(CW_2)_p—$, Z is NH, each W is H, m is 1, n is 2, o is 2 and p is 1.

Branched Compositions Suitable for Modifying Polyamides, Peptides and PNAs

Applicants have invented branched compositions which can be linked to polymers to thereby improve polymer solubility and/or which minmizes or eliminates polymer self-aggregation. Preferably the branched compositions are simple compositions. By simple we mean a composition having a molecular weight of 1500 amu or less, preferably 999 amu or less or most preferably 600 amu or less.

These solubility enhancing branched compositions may, depending of the nature of the starting materials, be charged or uncharged (at physiological pH), nucleophilic or non-nucleophilic and chiral or achiral, though they are preferably achiral. The compositions of this invention are particularly well suited for use in PNA synthesis to thereby overcome limitations known in art which relate to synthesizing, purifing and characterizing PNA oligomers, and particularly purine-rich PNA oligomers. The branched compositions can be used directly to modify polyamide, peptide or PNA oligomers by the reaction with nucleophiles of the polymer using well known methodologies (For example, see subheading "PNA, Peptide and Polyamide Labeling or Modification"). Alternatively, the branched composition (e.g. a Branched Acid Composition, Branched Hydroxyl Composition or Branched Alkyl Halide Composition, as described herein) can be used to prepare suitably protected multiply branched amino acid synthons which are then used to modify the polymer during chemical polymer assembly except that the amino acid synthons have the advantage that they can be linked at the N-terminus of the polymer without terminating polymer assembly.

The incorporation of charged moieties into synthetic polymers may be desired where, for example, there is a need to cause the polymer to be attracted to or repelled by another molecule. With regard to PNA, it has been demonstrated that the kinetics of hybridization between positively charged PNAs and negatively charged nucleic acids is significantly faster (See: Corey et al., *J. Am. Chem. Soc*., 117: 9373–9374 (1995) and Corey et al., *FASEB Journal*, 9: A1391 (1995)). Positively charged moieties might be expected to improve water solubility of a compound as compared with a neutral moiety. Nonetheless, charged moieties may induce undesirable properties into a polymer such as an affinity for surfaces or other molecules with which the polymer should not interact. Therefore, it is useful to have the option to design compositions which are charged or uncharged.

The incorporation of nucleophilic moieties into synthetic polymers may be desired where, for example, there is a need to react the polymer with another molecule (e.g. for labeling or otherwise modifying the molecule of interest). Alternatively, nucleophilic groups such as hydroxyl groups, amino groups and thiols can be used to enhance the water solubility of the molecule irrespective of the nucleophilic character of the functional group. However, the nucleophilic character of a primary or secondary amine, hydroxyl or thiol group may result in undesired properties when incorporated into a polymer. For example, the presence of nucleophiles, such as a primary amino group of a lysine amino acid, on a PNA probe may result in unwanted reactions with components of a research or diagnostic assay. Therefore, it is useful to have the option to design compositions of this invention which are nucleophilic or non-nucleophilic. Provided they convey desirable solubility properties, there is a preference for non-nucleophilic compositions. However, if a nucleophilic moiety is unavoidable, there is a preference for hydroxyl groups over thiol and primary or secondary amino groups.

The introduction of one or more chiral centers into a synthetic polymer can result in the production of enantiomers or diasterioisomers. Chiral compositions are generally avoided because the resulting mixture of products are usually difficult to purify or characterize. Consequently, the compositions of this invention shall preferably, but not exclusively, be achiral.

A preferred combination of the aforementioned variables is a modifying moiety or synthon which is uncharged, non-nucleophilic and achiral. Another preferred combination of the aforementioned variables is a modifying moiety or synthon which is positively charged (at physiological pH), non-nucleophilic and achiral. A third preferred combination of the aforementioned variables is a modifying moiety or synthon which is uncharged, achiral and contains only hydroxyl groups as nucleophiles.

i. Branched Acid Compositions:

As previously discussed under the subheading "PNA, Peptide and Polyarnide Labeling or Modification", compositions comprising acid moieties (e.g. carboxylic acid or sulfonic acid) can be condensed with polyamides, peptides, PNAs and other polymers during chemical assembly. Typically, this will occur by condensation with the N-terminus of the polyamide. Alternatively, compositions comprising an acid moiety may be condensed with the nucleophilic functional group of a side chain (e.g. the ϵ-amino group of lysine, the hydroxyl group of serine or threonine or the thiol of cystine). For the condensation reactions to be selective and efficient, any nucleophilic groups of the acid moiety should be protected with a protecting group (e.g Pg5 as defined herein). In preferred embodiments, the branched compositions are simple, branched compositions.

Preferred acid compositions of this invention, which are suitable for incorporation into polyamides or other polymers to thereby improve water solubility and/or reduce or eliminate polymer self-aggregation, have the general formula:

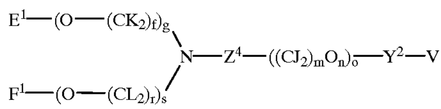

As used herein, the moiety $Z^4$ is selected from the group consisting of: —C(O)—, —C(S)—, —$S(O_2)$— and a bond. The moiety V is selected from the group consisting of: —C(O)OH, —C(S)OH, and —$S(O_2)$OH. The moiety $Y^2$ is selected from the group consisting of a bond and a group having the formula: —$(CI_2)_e$—, wherein e is a whole number from 1 to 10. Each of the moieties $E^1$ and $F^1$, I, J, K and L and the numbers e, f, g, m, n, o, r and s are previously defined.

Figure 2A:
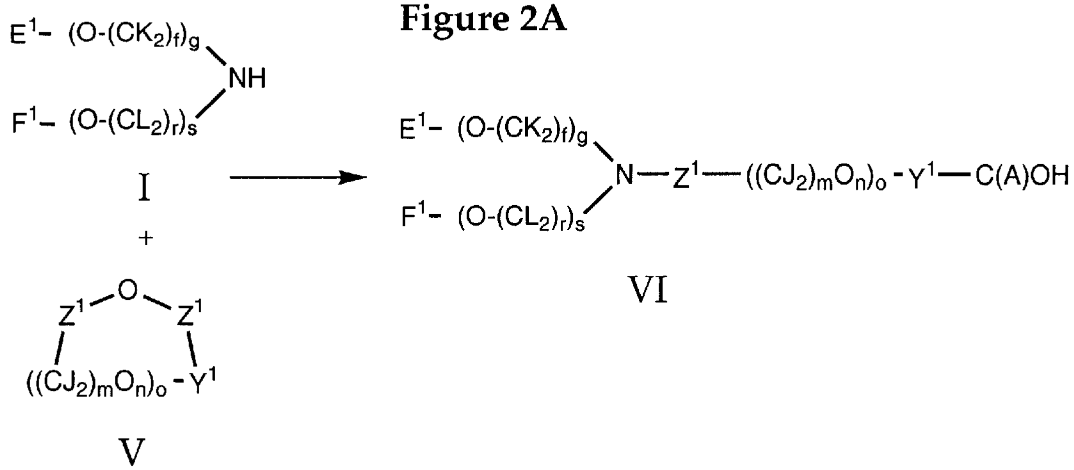
FIGS. 2A–2C are schematics for the synthesis of preferred Acid Compositions.

With reference to FIG. 2A, a general synthetic method is presented for the preparation of several branched acid compositions suitable for the practice of this invention. According to the method, the secondary amine I is reacted with the anhydride V to thereby form the uncharged carboxylic acid VI. If one of the starting materials (ie. I or VI) is liquid, this reaction may be performed without the addition of a solvent, provided care is taken when mixing the reagents. Alternatively, a non-nucleophilic solvent such as dichloromethane, diethylether, tetrahydrofuran dioxane or N,N'-dimethylformamide can be used to mediate the reaction between components I and V. Cne or more equivalents of the secondary amine I may also be added to the reaction to neutralize the carboxylic acid VI formed by the reaction. Alternatively, a non-nucleophilic base such as triethylamine or N,N'-diisopropylethylamine may be added to neutralize the acid equivalent. Typically, the reaction will proceed at ambient temperature but may be heated if the reagents are slow to react. With reference to FIG. 2A, the moieties $E^1$, $F^1$, J, K, L, $Y^1$ and $Z^1$, and the numbers e, f, g, m, n, o, r, and s have been previously defined. The atom A is oxygen or sulfur.

Figure 3A:
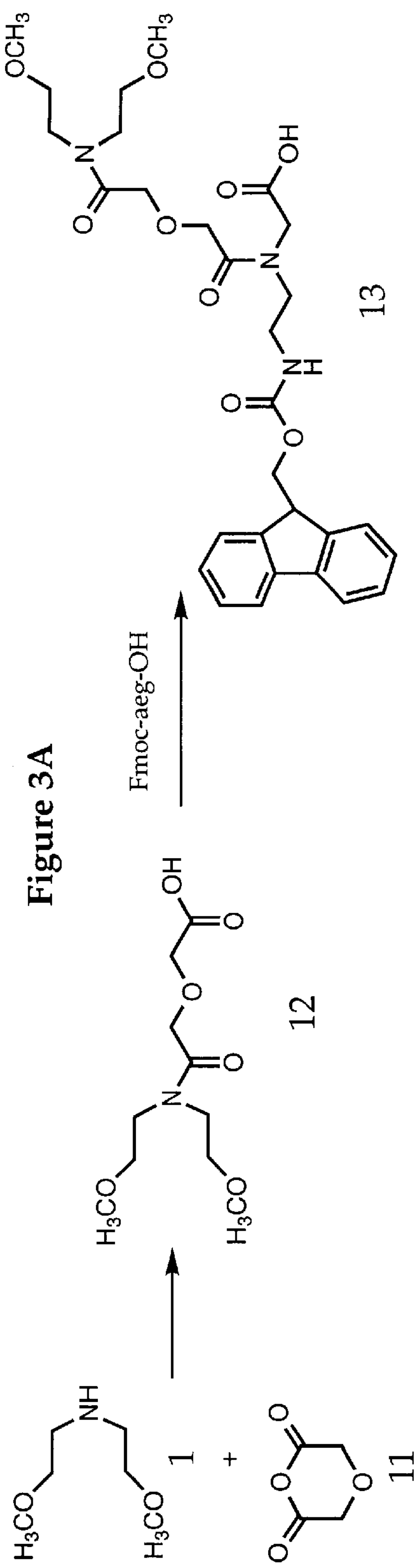
FIG. 3A is a schematic for the synthesis of Fmoc-"E"aeg-OH, 13.

An exemplary synthesis is illustrated in FIG. 3A, wherein compound 1 is reacted with the anhydride 11 to form the achiral, non-nucleophilic, carboxylic acid 12.

Figure 2B:
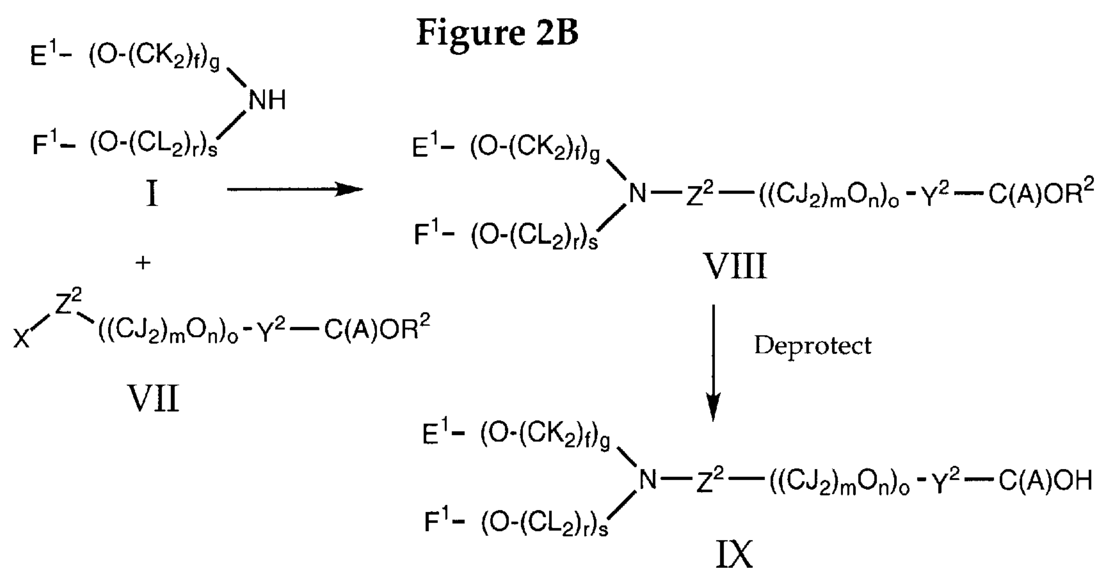

With reference to FIG. 2B, another general synthetic method is presented for the preparation of several other acid containing moieties suitable for the practice of this invention. According to the method, a suitably protected alkyl halide VII is reacted with a secondary amine I to thereby form the protected tertiary amine VIII. Because this compound is a tertiary amine, it will be positively charged at physiological pH. With reference to FIG. 2B, the moieties $E^1$, $F^1$, J, K, L, X, $Y^2$, A, and the numbers e, f, g, m, n, o, r, and s have been previously defined. The moiety $Z^2$ is a bond and the group $R^2$ is an alkyl group. Non-limiting examples of alkyl groups include methyl, ethyl, propyl, isopropyl and tert-butyl.

If one of the starting materials (i.e. I or VII) is liquid, this reaction may be performed without the addition of a solvent, provided care is taken when mixing the reagents. Alternatively, a non-nucleophilic solvent such as dichloromethane, diethylether, tetrahydrofuran, dioxane or N,N'-dimethylformamide can be used to mediate the reaction between components I and VII. Typically, the secondary amine I will be present in at least two equivalents to thereby act as a base to scavenge the acid formed by the reaction. Alternatively, a non-nucleophilic base such as triethylamine or N,N'-diisopropylethylamine may be added to neutralize the acid equivalent. Typically, the reaction will proceed at ambient temperature but may be heated if the reagents are slow to react.

With reference to FIG. 2B, the protecting group, $R^2$, of the carboxylic acid is then removed to thereby generate the carboxylic acid moiety IX. Depending on the nature of the ester, it can be saponified with base or removed by treatment with acid. Methods for the deprotection of esters are well known to those of ordinary skill in the art.

Figure 3B:
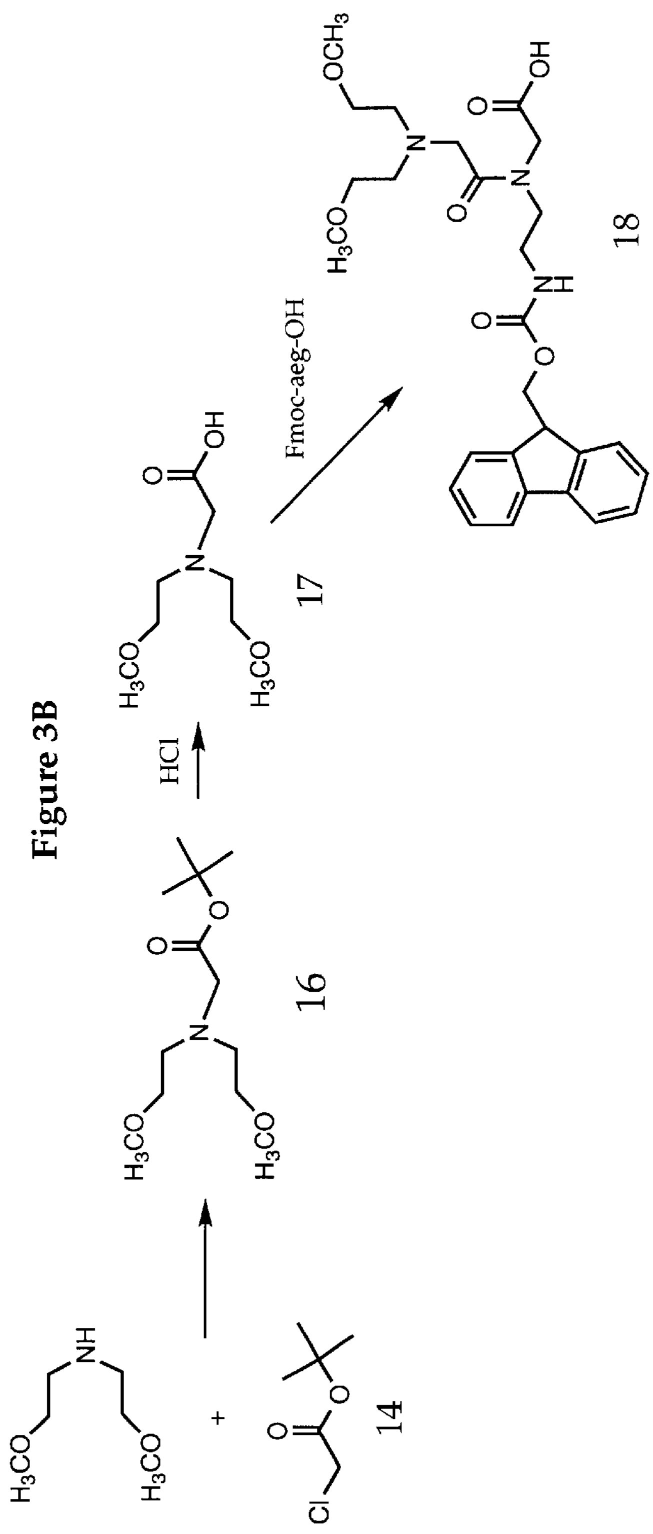
FIG. 3B is a schematic for the synthesis of Fmoc-"+"aeg-OH, 18.

An exemplary synthesis is illustrated in FIG. 3B, wherein compound 1 is reacted with the alkyl halide 14 to form the ester 16. The ester 16 is then treated with acid to remove the tert-butyl protecting group and thereby generate the achiral, non-nucleophilic, zwitterion 17. When condensed with a nucleophile, the tertiary amine of the newly formed compound will be positively charged at physiological pH.

Figure 2C:
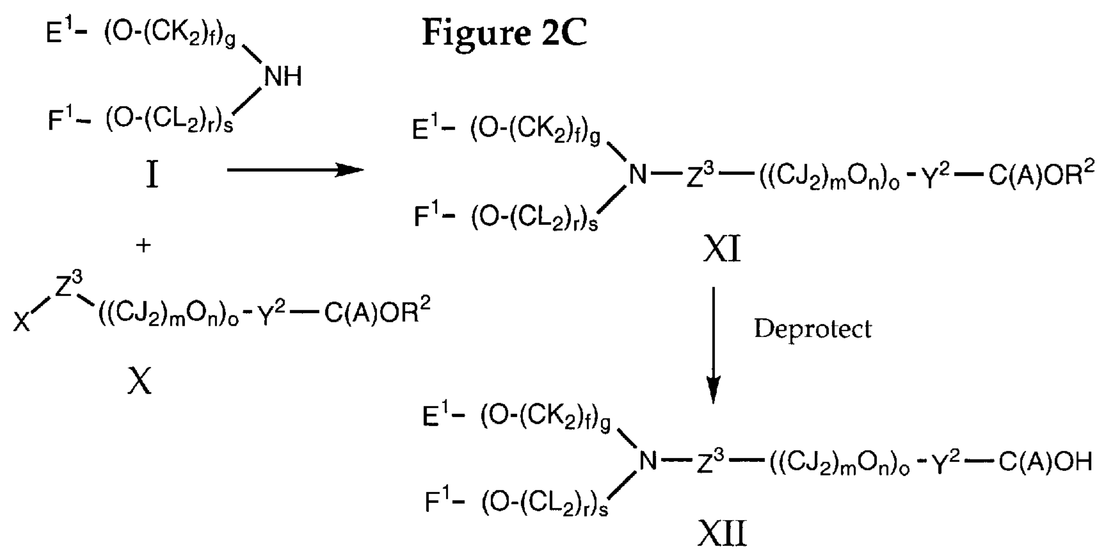

With reference to FIG. 2C, a general synthetic method is presented for the preparation of still other acid containing moieties suitable for the practice of this invention. According to the method, a suitably protected sulfonyl halide X is reacted with a secondary amine I to thereby form the protected sulfonamide XI. With reference to FIG. 2C, the moieties A, $E^1$, $F^1$, J, K, L, $R^2$, X, and $Y^2$, and the numbers e, f, g, m, n, o, r, and s have been previously defined. The moiety $Z^3$ is —$S(O)^2$—.

If one of the starting materials (i.e. I or X) is liquid, this reaction may be performed without the addition of a solvent, provided care is taken when mixing the reagents. Alternatively, a non-nucleophilic solvent such as dichloromethane, diethylether, tetrahydrofuran, dioxane or N,N'-dimethylformamide can be used to mediate the reaction between components I and X Typically the secondary amine will be present in at least two equivalents to thereby act as a base to scavenge the acid formed by the reaction. Alternatively, a non-nucleophilic base such as triethylamine or N,N'-diisopropylethylamine may be added to neutralize the acid equivalent Typically, the reaction will proceed at ambient temperature but may be heated if the reagents are slow to react.

The protecting group $R^2$ (previously defined) of the carboxylic acid is then removed to thereby generate the carboxylic add moiety XII. Depending on the nature of the ester, it can be saponified with base or removed by treatment with acid. Methods for the deprotection of esters are well known to those of ordinary skill in the art.

ii. Branched Hydroxyl Compositions

Branched alcohols may likewise be linked to polyamides, peptides and PNAs during chemical assembly. Preferably the branched alcohols is a simple, branched alcohoL Typically, modification of the polymer occurs by reaction of the hydroxyl group with a carbonyl equivalent to thereby generate a species suitable for reaction with nucleophilic functional groups a a(e.g. the N-terminus or the nucleophilic functional groups of a side chain) of the polymer. Examples of carbonyl equivalents include N,N-carbonyldiimidazole, phosgene, diphosgene, triphosgene and their thiol equivalents (e.g. thiophosgene). For these reactions to be selective and efficient, other nucleophilic groups of the hydroxyl containing moiety should be protected with a protecting group (e.g. Pg5). Typically, these reactions are performed in a non-nucleophilic solvent such as dichloromethane, diethylether, tetrahydrofuran, dioxane or N,N'-dimethylformamide. Generally, the reaction will proceed at ambient temperature but may be heated if the reagents are slow to react. Once the alcohol has been activated, it is then reacted with a nucleophilic functional group of the polymer to thereby generate a covalent linkage.

Preferred hydroxyl compositions of this invention which are suitable for incorporation into polyamides, peptides and PNA to thereby improve water solubility and/or reduce or eliminate polymer self-aggregation have the general formula:

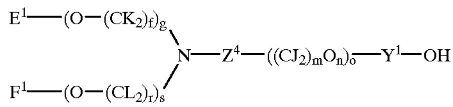

As used herein, the moieties $E^1$, $F^1$, J, K L, $Y^1$ and the numbers e, f, g, m, n, o, r and s have been previously described. The moiety $Z^4$ is selected from the group consisting of selected from the group consisting of: —C(O)—, —C(S)—, —$S(O_2)$— and a bond.

With reference to FIG. 1A, a general synthetic method is presented for the preparation of an alcohol having the general formula III which is suitable for the practice of this invention. Details of this synthesis have been previously described.

Figure 4A:
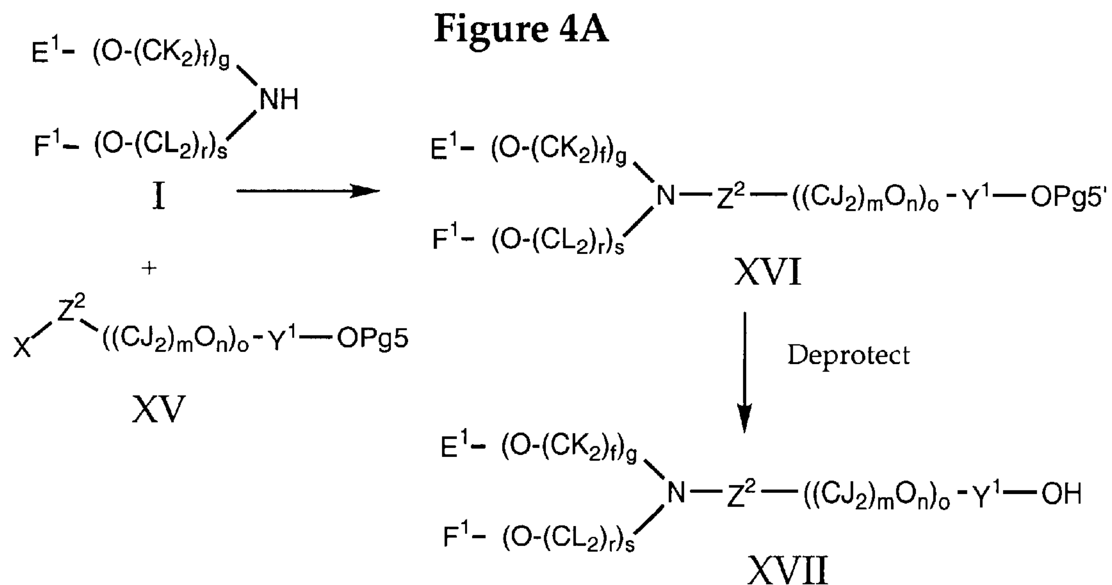
FIGS. 4A and 4B are schematics for the synthesis of preferred Hydroxyl Compositions.

With reference to FIG. 4A, a general synthetic method is presented for the preparation of other alcohols suitable for the practice of this invention. According to the method, a suitably protected alkyl halide XV is reacted with a secondary amine I to thereby form the protected tertiary amine XVI. Because this compound is a tertiary amine, it will be positively charged at physiological pH. The hydroxyl protecting group Pg5' is then removed to thereby generate the alcohol XVII. With reference to FIG. 4A, the moieties $E^1$, $F^1$, J, K, L, X, $Y^1$, $Z^2$ and the numbers e, f, g, m, n, o, r, and s have been previously defined. Suitable hydroxyl protecting groups are known in the art and have previously been described herein provided however that when $E^1$ and/or $F^1$ comprise a hydroxyl protecting group, the hydroxyl protecting group Pg5' is preferably selected such that it can be removed without substantially removing the hydroxyl protecting groups of $E^1$ and/or $F^1$.

If one of the starting materials (ie. I or XV) is liquid, this reaction may be performed without the addition of a solvent, provided care is taken when mixing the reagents. Alternatively, a non-nucleophilic solvent such as dichloromethane, diethylether, tetrahydrofuran, dioxane or N,N'-dimethylformamide can be used to mediate the reaction between components I and XV. Typically the secondary amine will be present in at least two equivalents to thereby act as a base to scavenge the acid formed by the reaction. Alternatively, a non-nucleophilic base such as triethylamine or N,N'-diisopropylethylamine may be added to neutralize the acid equivalent. Typically, the reaction will proceed at ambient temperature but may be heated if the reagents are slow to react.

Figure 4B:
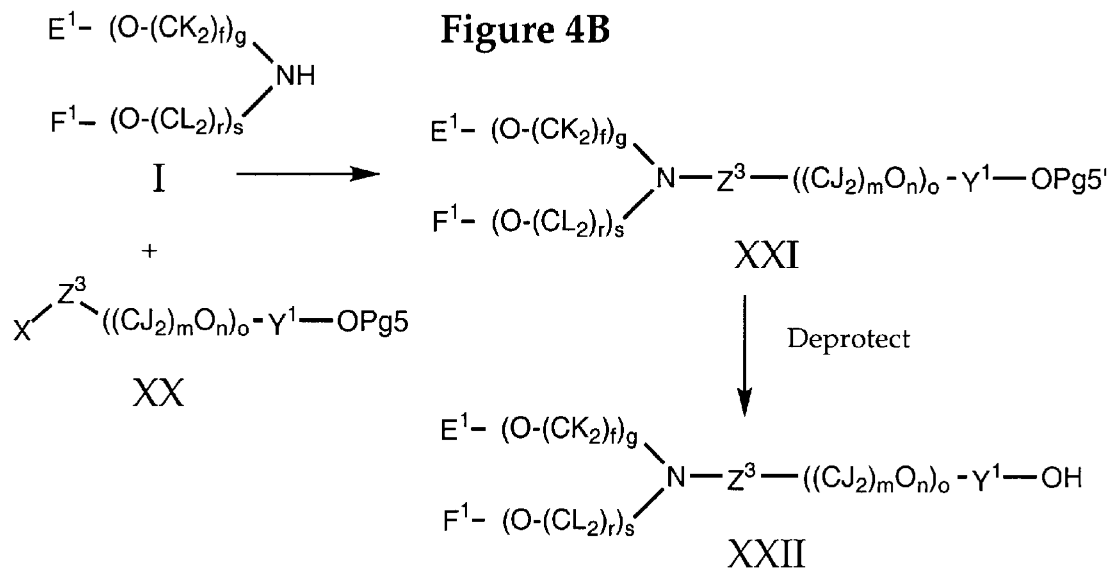

With reference to FIG. 4B, a general synthetic method is presented for the preparation of other alcohols suitable for the practice of this invention. According to the method, a suitably protected sulfonyl halide XX is reacted with a secondary amine I to thereby form the protected sulfonamide XXI. The hydroxyl protecting group Pg5' is then removed to thereby generate the alcohol XXII. With reference to FIG. 4B, the moieties $E^1$, $F^1$, J, K, L, X, $Y^1$, $Z^3$, Pg5 and the numbers e, f, g, m, n, o, r, and s have been previously defined.

If one of the starting materials (i.e. I or XX) is liquid, this reaction may be performed without the addition of a solvent, provided care is taken when mixing the reagents. Alternatively, a non-nucleophilic solvent such as dichloromethane, diethylether, tetrahydrofuran, dioxane or N,N'-dimethylformamide can be used to mediate the reaction between components I and XX. Typically the secondary amine will be present in at least two equivalents to thereby act as a base to scavenge the acid formed by the reaction. Alternatively, a non-nucleophilic base such as triethylamine or N,N'-diisopropylethylamine may be added to neutralize the acid equivalent. Typically, the reaction will proceed at ambient temperature but may be heated if the reagents are slow to react.

iii. Branched Alkyl Halide Compositions

Branched alkyl halides can likewise be used to modify peptides and PNAs during chemical assembly. Preferably the branched alkyl halide is a simple, branched alkyl halide. Typically, polymer modification will occur by reaction of the halide functional group with a nucleophilic functional group (preferably, a primary amine, secondary amine or thiol) of the polymer in the presence of a non-nucleophilic base (e.g. triethylamine or N,N-diisopropylethylamine) at ambient or elevated temperature. The reaction of a alkyl halide with an amino functional group of the polymer will generate a secondary or tertiary amine in the polymer which will be positively charged at physiological pH.

Alkyl halides suitable for the practice of this invention can be prepared by converting the Hydroxyl Compositions described in subsection ii, above, to alkyl halides by known methods. Consequently, alkyl halides suitable for the practice of this invention have the general formula:

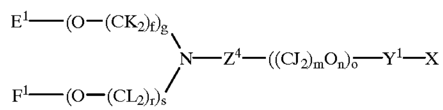

A used herein, the moieties $E^1$, $F^1$, J, K, L, X, $Y^1$ and $Z^4$ and the numbers f, g, m, n, o, r and s have been previously described.

Suitably Protected Multiply Branched Amino Acid Synthons

As previously discussed under the subheading "PNA, Peptide and Polyamide Labeling or Modification", a preferred method for modifying polymers (including polyamides, peptide and PNA) with the branched or multiply branched solubility enhancing compositions of this invention is by way of the production of suitably protected multiply branched amino acid synthons which can be used with standard synthesis methodologies. Therefore, preferred compositions of this invention will include suitably protected amino acid derivatives wherein an amino functional group is protected with a protecting group which can be utilized in the chemical synthesis of polyamides, peptides and particularly PNAs. Non-limiting examples of suitable protecting groups include N-(tert-butyloxycarbonyl, a.k.a. "t-boc") and N-(Fluorenylmethoxycarbonyl, a.k.a. "Fmoc").

All of the compositions described in subheadings "Branched Acid Compositions", "Branched Hydroxyl Compositions" and "Branched Alkyl Halide Compositions" are suitable for reaction with nucleophiles. Consequently, the solubility enhancing suitably protected multiply branched amino acid synthons of this invention will be typically prepared by reacting any of the aforementioned branched, simple branched, multiply branched or simple, multiply branched compositions with the nucleophilic functional group of a suitably protected amino acid.

In one preferred embodiment, a nucleophile of either a naturally occurring or non-naturally occurring Fmoc amino acid is reacted with any of the aforementioned branched, simple branched, multiply branched or simple, multiply branched compositions to thereby prepare a multiply branched Fmoc amino acid synthon. Preferred compositions are described under subheadings "Branched Acid Compositions", "Branched Hydroxyl Compositions" and "Branched Alkyl Halide Compositions". A preferred amino acid is N-α-Fmoc-L-Lysine-OH to which the Branched Acid Composition, Branched Hydroxyl Composition or Branched Alkyl Halide Composition is linked with the N-ε-amino group using well known methodologies.

Another preferred Fmoc protected amino acid is the non-natural N-[N'-fluorenylmethyloxycarbonyl-(2'-aminoethyl)]glycine (a.k.a. Fmoc-aeg-OH), wherein the Branched Acid Composition, Branched Hydroxyl Composition or Branched Alkyl Halide Composition is linked to the aza nitrogen of the amino acid using well known methodologies. With reference to FIGS. 3A and 3B, compounds 13 (a.k.a. Fmoc-"E"aeg-OH) and 18 (ak.a. Fmoc-"+"aeg-OH) are exemplary multiply branched Fmoc amino acid synthons useful for the practice of this invention.

Preferred multiply branched amino acid synthons suitable for modifying peptides, peptide nucleic acids and other polyamides are compounds having the general formula:

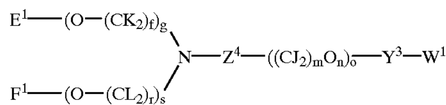

As used herein, the moieties $E^1$, $F^1$, J, K, L, and $Z^4$ have been previously described. The moiety $W^1$ is selected from the group consisting of: —Q, —C(O)Q, —C(S)Q and —$S(O_2)$Q. The moiety $Y^3$ is selected from the group consisting of a bond and a group having the formula: —$(CI_2)_e$—, wherein e is a whole number from 1 to 10, provided however that if $Y^3$ is a bond, $W^1$ is selected from the group consisting of: —C(O)Q, —C(S)Q, and —$S(O_2)$Q. Each moiety Q is a suitably protected amino acid moiety. Preferably Q is a suitably protected amino acid selected from the group consisting of:

1. a protected or unprotected naturally occurring amino acid, linked to either of the N-α-amino group or to the nucleophilic functional group of a side chain of the amino acid;
2. a protected or unprotected unnatural amino acid comprising a amino group for polymer extension as well as a second nucleophile to which is linked a modifying moiety such as a Branched Acid Composition, a Branched Hydroxyl Composition or a Branched Alkyl Halide Composition; and
3. a group having the formula:

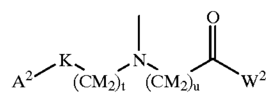

wherein, each moiety $A^2$ is selected from the group consisting of H and Pg6. Each moiety K is selected from the group consisting of: O, S, NH and $NR^3$. Each moiety $W^2$ is selected from the group consisting of: —X, —OH, —$OR^3$, and an active ester. Each moiety M is the same or different and is selected from the group consisting of: H, $R^3$, $OR^3$, $SR^3$, $NHR^3$, $NR^3_2$, F, Cl Br and I. Each moiety $R^3$ is the same or different and is an alkyl group having one to five carbon atoms which may optionally contain a heteroatom or a substituted or unsubstituted aryl group. Each number t is 1, 2 or 3 and each number u is 1, 2 or 3.

The moiety represented by Pg6 is a heteroatom protecting group. The heteroatom protecting group will be chosen so that it is compatible with the polymer synthesis. Those of ordinary skill in the art of polyamide synthesis, peptide synthesis or PNA synthesis will recognize suitable protecting groups. Preferably, Pg6 is a protecting group selected from the group consisting of tert-butyloxycarbonyl (t-boc), benzhydroloxycarbonyl (Bhoc) and fluorenylmethoxycarbonyl (Fmoc).

An active ester, as known in the art of polyamide synthesis and peptide synthesis, is an ester which has been activated toward nucleophilic displacement as compared with an ordinary ester. Non-limiting examples include, N-hydroxysuccinimidyl esters, pentafluorophenyl esters hydroxybenzotriazole esters, and hydroxyazabenzotriazole esters.

In a preferred embodiment, Q is a suitably protected amino acid having the general formula:

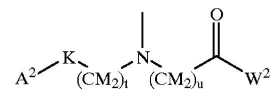

wherein, the moiety K is selected from the group consisting of: O, S and NH, the moiety $W^2$ is —X or —OH and each M is the same or different and is H, $R^3$, $OR^3$, F, Cl, Br or I. The moiety $A^2$ has been previously defined. In a more preferred embodiment, $A^2$ is Pg6, K is NH and each M is H. In a most preferred embodiment, t is 2 and u is 1, thereby producing an N-[2-(aminoethyl)]glycine "aeg" based synthon having an achiral backbone. Preferred "aeg" synthons possess an amino group protected with fluorenylmethoxycarbonyl (Fmoc) and a free carboxylic acid group (i.e. W is —OH). The carboxylic acid then typically activated on-line during the automated condensation with the polymer (e.g. polyamide, peptide or PNA) being assembled.

In other preferred embodiments, $Z^4$ is —C(O)— and $Y^3$ is —$(CI_2)_e$—. Additional preferences include each I and J as H, e as 1, m as 1, n as 1, and o is 1. Alternatively, it is preferred that each K and L are H, f is 2, r is 2, g is 1 and s is 1. The moiety $E^1$ is preferably —$CH_3$ and the moiety $F^1$ is preferably —$CH_3$.

A most preferred suitably protected, achiral, non-nucleophilic, multiply branched amino acid synthon is compound 13 (Fmoc-"E"aeg-OH) as illustrated in FIG. 3A.

In other preferred embodiments of the modifying moiety attached to the suitably protected amino acid, $Z^4$ is a single bond, o is 0 and $Y^3$ is —$(CI_2)_e$—. Additional preferences include each I as H and e is 1. Alternatively, it is also preferred that each K and L are H, f is 2, r is 2, g is 1 and s is 1. The moiety $E^1$ is preferably —$CH_3$ and the moiety $F^1$ is preferably —$CH_3$.

Another most preferred suitably protected, achiral, non-nucleophilic, zwitterionic amino acid synthon is compound 18 (Fmoc-"+"aeg-OH) as illustrated in FIG. 3B.

In still another preferred embodiment, Q is a naturally occurring N-α-Fmoc amino acid, wherein the modifying moiety:

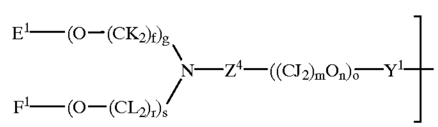

is linked to the side chain of the N-α-Fmoc amino acid. As used herein, the moieties $E^1$, $F^1$, J, K, L, $Y^1$, $Z^4$ and the numbers e, f, g, m, n, o, r and s have been previously descnbed. Preferably, the modifying moiety is linked to the ε-amino group of lysine, the hydroxyl group of serine or threonine or the thiol group of cystine.

Methods of this Invention

In another embodiment, this invention pertains to methods for improving the solubility of synthetic polymers and particularly PNA oligomers. The method comprises reacting a polymer, a functional group of a subunit of a polymer or a synthesis support upon which a synthetic polymer is to be assembled, with one or more branched compositions, simple branched compositions, multiply branched compositions (e.g. a Branched Acid Composition, a Branched Hydroxyl Composition or a Branched Alkyl Halide Composition), simple multiply branched compositions (including synthons) which are useful for improving the solubility of synthetic polymers and/or which can minimize or eliminate polymer self-aggregation. Preferred branched compositions and multiply branched compositions or synthons which are particularly well suited for modifying nucleic acids and nucleic acid analogs according to the method of this invention have been previously described herein. Preferred branched compositions and multiply branched compositions which are particularly well suited for modifying peptides, PNAs and other polyamides according to the method of this invention have been previously described herein.

PNAs, Peptides and Polyamides of this Invention

Applicants have used the compositions and/or methods described herein to prepare synthetic polymers, and particularly PNA oligomers, comprising one or more modifying moieties suitable for enhancing the solubility of the synthetic polymer and/or which minimize or eliminate polymer self-aggregation as compared with the unmodified polymer. The modified synthetic polymers may be labeled with detectable moieties or may be unlabeled. The modified synthetic polymers may also exist immobilized to supports, as lyophilized powders or be dissolved or suspended in solution.

Using the compositions of this invention, applicants have prepared modified PNAs, and particularly purine-rich PNAs, which are generally more easily purified and characterized than are the unmodified polymers. Moreover, several of the polymers prepared by applicants are compositions which the art teaches to be difficult or impossible to purify or characterize as a consequence of the nucleobase sequence of the polymer. Examples of "impossible" polymers prepared by applicants are listed in Table 1 of the Examples section of this specification. The examples submitted by applicants are generally purified, labeled polymers wherein the modifying moieties are uncharged or positively charged at physiological pH, non-nucleophilic and achiral. Exemplary PNA polymer synthesis and modification are described in detail in the Examples section of this specification.

Figure 9:
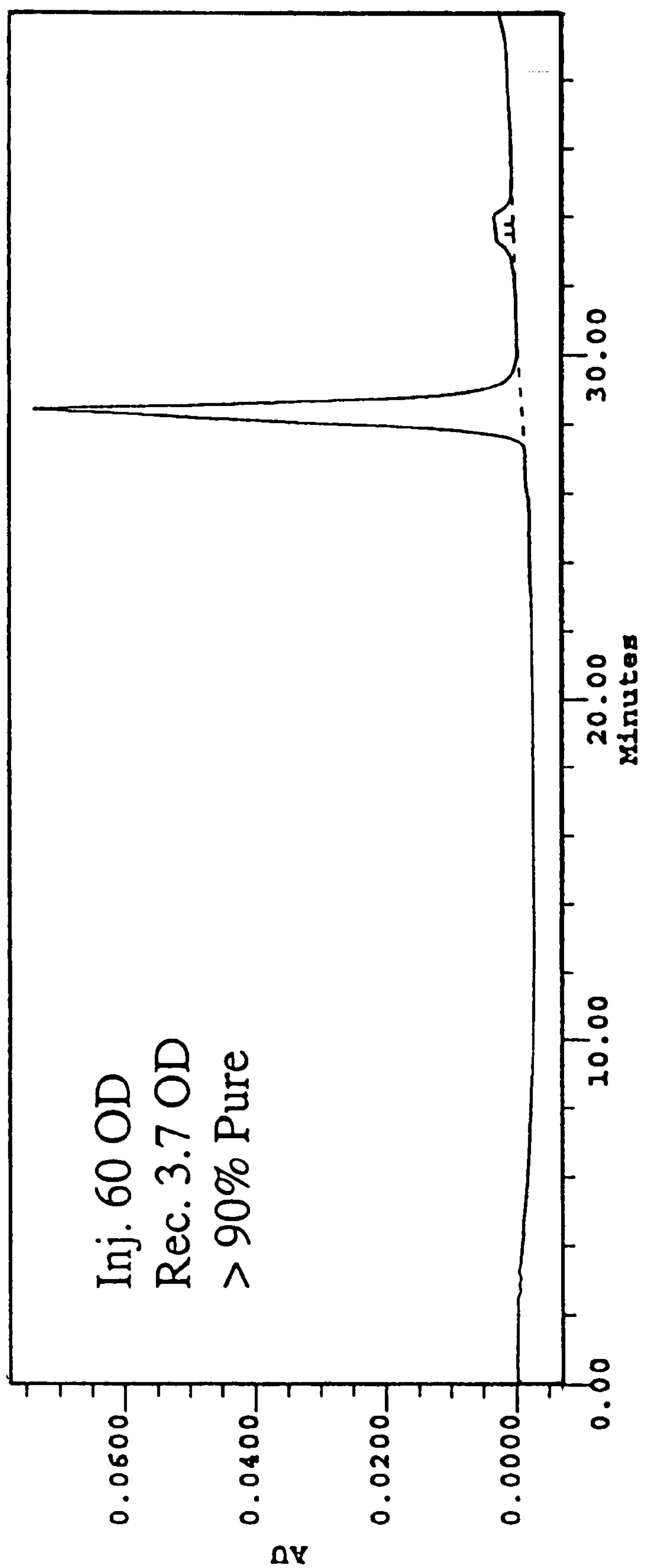
FIG. 9 is an HPLC chromatogram of a soluble, purified (>90%), labeled, homopurine 15-mer PNA oligomer.

This invention also pertains to purified PNA oligomers having a purine nucleobase content of 75% or greater in a PNA oligomer having 8 or more nucleobases, preferably 10 or more nucleobases and most preferably 13 or more nucleobases. This invention additionally relates to purified, labeled or unlabeled PNA oligomers having 6 or more sequential purine nucleobases, preferably 8 or more sequential nucleobases and most preferably 10 or more sequential purine nucleobases (See: FIG. 9 and Table 1). With reference to Table 1, applicants, have successfully purified and characterized PNA oligomers having a purine nucleobase content of greater than 85% in PNA oligomers having 12 or more nucleobases. As an extreme example of a purine-rich PNA oligomer, this invention relates to purified, labeled or unlabeled, homopurine PNA oligomers comprising 6 or more nucleobases, preferably 10 or more nucleobases and most preferably 13 or more nucleobases (See: FIG. 9 and Table 1). With reference to Table 1, applicants demonstrate the successful preparation, purification and characterization of a purified, labeled, homopurine PNA having as many as 15 nucleobases.

Figure 8:
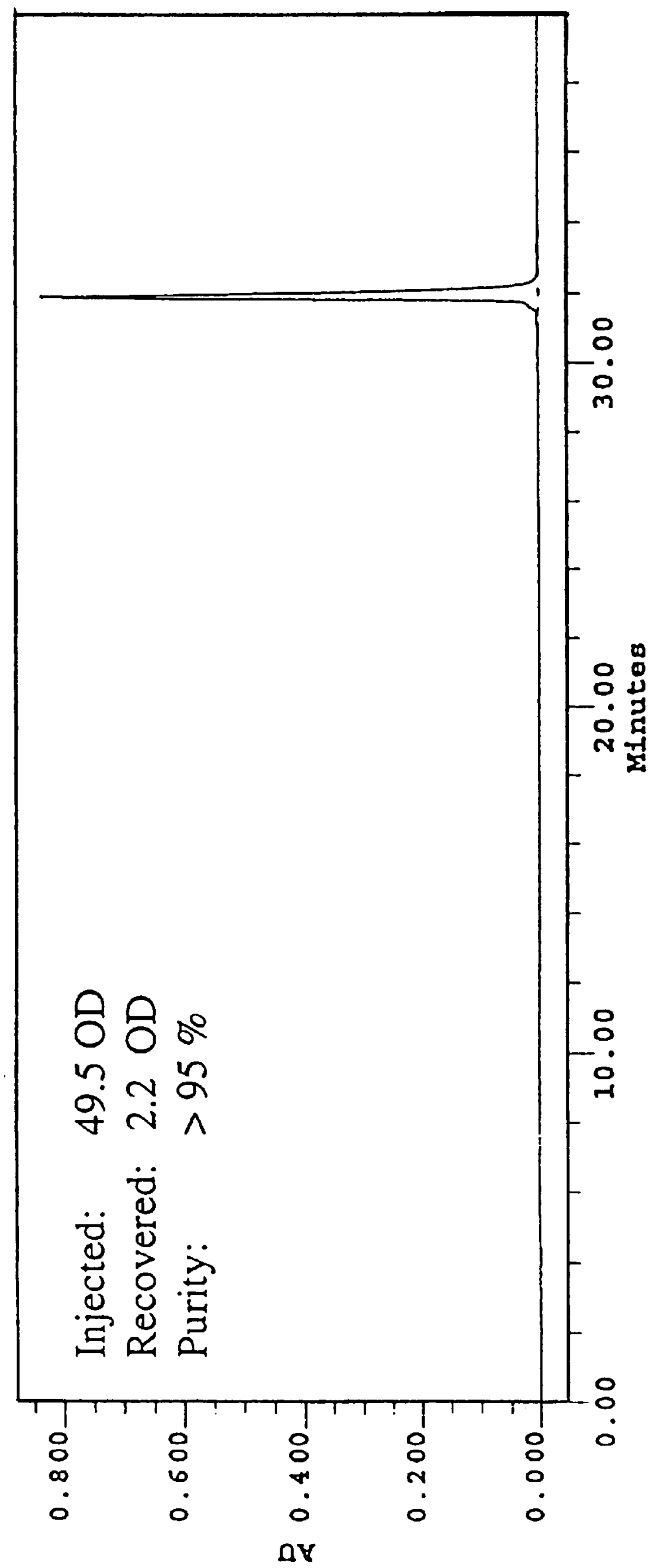
FIG. 8 is an HPLC chromatogram of a soluble, labeled highly purified Homo G PNA oligomer.

Likewise, this invention also relates to purified, unlabeled or labeled, modified, PNA oligomers having four or more sequential G residues (nucleobases) in a PNA oligomer having 6 or more nucleobases, preferably 10 or more nucleobases and most preferably 13 or more nucleobases (See: FIG. 8 and Table 1). One exemplary PNA is a labeled 7-mer homo G polymer which is highly pure (See: FIG. 8).

Figure 6:
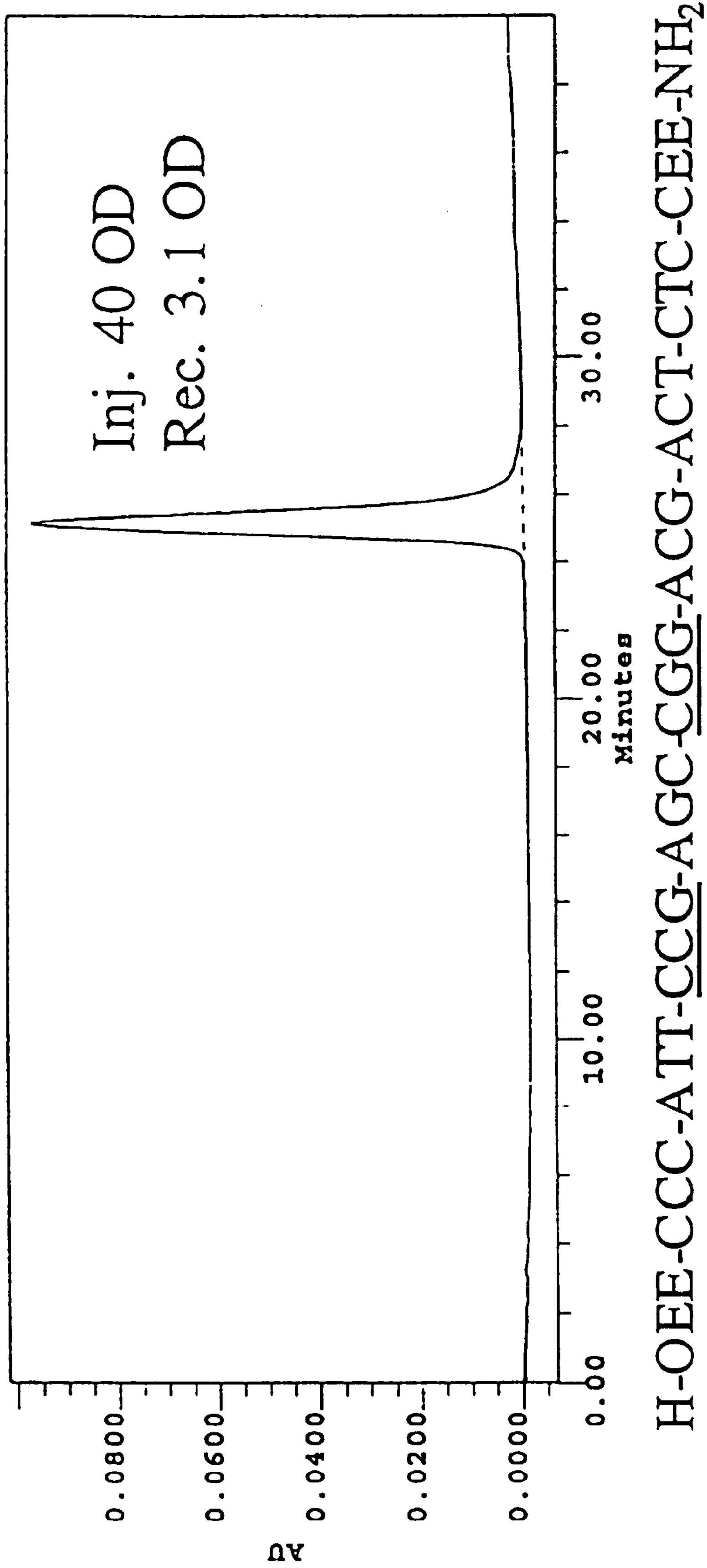
FIG. 6 is an HPLC chromatogram of a purified PNA oligomer comprising 25 nucleobases.

In yet another embodiment, this invention pertains to purified, modified PNA oligomers comprising greater than 20 nucleobases, preferably greater than 23 nucleobases and most preferably more than 25 nucleobases. As an illustration, one PNA oligomer having 25 nucleobases was prepared (See: FIG. 6). In addition to extreme length, this PNA oligomer contained a 3 base pair "bp" region of inherent self-complementary (See: underlined nucleobases in FIG. 6). Regions of self-complementary are known to result in polymer self-aggregation and this characteristic has been previously identified as a property which inhibits proper purification and characterization of PNA oligomers. Despite the extreme length and region of self-complementary, the presence of the solubility enhancing moieties of this invention, when incorporated into this PNA oligomer, enabled a remarkable recovery of the PNA oligomer which was greater than 90% pure.

As used herein, purified PNA oligomers which are at least 80% pure as determined by the chromatographic methods are outlined in Example 13, Gradient A. Preferably, the PNAs are greater than 90% pure and most preferably the PNAs are greater than 95% pure by analysis.

In yet another embodiment, this invention pertains to highly soluble PNA oligomers comprising 20 or more nucleobases and one or more hydrophobic labels (e.g. fluorescein and rhodamine). As used herein "hydrophobic label (s)" shall mean detectable moiety(ies) comprising at least two linked aromatic rings. By "highly soluble" we mean that the polymer or PNA oligomer is soluble at concentrations of at least 7.5 $\mu$M/L of aqueous buffer containing no organic modifier (See: Example 18 of this specification).

The preferred polymers (including polyamide, peptide and PNA oligomers) of this invention will comprise one or more modifying moieties having the formula:

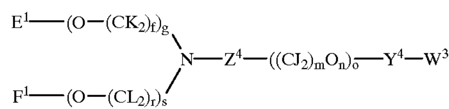

which are linked to the polymer. The moieties $E^1$, $F^1$, J, K, L and $Z^4$ and the numbers have f, g, m, n, o, r and s have been previously defined. The moiety $W^3$ is selected from the group consisting of: $—Q^2$, $—C(O)Q^2$, $—C(S)Q^2$, and $—S(O_2)Q^2$. The moiety $Y^4$ is selected from the group consisting of a bond and a group having the formula: $—(CI_2)_e—$, wherein e is a whole number from 1 to 10, provided however that if $Y^4$ is a bond, then $W^3$ is selected from the group consisting of: $—C(O)Q^2$, $—C(S)Q^2$, and $—S(O_2)Q^2$. The moiety $Q^2$ is the link or bond to a subunit of the synthetic polymer.

The polymer may be a nucleic acid, nucleic acid analog, polyamide, a peptide, a peptide nucleic acid (PNA), a chimera or linked polymer, but preferably the synthetic polymer is a peptide nucleic acid (PNA). When present in the modified polymer of this invention, the modifying moiety may be charged or uncharged (at physiological pH), nucleophilic or non-nucleophilic and chiral or achiral. In one preferred embodiment, the modifying moiety is achiral, non-nucleophilic and uncharged (at physiological pH). In a second preferred embodiment, the modifying moiety is positively charged (at physiological pH), non-nucleophilic and achiral. In a third preferred embodiment, the modifying moiety is uncharged, achiral and contains only hydroxyl groups as nucleophiles.

For example, PNAs which were modified with one or more of the uncharged, achiral, non-nucleophilic "E" moieties exhibited remarkable improvements in solubility and reduction in polymer self-aggregation. Several of the "E" modified PNAs prepared by applicants were purine-rich and N-terminally labeled with the hydrophobic label, 5(6)-carboxyfluorescein. The solubility and other characteristics of these probes were truly remarkable since the backbone, nucleobases and termini of these polymers were completely without charge at physiological pH and the entire polymer was achiral. Similarly, PNAs which were modified with one or more of the positively charged (physiological pH), achiral, non-nucleophilic "+" moieties exhibited remarkable improvements in solubility and reduction in polymer self-aggregation as compared with the unmodified polymer.

Preferred uncharged modifying moieties of this invention comprise a moiety $Z^4$ which is limited to the groups —C(O)—, —C(S)— or —$S(O_2)$—, and a moiety $W^3$ which is limited to the groups —$C(O)Q^2$, —$C(S)Q^2$, or —$S(O_2)Q^2$. Other preferred uncharged, non-nucleophilic modifying moieties of this invention comprise a moiety $Z^4$ which is limited to the groups —C(O)—, —C(S)— or —$S(O_2)$—, a moiety $W^3$ which is limited to the groups —$C(O)Q^2$, —$C(S)Q^2$, or —$S(O_2)Q^2$, a moiety $E^1$ which is limited to $R^1$ and a moiety $F^1$ which is limited to $R^1$. In more preferred embodiments, the moiety $Z^4$ is —C(O)—, $Y^4$ is —$(CI_2)_e$—, wherein e is 1 or 2, $W^3$ is —$C(O)Q^2$, o is 1 or 2, n is 1, each f, g, m, r and s is independently 1 or 2 and each I, J, K and L is H.

When modifying PNAs it is preferable to use suitably protected amino acids which will maintain the spacing between nucleobases. Preferred modifying moieties can be inserted within the polymer without disrupting the nucleobase spacing and thereby, presumably, not alter the hybridization efficiency of the oligomer to a target nucleic acid. It is also preferable to chose multiply branched amino acids synthons which do not possess a chiral center since it is known that chiral amino acids can affect the hybridization properties of a PNA probe (See: Lee, Morse & Olsvik, *Nucleic Acid Amplification Technologies: Application to Disease Diagnositics*, Chapter 3 by Ørum et al., BioTechniques Book Div. of Eaton Publishing (1997) pp. 29–48, at p. 33, ln. 4, to p. 34, ln. 12). Consequently, preferred modifying moieties of this invention are typically linked to a subunit of a polyamide, and preferably a PNA, wherein the polymer subunit has the formula:

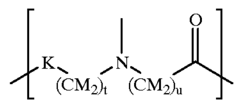

wherein, K is O, S, NH or $NR^3$, each M is the same or different and is H, $R^3$, $OR^3$, $SR^3$, $NHR^3$, $NR^3_2$, F, Cl, Br or I provided that the choice of each M does not induce chirality; wherein each $R^3$ is the same or different and is an alkyl group having one to five carbon atoms which may optionally contain a heteroatom or a substituted or unsubstituted aryl group, each t is 1, 2 or 3; and each u is 1, 2 or 3. In preferred embodiments, K is NH, each M is H, t is 2 and u is 1.

In one preferred embodiment, the polymers of this invention comprise one or more, non-nucleophilic, achiral and positively charged (physiological pH) modified subunits (herein identified as "+") having the formula:

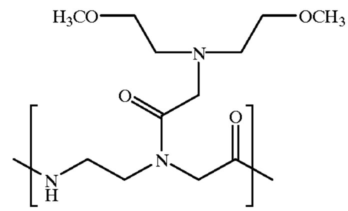

In another preferred embodiment, the polymers of this invention comprise one or more, non-nucleophilic, uncharged, and achiral modified subunits (herein identified as "E") having the formula:

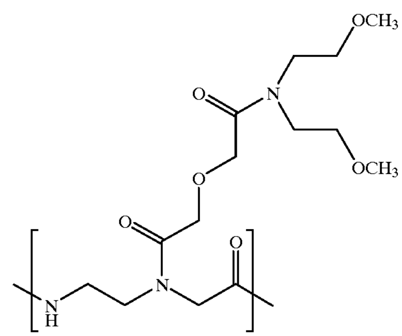

The modified polymers of this invention will comprise at least one modified moiety, but will preferably comprise more than one modifying moiety. In one preferred configuration a modified moiety is linked to the terminus of the polymer. In a second preferred configuration, two modified moieties are linked to the same terminus of the polymer. In a third preferred configuration, a modified moiety is linked to each end of the polymer to thereby flank the nucleobase sequence of the polymer. In yet a fourth preferred configuration, two modified moieties are linked into each terminus of the polymer to thereby flank the nucleobase sequence. The number of modified moieties linked to the polymer will be inversely proportional with the solubility of the polymer. For example, the more insoluble the polymer, a greater number of modifying moieties should be linked to the polymer whereas the more soluble the polymer the fewer modifying moieties need be linked to the polymer.

Polyamides on Surfaces/Arrays:

In certain embodiments the modified synthetic polymer is immobilized to a support. Support bound synthetic polymers may exist as fully protected or partially protected polymers which have been assembled but not yet cleaved from the synthesis support. Using supports of suitable design it is also possible to deprotect the polymer on the synthesis support without cleaving the linkage to the support (See: Weiler et al., *Nucl. Acids Res.* 25: 2792–2799 (1997)). Polymers are often synthesized on supports to which there are to be permanently linked so that they can be repetitively treated with samples of interest.

Alternatively, the polymers may be purified and then reimmobilized to a support. Prepurification of the polymers will generally provided greater specificity when samples of interest are repetitively allowed to interact with the support. (See: Lester et al., Poster Presented at the Biochip Technologies Conference in Annapolis, October, 1997). Conditions suitable for the immobilization of a PNA or peptide to a surface will generally be similar to those conditions described above for the solution-phase modification of a peptide or PNA. The immobilization reaction is essentially the equivalent of labeling the polymer whereby the label is substituted with the surface to which the polymer is to be covalently immobilized. In preferred embodiments of this invention, the surfaces comprising tresyl groups which are reacted with either of the terminal amino group of the polyamide or with an arylamine modified polymer.

Arrays are surfaces to which two or more known compositions of interest have been immobilized at a predefined position. The process by which the array is exposed to one or more samples of interest to thereby examine the interaction of components of the sample with the support bound compounds is a process called screening. The screening of libraries for compounds of diagnostic or therapeutic utility is currently of great scientific interest. Arrays or synthetic libraries comprising two or more synthetic polymers (e.g. modified PNA oligomers) which are modified with branched or multiply branched modifying moieties as described herein is still another embodiment of this invention. In a preferred embodiment, the array of this invention comprises two or more polyamides, and particularly PNA oligomers, which have been modified with one or more of the Branched Acid Compositions, Branched Hydroxyl Compositions, Branched Alkyl Halide Compositions and/or Multiply Branched Suitably Protected Amino Acid Compositions described herein.

Still another preferred embodiment of this invention pertains to surfaces comprising synthetic polymers which comprise a modifying moiety having the formula:

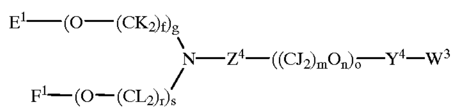

wherein, the moieties $E^1$, $F^1$, J, K, L $W^3$, $Y^4$, $Z^4$ and the numbers e, f, g, m, n, o, r and s have been previously defined. The other preferred embodiments described under subheading "PNAs, Peptides and Polyamides of this Invention" shall also apply to support bound polymers of this invention.

Kits of the Invention

In still another embodiment, the compositions of this invention may also be offered in a kit or the methods used in combination with a kit. Preferred kits of this invention will comprise branched or multiply branched synthons so that one of ordinary skill in the art may easily utilize them during chemical assembly to thereby modify a synthetic polymer. Other preferred kits of this invention will comprise polymers which have been modified with one or more branched or multiply branched moieties described herein to thereby improve aqueous solubility of the polymer and/or decrease or eliminate polymer self-aggregation. Preferably, the kits comprise simple branched or simple multiply branched compositions or polymers modified with the simple branched or simple multiply branched compositions described herein.

Consequently, in another embodiment this invention relates to kits comprising compositions which modify synthetic polymers. The kit-based compositions of this invention shall preferably be suitable for direct use in the chemical assembly of the polymer whether or not an automated instrument is utilized. Therefore, the kits of this invention may comprise one or more of the Branched Acid Compositions, Branched Hydroxyl Compositions, Branched Alkyl Halide Compositions or Suitably Protected Multiply Branched Amino Acid Synthons described previously. Preferred kits of this invention will comprise Fmoc-"E"aeg-OH and/or Fmoc-"+"aeg-OH. Alternatively, preferred kits shall comprise a synthesis support to which a Suitably Protected Multiply Branched Amino Acid Synthon (e.g. Fmoc-"E"aeg-OH and/or Fmoc-"+"aeg-OH) or a modified nucleic add, nucleic acid analog, peptide, polyamide or PNA or this invention has been covalently linked.

Consequently, when using the compositions, kits and/or methods described herein, it is now possible to routinely purify and characterize both labeled and unlabeled, modified PNA oligomers having a purine content of 75% or greater. Additionally, it is now possible to routinely purify and characterize both labeled and unlabeled, modified PNA oligomers having four or more sequential G residues. Furthermore, it is now possible to routinely purify and characterize labeled and unlabeled, modified PNA oligomers having 6 or more sequential purine residues, including homopurine PNAs of at least 15 residues in length. Guided by the teachings set forth herein, those of ordinary skill in the art will appreciate that the possession and/or practice of the embodiments of this invention will afford important features and advantages not presently known but which shall improve the state of the art.

EXAMPLES

Example 1

Synthesis of bis-(2-methoxyethyl)amidyl-diglycolic acid 12

To 60 mmol of bis(2-methoxyethyl)amine 1 (Aldrich Chemical), 65 mmol triethylamine and 40 mL of dichloromethane (DCM) was added portionwise 50 mmol of diglycolic anhydride 11 (Aldrich Chemical). The reaction was immediate and violent but was allowed to stir overnight. The reaction was worked up by evaporation to a brown oil. The residue was redissolved in 50 mL of DCM and then transferred to a separatory funnel. The DCM layer was extracted with 100 mL of 10% aqueous citric acid. The aqueous layer was then back extracted 5×25 mL of DCM. All DCM layers were combined and extracted 1× with 25 mL of 10% aqueous citric acid. The DCM layer was separated, dried ($Na_2SO_4$), filtered and evaporated to yield 6.6 g (26.5 mmol; 53% yield).

Large Scale:

To 500 mmol of diglycolic anhydride stirring in 800 mL of dichloromethane (DCM) was added dropwise, 1.1 mole of bis(2-methoxyethyl)amine 1 (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried ($Na_2SO_4$), filtered and evaporated to yield 73.8 g (296 mmole; 59% yield). A kugelrorh was then used to remove traces of solvent (product was heated to 60° C. at approximately 180 $\mu$M Hg).

Example 2

Synthesis of N-[N"-Fmoc-(2"-aminoethyl)]-N-[N, N'-(2-methoxyethyl)amidyl-diglycolyl]glycine (Fmoc-"E"aeg-OH) 13

To 8 mmol of Fmoc-aeg-OH (PerSeptive Biosystems, Inc.) was added 24 mL of acetone and 40 mL of MilliQ water. To this stirring solution was added 16 mmol of $NaHCO_3$ and 8 mmol of $K_2CO_3$. This solution was allowed to stir until all the Fmoc-aeg-OH had dissolved (approx. 1 hr.) and then the solution prepared, as described below, was added.

To 9 mmol of bis-(2-methoxyethyl)amidyl-diglycolic acid 12 was added 20 mL of anhydrous acetonitrile (Fluka Chemical), 27 mmol of N-methylmorpholine (NMM; Fluka Chemical) and 9.3 mmol of trimethylacetyl chloride (Aldrich Chemical). The solution was allowed to stir at room temperature for 30 minutes and then added dropwise to the solution of Fmoc-aeg-OH which was prepared as described above.

After the combined solutions stirred for 1 hr and tlc analysis indicated complete reaction, the organic solvents were removed by vacuum evaporation. The remaining aqueous solution was then acidified to pH 4.5 by the portionwise addition of citric acid. The solution was then transferred to a separatory funnel and extracted 4× with 35 mL of ethyl acetate. The combined ethyl acetate layers were then added to the separatory funnel. To the contents was added 4 mL of NMM and 35 mL of water. The contents of the separatory funnel were mixed and the aqueous layer collected after separation. The ethyl acetate layer was washed 1× with 10 mL of water. The water layers were combined and acidified to pH<3 by portionwise addition of citric acid. This aqueous solution was then extracted 3× with 35 mL of ethyl acetate with all ethyl acetate layers being combined, dried ($Na_2SO_4$), filtered and evaporated to yield 5.6 g white foam.

This crude product was, twice, dissolved in DCM and then precipitated into a mixture of 2/1 hexane/diethyl ether. The precipitation was performed twice to remove all traces of trimethylacetic (pivalic) acid. The final product was collected by vacuum filtration. Yield 2.67 g (4.7 mmol; 58%).

For larger scale syntheses, the precipitation procedure described above did not remove substantially all of the trimethylacetic (pivalic) acid. Thus, for larger scales the crude product was dissolved in a solution containing approximately thirty percent acetonitrile. This solution was then chromatographed on reversed phase silica gel using an acetonitrile gradient to elute the product. The pivalic acid will elute before the product and the presence of pivalic acid in the column eluent can be monitored by smell.

Example 3

Synthesis of N,N'-(2-methoxyethyl)-glycine-tert-butyl ester 16

To 75 mmol of bis(2-methoxyethyl)amine 1 (Aldrich Chemical) was added 75 mmol of tert-butyl chloroacetate 14 (Aldrich Chemical). The reaction was allowed to stir overnight. $^1$H-MNR analysis indicated the reaction was approximately 75% complete in the morning. An additional 37.5 mmol of Bis(2-methoxyethyl)amine was added and the reaction was again allowed to stir overnight. $^1$H-MNR analysis indicated the reaction was greater than 75% complete in the morning. An additional 40 mmol of bis(2-methoxyethyl)amine was added and then the reaction was allowed to stir for an additional two days. Because the reaction appeared essentially complete by $^1$H-MNR analysis, it was then worked up.

To the reaction was added 50 mL of DCM and 50 mL of 5% aqueous sodium bicarbonate solution. To this stirring solution was added portionwise, 100 mmol of solid potassium carbonate ($K_2CO_3$). An additional 50 mL of DCM was then added and the heterogeneous solution was transferred to a separatory funnel. The layers were separated and the pH of the aqueous layer was determined to be approximately 11.5, by paper. The DCM layer was washed with 50 mL of 5% aqueous sodium bicarbonate and then 5 mL of water. The DCM layer was finally, dried ($Na_2SO_4$), filtered and evaporated to yield 17.2 g of a very thin red oil. This crude product was Kugelrorh distilled at 70–80° C. (200–500 $\mu$M Hg) to yield 16.3 g or a clear colorless oil (66 mmol; 88%).

Large Scale:

To 1.1 mole of bis(2-methoxyethyl)amine 1 (Aldrich Chemical) was added dropwise 500 mmol of tert-butyl chloroacetate 14 (Aldrich Chemical). The reaction was allowed to stir for three days and was then worked up.

To the final reaction contents was added 250 mL of DCM and 200 mL of water. To this stirring solution was added portionwise, 300 mmol of solid potassium carbonate ($K_2CO_3$). After completely mixing, the layers were separated. The DCM layer was washed once with a volume of water, dried ($Na_2SO_4$), filtered and evaporated to yield 66.3 g of a very thin yellow oil. This crude product was Kugelrorh distilled at 60° C. (200–500 $\mu$M Hg) to yield 58.9 g of a clear colorless oil (238 mmol; 95%).

Example 4

Synthesis of N,N'-(2-methoxyethyl)-glycine 17

To the purified (stirring) N,N'-(2-methoxyethyl)-glycine-tert-butyl ester 16 was slowly added 12.1 mL of concentrated hydrochloric acid. The reaction was allowed to stir overnight and then the byproducts (e.g. water, HCl, isobutylene) were removed by vacuum evaporation. $^1$H-MNR analysis indicated the t-butyl ester was hydrolyzed but it appeared that there was water and HCl still present. The crude product was co-evaporated 2× from ACN but water and HCl were still present.

To eliminate impurities, a 4.4 g sample was removed from the crude product and Kugelrorh distilled at 135–155° C. (100–200 $\mu$M Hg with rapidly dropping pressure after distillation began). Yield 4.2 g (18.4 mmol; 95% recovery of thick, clear, colorless oil). The distilled product did not contain any water or HCl.

Example 5

Synthesis of N-[N"-Fmoc-(2"-aminoethyl)]-N-[N,N'-(2-methoxyethyl)-glycyl]glycine (Fmoc-"+"aeg-OH) 18

To 8 mmol of Fmoc-aeg-OH (PerSeptive Biosystems, Inc.) was added 24 mL of acetone and 40 mL of MilliQ water. To this stirring solution was added 16 mmol of $NaHCO_3$ and 8 mmol of $K_2CO_3$. This solution was allowed to stir until all the Fmoc-aeg-OH had dissolved (approx. 1 hr.) and then the solution prepared as described below was added.

To 9 mmol of N,N'-[bis-(2-methoxyethyl])-glycine 17 was added 20 mL of anhydrous acetonitrile (Fluka Chemical), 9 mmol diisopropylethylamine (DIEA, Aldrich Chemical), 27 mmol of N-methylmorpholine (NMM; Fluka Chemical) and 9.3 mmol of trimethylacetyl chloride (Aldrich Chemical). The solution was allowed to stir at room temperature for 30 minutes and the added dropwise to the solution of Fmoc-aeg-OH which was prepared as described above.

After the combined solutions stirred for 1 hr and tlc analysis indicated complete reaction, the organic solvents were removed by vacuum evaporation. The remaining aqueous solution was then acidified to pH 7.0 by the portionwise addition of citric acid. The solution was then transferred to a separatory funnel and extracted 2× with 35 mL of ethyl acetate. No product was present in the organic layer so it was discarded.

The pH of the aqueous solution was then adjusted up and down until the solution got cloudy at approximately pH 8, by paper. The solvent was then transferred back to the separatory funnel and extracted with 25 mL of DCM. Because product was present in the organic layer, the aqueous layer was extracted again 3× with DCM. All DCM layers were combined and back extracted with 5% sodium bicarbonate solution. The pH was again adjusted to about pH 8.0. The aqueous layer was extracted several times with DCM and all DCM layers were combined, dried ($Na_2SO_4$), filtered and evaporated to yield approximately 5.0 g of a white solid.

This crude product was dissolved in DCM and precipitated into a mixture of 2/1 hexane/diethyl ether. The final product was collected by vacuum filtration. Yield 2.97 g (5.8 mmol; 72% yield)

Example 6

General Procedure for the Synthesis Of PAL-Peg/PS Synthesis Supports Suitable for Preparing Polyamides having C-Terminal Modifying Moieties The Fmoc-"E"aeg-OH and Fmoc-"+"aeg-OH synthons were used to prepare synthesis supports useful for the preparation of oligomers comprising one or more C-terminal "E" or "+" moieties. Though the Fmoc-"E"aeg-OH and Fmoc-"+"aeg-OH synthons can be, and in fact were from time to time, used directly in the automated instrument, the preparation of prederivatized supports is preferred because less synthon is required to prepare the bulk support.

In the first step, the fluorenylmethoxycarbonyl (Fmoc) group of commercially available Fmoc-PAL-Peg-PS synthesis support (PerSeptive Biosystems, Inc.; P/N GEN913384) was removed by treatment, in a flow through vessel, with 20% piperidine in N,N'-dimethylformamide (DMF) for 30 minutes. The support was then washed with DCM. Finally the support was washed with DMF and dried with a flushing stream of argon.

In the second step, a solution containing 0.15 M monomer (Fmoc-"E"aeg-OH or Fmoc-"+"aeg-OH), 0.14 M [O-(7-azabenzotriaol-1-yl)-1,1,3,3 tetramethyluronium hexafluorophosphate (HATU), 0.15 M DIEA and 0.225 2,6-lutidine in DMF was prepared by sequential combination of the reagents. This solution was then added to the synthesis support and allowed to react for 2 hours. The solution was then flushed through the vessel with a stream of argon and the support washed sequentially with DMF, DCM and DMF. The resin was then dried with a stream of argon.

In the third step, the support was the treated with 5 mL of standard commercially available PNA capping reagent (PerSeptive Biosystems, Inc., P/N GEN063102). The capping reagent was then flushed from the vessel and the support was washed with DMF and DCM. The support was then dried with a stream of argon.

For the support comprising two "E" moieties, the three step cycle was repeated. When the support was properly derivatized, it was dried under high vacuum. Final loading of the support was determined by analysis of Fmoc loading of three samples of approximately 6–8 mg.

This synthesis support was then packed into empty PNA synthesis column, as needed, and used to prepare PNA oligomers having C-terminal modifying moieties.

Example 7

Synthesis of N-α-(Fmoc)-N-ϵ-($NH_2$)-L-Lysine-OH

To 20 mmol of N-α-(Fmoc)-N-ϵ-(t-boc)-L-lysine-OH was added 60 mL of 2/1 dichloromethane (DCM)/trifluoroacetic acid (TFA). The solution was allowed to stir until the tert-butyloxycarbonyl (t-boc) group had completely been removed from the N-α-(Fmoc)-N-ϵ-(t-boc)-L-lysine-OH. The solution was then evaporated to dryness and the residue redissolved in 15 mL of DCM. An attempt was then made to precipitate the product by dropwise addition of the solution to 350 mL of ethyl ether. Because the product oiled out, the ethyl ether was decanted and the oil put under high vacuum to yield a white foam. The white foam was dissolved in 250 mL of water and the solution was neutralized to pH 4 by addition of saturated sodium phosphate (dibasic). A white solid formed and was collected by vacuum filtration. The product was dried in a vacuum oven at 35–40° C. overnight. Yield 17.6 mmol, 88%.

Example 8

Synthesis of N-α-(Fmoc)-N-ϵ-(dabcyl)-L-Lysine-OH

To 1 mmol of N-α-(Fmoc)-N-ϵ-($NH_2$)-L-Lysine-OH (Example 7) was added 5 mL of N,N'-dimethylformamide (DMF) and 1.1 mmol of TFA. This solution was allowed to stir until the amino acid had completely dissolved.

To 1.1 mmol of 4-((4-(dimethylamino)phenyl)azo) benzoic acid, succinimidyl ester (Dabcyl-NHS; Molecular Probes, P/N D-2245) was added 4 mL of DMF and 5 mmol of diisopropylethylamine (DIEA). To this stirring solution was added, dropwise, the N-α-(Fmoc)-N-ϵ-($NH_2$)-L-Lysine-OH solution prepared as described above. The reaction was allowed to stir overnight and was then worked up.

The solvent was vacuum evaporated and the residue partitioned in 50 mL of DCM and 50 mL of 10% aqueous citric acid. The layers were separated and the organic layer washed with aqueous sodium bicarbonate and again with 10% aqueous citric acid. The organic layer was then dried with sodium sulfate, filtered and evaporated to an orange foam. The foam was crystallized from acetonitrile (ACN) and the crystals collected by vacuum filtration. Yield 0.52 mmol, 52%.

Example 9

Synthesis of N-α-(Fmoc)-N-ϵ-(dabcyl)-L-Lysine-PAL-Peg/PS Synthesis Support

This synthesis support was used to label PNA probe P3 with dabcyl. The N-α-(Fmoc)-N-ϵ-(dabcyl)-L-Lysine-OH (Example 8) was used to prepare a synthesis support useful for the preparation of C-terminal dabcylated PNAs. The fluorenylmethoxycarbonyl (Fmoc) group of 0.824 g of commercially available Fmoc-PAL-Peg-PS synthesis support (PerSeptive Biosystems, Inc.; P/N GEN913384) was removed by treatment, in a flow through vessel, with 20% piperidine in DCM for 30 minutes. The support was then washed with DCM. Finally, the support was washed with DMF and dried with a flushing stream of argon.

A solution containing 0.302 g N-α-(Fmoc)-N-ϵ-(dabcyl)-L-Lysine-OH, 3.25 mL of DMF, 0.173 g [O-(7-azabenzotriaol-1-yl)-1,1,3,3-tetramethyluronium hexafluorophosphate (HATU), 0.101 mL DIEA and 0.068 mL 2,6-lutidine was prepared by sequential combination of the reagents. This solution was then added to the washed synthesis support and allowed to react for 2 hours. The solution was then flushed through the vessel with a stream of argon and the support washed sequentially with DMF, DCM and DMF. The resin was then dried with a stream of argon.

The support was the treated with 5 mL of standard commercially available PNA capping reagent (PerSeptive Biosystems, Inc., P/N GEN063102). The capping reagent was then flushed from the vessel and the support was washed with DMF and DCM. The support was then dried with a stream of argon. Finally, the synthesis support was dried under high vacuum.

Final loading of the support was determined by analysis of Fmoc loading of three samples of approximately 6–8 mg. Analysis determined the loading to be approximately 0.145 mmol/g.

This synthesis support was packed into an empty PNA synthesis column, as needed, and used to prepare PNA oligomers having a C-terminal dabcyl quenching moiety attached to the PNA oligomer through the ϵ-amino group of the L-lysine amino acid.

Example 10

Synthesis of PNAs

PNAs were synthesized using commercially available monomers and instrumentation obtained from PerSeptive Biosystems, Inc., except that the modifying monomers (i.e. Fmoc-"E"aeg-OH and Fmoc-"+"aeg-OH) and the prederivatized synthesis supports were prepared as described above. The C-terminal modifying moieties were generally introduced by synthesis using the above described prederivatized supports. Alternatively, the monomers were delivered to the synthesis column using conditions which were identical to those used for the commercially available PNA synthons. N-terminal modifying moieties were introduced using the standard conditions and synthetic cycles. Except for Cy3 and Cy5 labeled oligomers, PNAs possessing an N-terminal fluorescein or other modifying moieties were treated with the appropriate labeling reagents and linkers (as required) prior to cleavage from the synthesis support. Double coupling was liberally used to prepare the oligomers presented in Table 2.

Figure 5:
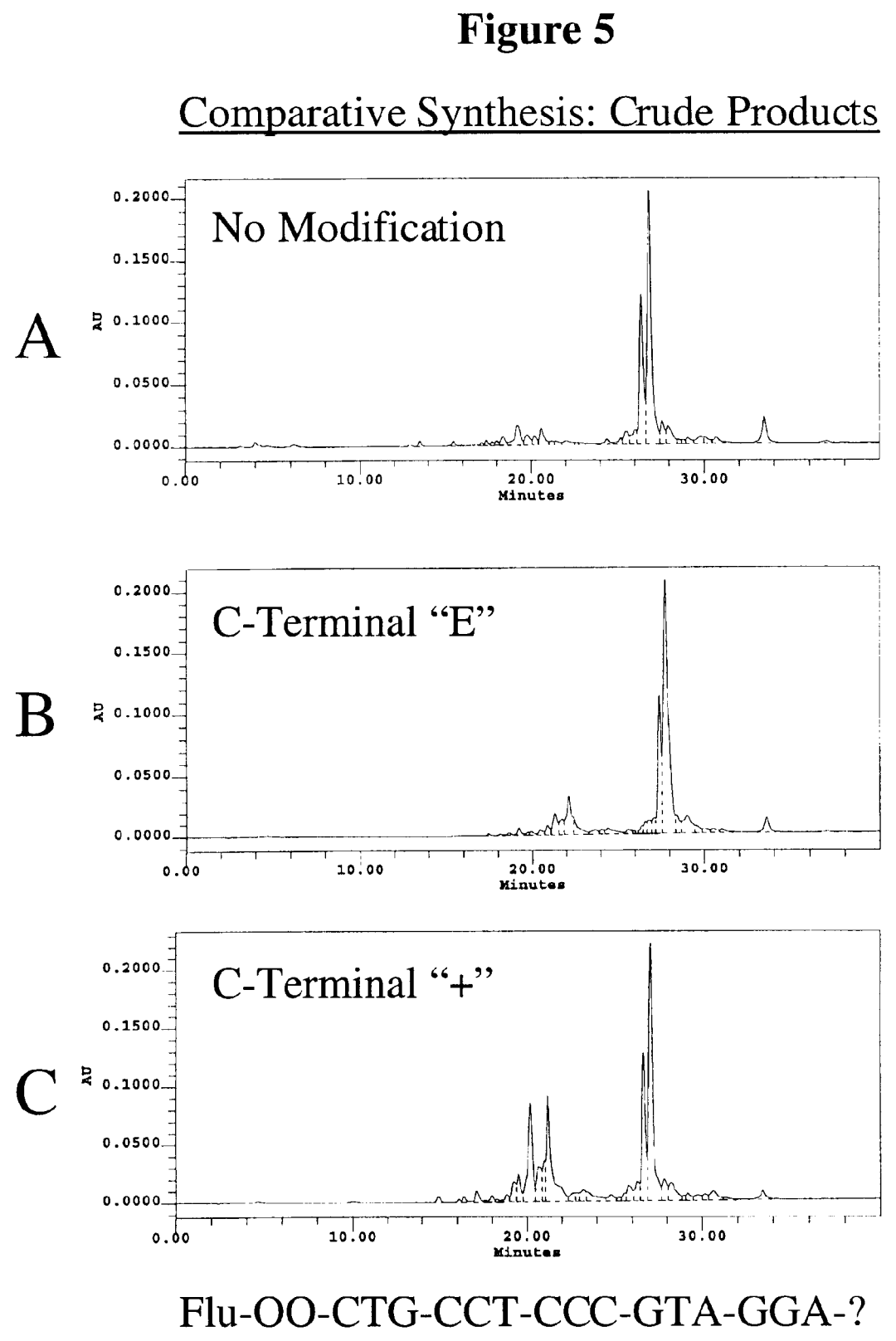

With reference to FIGS. 5A, 5B and 5C, the HPLC chromatograms of the crude products of an unmodified and two PNAs modified with "E" or "+" are illustrated. The nucleobase sequence is the same for all three PNA oligomers (i.e. Uni-Flu Sequence, Flu-OO-CTG-CCT-CCC-GTA-GGA-?; wherein ? is one or either "E", "+" or no modification). Moreover, the same set of chemicals and synthesis protocols were use for all three oligomers. The chromatograms are stacked for ease of comparison. The isomeric mix of 5 and 6 carboxyfluorescein is resolved under these chromatography conditions. It should be noted that the "E" and "+" modifications cause slight retention of the product on the chromatography column. Though the crude unmodified and "E" modified PNAs exhibited similar purity, the synthesis using the "+" resin was of significantly lower quality. This is not a result we have generally observed though the number or examples at this time is very limited. Nonetheless, in all cases the proper polymer was prepared.

Example 11A

General Procedure for N-terminal Labeling of Support Bound PNA with 5(6)carboxyfluorescein-NHS There are several methods available in the literature for modifying PNA with fluorescein. We find this method to be highly efficient and reproducible when using 5(6) carboxyfluorescein-NHS.

The amino terminal fluorenylmethoxycarbonyl (Fmoc) group of the fully assembled PNA oligomer was removed by piperidine treatment and the synthesis support was washed and dried under vacuum. The synthesis support was then treated for 4–5 hours at 30–37° C. with approximately 250–300 μL of a solution containing 0.1M 5(6) carboxyfluorescein-NHS Molecular Probes, P/N C-1311), 0.3M DIEA and 0.3M 2,6-lutidine (reagents concentrations can be reduced to 0.08M 5(6)carboxyfluorescein-NHS (Molecular Probes, P/N C-1311), 0.24M DIEA and 0.24M 2,6-lutidine without significantly altering the results). After treatment, the synthesis support was washed and dried under high vacuum. The PNA oligomer was then cleaved, deprotected and purified as described below.

Example 11B

General Procedure for Labeling of Support Bound PNA With 5(6)carboxyfluorescein

This procedure was used to label PNA probe P3 with 5(6)carboxyfluorescein. After proper reaction with linkers and removal of the terminal amine protecting group, the resin was treated with approximately 200–250 μL of a solution containing 0.5M 5(6)carboxyfluorescein, 0.5M N,N'-diisopropylcarbodiimide, 0.5M 1-hydroxy-7-azabenzotriazole (HOAt) in DMF (See: Weber et al., *Bioorganic & Medicinal Chemistry Letters*, 8: 597–600 (1998). After treatment the synthesis support was washed and dried under high vacuum. The PNA oligomer was then cleaved, deprotected and purified as described below.

Example 12

General Procedure for Cleavage and Deprotection

The synthesis support (Fmoc-PAL-PEG/PS; P/N GEN913384) was then removed from the synthesis cartridge, transferred to a Ultrafree spin cartridge (Miipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) was then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using conventional reversed phase chromatographic methods.

Note: PNAs can be prepared using new product Fmoc-XAL-PEG/PS synthesis support (P/N GEN 913394) available from PerSeptive Biosystems, Inc. This support has the advantage that the PNA can be removed more rapidly and under more mildly acid conditions. PNAs prepared with Fmoc-XAL-PEG/PS support are typically treated as described above except that a solution of TFA/m-cresol 9/1 is often used for a period of 10–15 minutes (2×).

The following Table Lists Exemplary PNA Oligomers which were Modified Using the Novel Compositions of this Invention

TABLE 1

| PNA Sequence | Purity | Ratio: Purine/Purine + Pyrimidine |
|---|---|---|
| Flu-OE-AAT-AAT-AAT-AAT-AAT-E-$NH_2$ | >95% | 0.667 |
| Flu-OE-CGC-GCG-CGC-GCG-CGC-E-$NH_2$ | >90% | 0.533 |
| Flu-OE-GGT-GGT-GGT-GGT-GGT-E-$NH_2$ | >90% | 0.667 |
| Flu-OE-AGA-AGA-AGA-AGA-AGA-E-$NH_2$ | >90% | 1.00 |
| Flu-OE-GAG-GAG-GAG-GAG-GAG-E-$NH_2$ | >80% | 1.00 |
| Flu-OE-ACG-ACG-ACG-ACG-ACG-E-$NH_2$ | >98% | 0.667 |
| Flu-OE-AGT-AGT-AGT-AGT-AGT-E-$NH_2$ | >98% | 0.667 |
| Flu-OE-ATG-ATG-ATG-ATG-ATG-E-$NH_2$ | >98% | 0.667 |
| Flu-OOE-AAA-AAA-GAG-+-$NH_2$ | >98% | 1.00 |
| Flu-OEE-GGG-GGG-G-EE-$NH_2$ | >95% | 1.00 |
| H-OOE-GTG-GAC-GCC-GGG-GCC-E-$NH_2$ | >98% | 0.600 |
| H-OE-TTA-GGG-TTA-GGG-TTA-GGG-EE-$NH_2$ | >96% | 0.667 |
| Cy3-OE-TTA-GGG-TFA-GGG-TTA-GGG-EE-$NH_2$ | >97% | 0.667 |

The sequences listed above are generally problematic because they are either purine-rich, especially G-rich, contain regions of self-complementarity, violate the synthesis guidelines and/or were found to be relatively insoluble when unmodified. PNA sequences are written from the amine to the carboxyl terminus. Abbreviations are: Flu=5-(6)-carboxyfluorescein, Cy3=the cyanine 3 dye from Amersham, O=8-amino-3,6-dioxaoctanoic acid and E is “E” and + is “+”.

Example 13

HPLC and Mass Analysis

PNA probes were analyzed and purified by reversed phase HFLC. Probe composition was confirmed by comparison with theoretical calculated masses. The crude product of PNA oligomer P3 (Table 5) was prepurified using anion exchange chromatography prior to reversed phase HPLC purification using Gradient B. Anion exchange chromatography generally improved the purity level to better than 70 percent. Sephadex (Pharmacia Biotech) was used as the stationary phase and the mobile phase was 10 mM sodium hydroxide with a sodium chloride gradient. Other probes were purified using Gradient A. Preparative purifications were scaled based on the analytical analysis conditions described in Gradients A & B. Generally, the analysis conditions described below were scaled to accommodate the quantity of PNA to be injected for purification. The purified PNAs were then reanalyzed by HPLC and mass analysis to confirm purity and identity, respectively.

HPLC Procedures:

Gradients A & B

Buffer A=0.1% TFA in water.

Buffer B=0.1% TFA in acetonitrile.

Flow Rate: 0.2 mL/min.

Column Temperature: 60° C.

Instrument: Waters 2690 Alliance: Control by Waters Millennium Software

Stationary Phase: Waters Delta Pak C18, 300 Å, 5 μm, 2×150 mm (P/N WAT023650) Detection at 260 nm

| Time (min.) | Percent Buffer A | Percent Buffer B | Curve |
|---|---|---|---|
| Gradient Profile A | | | |
| 0.00 | 100 | 0 | 0 |
| 4.00 | 100 | 0 | 6 |
| 22.00 | 80 | 20 | 6 |
| 38.00 | 40 | 60 | 6 |
| 40.00 | 20 | 80 | 11 |
| Gradient Profile B | | | |
| 0.00 | 90 | 10 | 0 |
| 40.00 | 60 | 40 | 6 |
| 50.00 | 20 | 80 | 6 |

Mass Analysis

Samples of crude and purified polymers were analyzed using a linear Voyager Delayed Extraction Matrix Assisted Laser Desorption Ionization-Time Of Flight (DE MALDI-TOF) Mass spectrometer (PerSeptive Biosystems, Inc.). Sinipinic acid was used as the sample matrix and also used as one point for calibration of the mass axis. We use bovine insulin as an internal calibration standard for the second calibration point of the mass axis.

Samples were prepared for analysis by first preparing a solution of sinipinic acid at a concentration of 10 mg/mL in a 1:2 mixture of acetonitrile and 0.1% aqueous trifluoroacetic acid. Next, an insulin solution was prepared by dissolving 1 mg of bovine insulin (Sigma) in 0.1% aqueous trifluoroacetic acid. Finally, an insulin/matrix solution was then prepared by mixing 9 parts of the sinipinic acid solution to 1 part of the bovine insulin solution. Samples were prepared for analysis by spotting 1 μL of the insulin/matrix solution followed by spotting 1 μL of diluted sample (approximately 0.1 to 1 OD per mL) onto the mass spectrometer target. The M/S target was allowed to dry before being inserted into the mass spectrometer.

Example 14

Cy3 and Cy5 Labeling of PNAs

The purified amine containing PNA was dissolved in 1/1 DMF/water at a concentration of 0.05 OD/μL to prepare a stock PNA solution. From the stock, approximately 30 nmole of PNA was added to a tube. To this tube was then added 125 μL 0.1 M HEPES (pH 8.5), and enough 1/1 DMF/water to bring the total volume to 250 μL. This solution was thoroughly mixed. To a prepackaged tube of Cy3 dye (Amersham P/N PA23001), was added the entire 250 $\mu$L solution prepared as described above. The tube is well mixed and then allowed to react for 1 hour at ambient temperature.

After reaction, the solvent is removed by evaporation in a speed-vac. The pellet was then dissolved in 400 $\mu$L of a solution containing 3:11% aqueous TFA/ACN. Optionally the solution was then transferred to a 5000 MW Ultrafree (Millpore, P/N UFC3LCC25) or a 3000 MW (Amicon, P/N 42404) filter to removed excess dye. Whether or not the excess dye was removed, the recovered product was repurified by HPLC.

Figure 7:
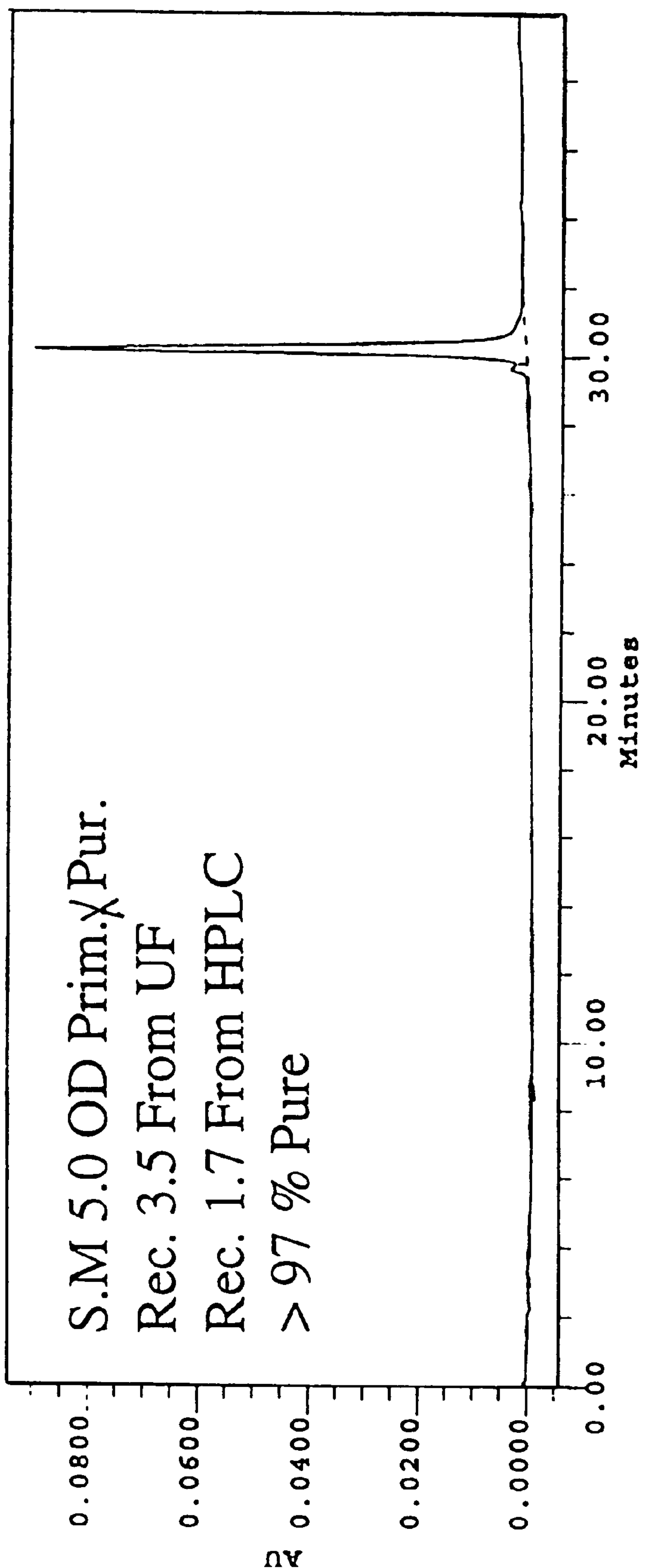
FIG. 7 is an HPLC chromatogram of a soluble, purified Cy3 labeled PNA oligomer.

With reference to FIG. 7, the unmodified PNA oligomer H-OO-TTA-GGG-TTA-GGG-TTA-GGG-$NH_2$ was found to be extremely insoluble at pH 8.5, though this oligomer does not violate any of the aforementioned synthesis guidelines (rules) known to those in the art. The PNA oligomer was not soluble at a concentration of 0.05 OD/$\mu$L Because of the very limited solubility, this oligomer was determined to be very difficult to label. However, the modified polymer H-OE-TTA-GGG-TTA-GGG-TTA-GGG-EE-$NH_2$ was fully soluble at a concentration of 0.05 OD/$\mu$L, labeled well and was easily characterized. Moreover, the recovery of the polymer from the labeling reaction was quite good. With reference to the figure, 5.0 OD was used in the reaction. 3.5 OD was recovered from the Ultrafree cartridge and 1.7 OD of pure PNA was recovered from the HPLC purification.

Example 15

Dot Blot rRNA Preparation:

Using a Qiagen kit (P/N 75144), the ribosomal RNA (rRNA) from bacteria was isolated and prepared for spotting onto the membranes.

Hybridization to the Membranes:

Dot blots were made on nylon membranes obtained from Gibco-BRL (P/N 14830-012). The concentrations of rRNA were normalized at a final concentration of 0.05 $\mu$g/L, and half log dilutions of each RNA was made in diethyl pyrocarbonate treated water (RNase free). Each dilution was heated to 68° C. for three minutes and then spotted onto the dry membrane. Once the rRNA was dried it was UV crosslinked and stored in a plastic bag.

Figures 10A, 10B:
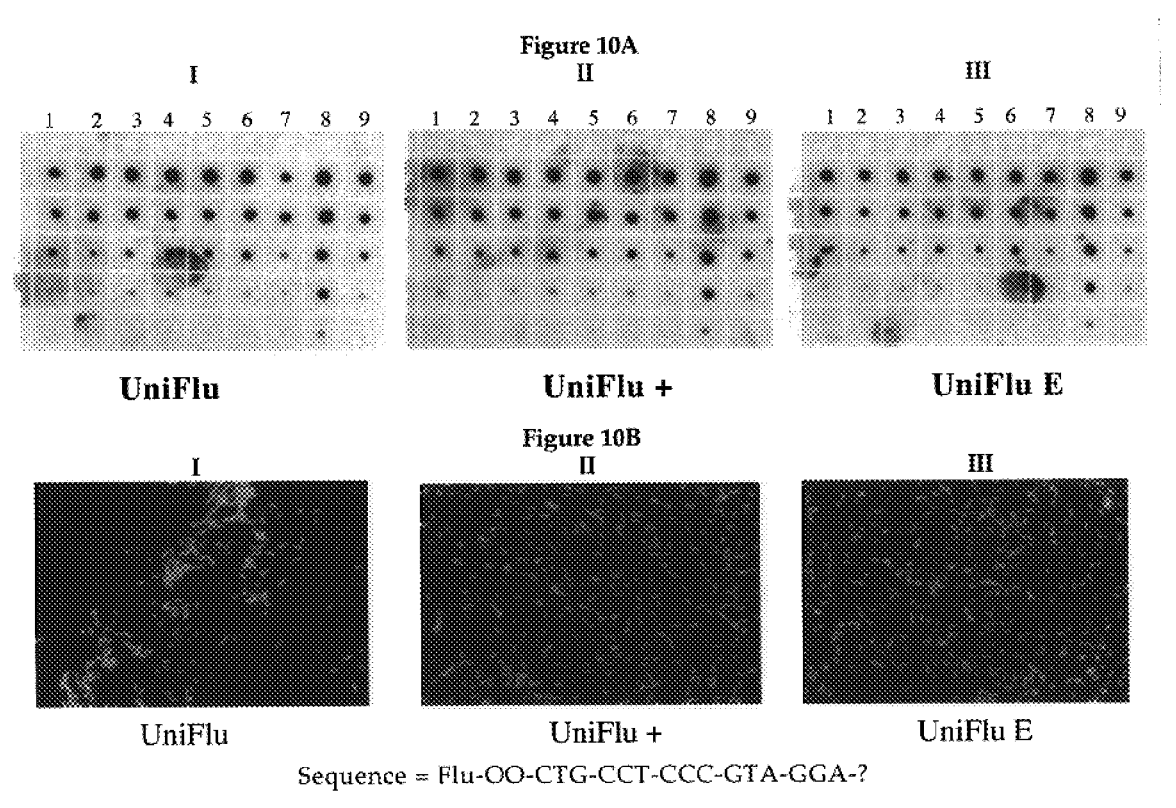

With reference to FIGS. 10A I–III, the rRNA of each of the following bacteria were spotted on three membranes in the columns illustrated: 1 *Pseudomonas fluorescens*, 2 *Pseudomonas aeruginosa*, 3 *Pseudomonas cepatia*, 4 *Pseudomonas putida*, 5 *Escherichia coli*, 6 *Bacillus subtilis*, 7 *Staphylococcus epidermidis*, 8 *Staphylococcus aureus*, and 9 *Salmonella typhimuriam*. A total of 16 ng of rRNA was spotted at the top of each membrane using the most concentrated stock and each serial dilution was consecutively spotted in the column. The membranes were placed in plastic bags and pre-wet with RNase free water. The membranes were prehybridized in hybridization buffer (50% formamide, 20 mM Tris (pH 7.5), 0.1% sodium dodecyl sulfate (SDS) and 100 mM NaCl) for 15 minutes at 50° C.

The prehybridization buffer was removed from the bag and fresh buffer containing the probe of interest, as prepared above, was added to the bag. With reference to FIG. 10A, three membranes were prepared. The appropriate probe was added to a final concentration of 1 pmol/mL in fresh hybridization buffer. One membrane was probed with unmodified Uni-Flu (I), one membranes with UniFlu + (II) and one membrane with Uni-Flu E (III). The Uni-Flu sequence is a fluorescein labeled PNA having a sequence which is intended to target a highly conserved rRNA sequence in the bacterial genome to thereby hybridize to the rRNA of all bacterial species.

The hybridization was performed at 50° C. for 1 hour. The filters were then washed 3 times in TE (pH 7.5, 10 mM Tris, 1 mM EDTA) with 0.2% SDS. The first wash was at room temperature for 5 minutes. The second and third washes were at 65° C. for 10–15 minutes each.

Visualization of the Membrane:

After the washes were completed, the membranes were treated with a solution containing 0.05 M Tris (pH 9.0), 0.5 M NaCl, and 0.5% casein (blocking solution). The starting temperature of the solution was 65° C., but the solution cooled as the blocking was done with shaking at room temperature for 15 minutes. A $\alpha$-fluorescein-alkaline phosphatase conjugate (Rabbit (Fab)-anti-FITC/AP (DAKO P/N)) was diluted 1:1000 in blocking solution and the membranes were left in this solution, while shaking, for 30 minutes at room temperature. The membranes were then washed in a solution containing 0.05 M Tris (pH 9.0), 0.5 M NaCl and 0.5% Tween-20 three times for 5 minutes. A final rinse was performed with a solution containing 10 mM Tris (pH 9.5), 10 mM NaCl, and 1 mM $MgCl_2$. The chemiluminescent substrate (AMPPD, Tropix Corp., P/N PD025) was diluted 1:100 in an aqueous solution containing 0.1 M diethanolamine and 1 mM $MgCl_2$ (pH 9.7) and this solution was contacted with the membranes for 4 minutes. The membranes were placed in bags and the excess substrate was squeezed out and the bag sealed. The membranes were exposed to Fuji-RX X-ray film for between 1 and 5 minutes.

With reference to FIGS. 10A I–III, there is no detectable difference between the hybridization/detection of each of the modified and unmodified probes.

Example 16

PNA-FISH

For each sample prepared, 100 $\mu$l of cells in 50%/ ethanol was removed and centrifuged at 8000 R.P.M. for 2 min. The ethanol was then remove from the sample and the pellet was resuspended in 100 $\mu$l of sterile solution containing 130 mM NaCl, 7 mM $NaHPO_4$, 3 mM $NaH_2PO_4$ (1×PBS). This solution was then centrifuged at 8000 R.P.M. or 2 min.

The PBS was then removed from the pellet, and the cells were resuspended in 100 $\mu$l of hybridization buffer [0.5% SDS, 100 mnM NaCl, 20 mM Tris (pH 9.0)] which contained the appropriate probe (concentration 30 pmol/mL). The hybridization was performed at 55° C. for 30 minutes.

The sample was then centrifuged at 8000 R.P.M. for 2 min. The hybridization buffer was removed and the cells resuspended in 500 $\mu$l sterile TE (pH 7.5, 10 mM Tris, 1 mM EDTA). The solution was allowed to stand at 55° C. for 5 minutes. The sample was then centrifuged at 8000 R.P.M. for 5 minutes. The TE was then removed from the pellet. The TE wash was repeated two more times.

After the final wash the cells were resuspended in 50 $\mu$l of 1×PBS. An aliquot of 2 $\mu$l of this suspension of cells was placed on a glass slide, spread and allowed to dry. A coverslip (Vectashield from Vector Laboratories, P/N H-1000) and propidium iodide (final concentration 0.2 mg/L) was added.

With reference to FIGS. 10B I–III, there is no detectable difference between the hybridization/detection of each of the modified and unmodified probes in the PNA-FISH assay.

Example 17

Thermal Melting Analysis of Modified PNA

Thermal melting analysis of solutions containing approximately 5.1 $\mu$mole/liter of each of UniFlu, UniFlu E and UniFlu + and one equivalent of complementary nucleic acid (HO-TCC-TAC-GGG-AGG-CAG-OH Seq. ID No 1) in buffer containing 100 mM NaCl, 20 mM sodium phosphate (pH 7.0) were analyzed using a Perkin-Elmer Lambda 2S fitted with a 6 cell holder and running Winlab 2.0 and Templab 1.0 software. All ffiree duplexes were found to have an identical Tm (approximately 81° C., +/−1° C.).

Example 18

Thermodynamic Analysis of Modified PNA oligomers PNA Oligomers

The reference entitled "Hairpin-Forming peptide nucleic acid Oligomers", Armitage et al., *Biochemistry*, 37: 9417–9425 (1998) is admitted as prior art to this Example 18 only. The PNA probe identified as PNAD (Table 2) has been shown to be a PNA hairpin having a 9 base pair duplex stem (See: "Hairpin-Forming peptide nucleic acid Oligomers", Armitage et al., *Biochemistry*, 37: 9417–9425 (1998)). Three other probes identified as P3N, P3 and P4N were prepared as slight modifications of PNAD oligomer but which are designed to maintain the 9 bp duplex stem. Specifically, P4N is a unlabeled PNA oligomer having the same nucleobase sequence as compared with the PNAD oligomer, provided however that the termini of probe P4N have been modified with the solubility enhancer "E". The PNA oligomer P4 is a labeled version of probe P4N wherein the N-termini has been labeled with a fluorescein moiety and the C-terminus has been labeled with a dabcyl moiety. This solubility enhanced PNA oligomer P4 is completely soluble at least up to a concentration of 7.5 μM/L despite the length of the polymer and the presence of the very hydrophobic dabcyl and fluorescein labels. The probe P3N is an unlabeled polymer which compares with P4N in that the nucleobases which comprise the loop portion of the stem and loop hairpin have been replaced with two flexible 8-amino-3,6-dioxaoctanoic acid moieties but the 9 base pair stem is identical in sequence to P4, P4N and PNAD.

The remaining 2.5 mL of the first sample was used for Tm analysis. Serial dilution the samples in Tm Buffer was continued in this fashion until 2.5 mL of Tm Samples at concentrations of approximately 7.5μM, 3.75 μM, 1.87 μM, 0.94 μM and 0.468 μM (5 mL) were prepared. A Tm analysis of these solutions was then performed as described below. Tm data for both the melting "M" and the reannealing "R" is presented in Table 3.

Tm Analysis

1. Tm Bur (Buf):

The five Tm Samples of a dilution series of a particular unimolecular probe to be analyzed were simultaneously examined using a Cary 100 Bio UV-Visible Spectrophotometer (Varian Instruments) equipped with a 6×6 thermostatable multicell block running Win UV Bio application software package. To a 10×10 UV cell (Starna Cells, P/N 21-Q-10) was added a 7.2 mm stir bar and the 2.5 mL of each sample of the dilution series. The stirring accessory was used during all analysis. All samples were thermally denatured and reannealed prior to data collection by having the instrument rapidly ramp the temperature to a point above the melting temperature and then holding that temperature for 5–10 minutes before returning to the starting temperature. The temperature range over which data was collected was varied in response to the expected Tm which was roughly determined during the premelt and prereannealing step. Regardless of the temperature range, the temperature ramp rate for both melting "M" and reannealing "R" was always 0.5° C./min. The absorbance (260 nm, averaged over a 3 second collection) was plotted vs. the temperature of the multicell block.

2. Tm Buffer and 1 mM $MgCl_2$(Buf, Mg):

After the Tm analysis was performed in Tm Buffer, to each cell was added 0.5 μL of 5M $MgCl_2$ to thereby prepare a sample containing 1 mM $MgCl_2$. The dilution effect was considered to be negligible. The Tm analysis was then performed again to determine whether the presence of $MgCl_2$ had any effect on the Tm of the uniimolecular probe.

TABLE 2

Peptide Nucleic Probes

| Probe Sequence | Sequence ID |
|---|---|
| H-OEE-ATA-TAT-TGG-OO-CCA-ATA-TAT-EEK-$NH_2$ | P3N |
| Flu-OEE-ATA-TAT-TGG-CTG-ATC-CAA-TAT-AT-EE-K(dabcyl)-$NH_2$ | P4 |
| H-OEE-ATA-TAT-TGG-CTG-ATC-CAA-TAT-AT-EEK-$NH_2$ | P4N |
| H-ATA-TAT-TGG-CTG-ATC-CAA-TAT-AT-KK-$NH_2$ | PNAD |

Preparation of Dilution Series of PNA and DNA robes for Tm Analysis

Purified PNA probes listed in Table 2 were dissolved in 1:1 DMF/$H_2O$ at 0.05 OD (260 nm) per 20 μL to prepare the PNA Probe Stock Based on calculated extinction coefficients, the appropriate amount of PNA Probe Stock was added to 5 mL of Tm Buffer (10 mM sodium phosphate, pH 7.0) to prepare a solution of approximately 7.5 μM of the PNA oligomers. From this solution was taken 2.5 mL to which was added 2.5 mL of Tm buffer to thereby prepare the second concentration of a dilution series of Tm Samples.

3. Tm Buffer, 1 mM $MgCl_2$ and 100 mM NaCl (Buf, Mg & Na):

After the Tm analysis was performed in Tm Buffer and 1 mM $MgCl_2$, to each cell was added 42 μL of saturated NaCl (approximately 6.11 M/L). The dilution effect was again considered to be negligible. The Tm analysis was then performed again to determine whether the presence of approximately 100 mM NaCl had any effect on the Tm of the unimolecular probe.

TABLE 3

| Probes (Conditions) | UV Tm Analysis | | | | | | | | | |
|---|---|---|---|---|---|---|---|---|---|---|
| | [1] | | [2] | | [3] | | [4] | | [5] | |
| | M | R | M | R | M | R | M | R | M | R |
| P3N (Buf) | 82.6 | 82.3 | 82.5 | 82.4 | 83.0 | 82.4 | 83.0 | 82.5 | 83.0 | 82.6 |
| P3N (Buf, Mg) | 83.1 | 82.4 | 83.1 | 81.9 | 83.0 | 82.5 | 83.0 | 83.1 | 83.0 | 82.6 |
| P3N (Buf, Mg & Na) | 83.1 | 82.9 | 83.1 | 81.4 | 83.5 | 82.9 | 83.5 | 83.0 | 83.5 | 83.1 |
| P4 (Buf) | 81.6 | 80.9 | 81.6 | 81.4 | 82.1 | 81.5 | 82.0 | 81.5 | 81.5 | 81.1 |
| P4 (Buf, Mg) | 81.6 | 81.0 | 81.6 | 81.5 | 82.0 | 81.5 | 82.0 | 81.1 | 82.0 | 81.6 |
| P4 (Buf, Mg & Na) | 82.6 | 81.8 | 82.6 | 82.4 | 82.6 | 82.5 | 82.5 | 82.5 | 83.0 | 82.1 |
| P4N (Buf) | 81.6 | 81.4 | 82.1 | 81.5 | 82.1 | 81.5 | 82.5 | 81.1 | 82.0 | 80.1 |
| P4N (Buf, Mg) | 81.6 | 81.3 | 81.6 | 81.3 | 82.1 | 81.4 | 82.0 | NM | 82.0 | 81.1 |
| P4N (Buf, Mg & Na) | 82.1 | 82.3 | 82.1 | 82.3 | 82.5 | NM | 82.0 | 82.0 | 84.0 | 81.6 |
| PNAD (Buf) | 81.1 | 80.4 | 81.1 | 81.0 | 82.0 | 81.0 | 81.5 | 81.5 | 81.5 | 81.1 |
| PNAD (Buf, Mg) | 80.6 | 80.3 | 81.1 | 80.4 | 81.1 | 80.4 | 80.5 | 81.0 | 80.5 | 80.5 |
| PNAD (Buf, Mg & Na) | 80.6 | 80.4 | 81.5 | NM | 81.0 | 81.4 | 81.5 | 80.5 | 82.1 | 80.6 |

NM = not meaningful

Results:

Though the Tm of labeled and unlabeled hairpins having an identical 9 bp stem duplex where all very similar without regard to the buffer conditions examined (approximately 81–83° C.; See Table 3), normalized data presented in FIG. 11 demonstrates that several factors can influence thermodynamic parameters of the stem duplex. When considered in light of the data in Example 14, it becomes clear that the solubility enhancer "E" does not substantially affect Tm of the duplex even when several modifying moieties are present in the PNA oligomer.

Figure 11:
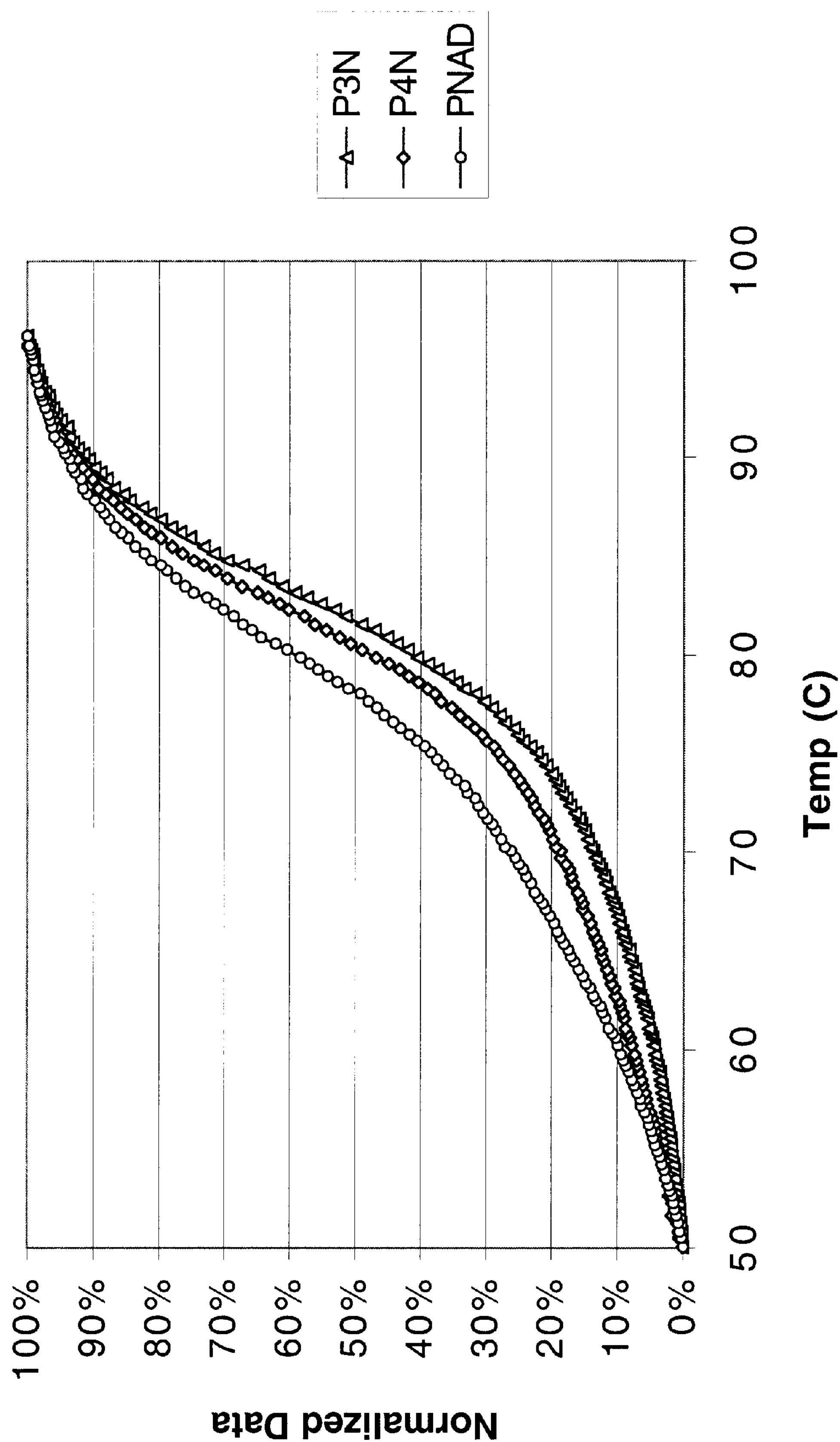
FIG. 11 is an overlay of normalized absorbance vs. temperature plots for three PNAs of similar nucleobase sequence which form a unimolecular hairpin stem and loop.

In FIG. 11, normalized absorbance vs. temperature data for melting of the unlabeled probes P3N, P4N and PNAD (each probe at [1]) is graphically illustrated. As these probes were all unlabeled and comprised the same stem nucleobase sequence there were directly comparable. Probe P3N which comprises a flexible linkage which links the two nucleobase sequences which form the stem duplex exhibited the most cooperative sigmoidal transition. Surprisingly, the solubility enhanced probe, P4N, exhibited only a slightly less cooperative a transition as compared with probe P3N. The probe PNAD exhibited the least cooperative sigmoidal transition which was surprisingly less cooperative as compared with P4N.

The shape of the sigmoidal transition evident in absorbance vs. temperature plots is a function of the thermodynamic properties of the duplex. Sharp cooperative transitions are expected for the more thermodynamically stable duplexes whereas sloping sigmoidal transitions are expected where the duplex is less thermodynamically stable. The flexible linkage in P3N was expected to stabilize the duplex so the sharp transition observed was expected. The substantial difference between probe P4N and PNAD however was surprising and can only be attributed to the presence of the solubility enhancer moiety "E". Since P4N exhibited a more cooperative transition as compared with PNAD, the data suggests that the solubility enhancers affect the thermodynamic stability of the stem duplex despite there not being a substantial affect on Tm.

Example 19

Purification Recovery Comparison

As noted in Example 14, applicants have found the PNA oligomer H-OO-TTA-GGG-TTA-GGG-TTA-GGG-$NH_2$ to be extremely insoluble at pH 8.5 though it does not violate the aforementioned synthesis rules known in the art. When attempting to label the solubility enhanced PNA oligomer H-OOE-TTA-GGG-TTA-GGG-TTA-GGG-E-$NH_2$ with cyanine 5 dye (Cy5) a low recovery was obtained from the reaction and purification. Specifically, 5.4 $OD_{260\ nm}$ of PNA was labeled with the Cy5 dye (Amersham P/N PA 25001) but only 0.25 $OD_{260\ nm}$ of purified PNA was recovered from the HPLC purification (See: Example 14 for the general procedure).

Since this PNA oligomer contained only two solubility enhancing "E" moieties as compared with the modified PNA used in Example 14 which comprised three solubility enhancing "E" moieties, the modified PNA oligomer H-OOE-TTA-GGG-TTA-GGG-TTA-GGG-EE-$NH_2$ as prepared and 5.5 $OD_{260\ nm}$ labeled with Cy5. From this reaction approximately 1.0 $OD_{260\ nm}$ of purified PNA was recovered from the HPLC purification. Though several factors can affect the recovery, the four fold increase in recovery was at least partially due to the presence of the additional solubility enhancing "E" moiety. This data further demonstrates that for particularly insoluble PNAs, several solubility enhancing moieties should be linked to the polymer (See: discussion on p. 34, lns. 6–15).

We claim:

1. A purified purine-rich PNA oligomer comprising 8 or more nucleobase containing subunits wherein said subunits have the formula:

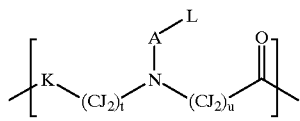

wherein, each J is the same or different and is selected from the group consisting of H, $R^1$, $OR^1$, $SR^1$, $NHR^1$, $NR^1_2$, F, Cl, Br and I;

each K is the same or different and is selected from the group consisting of O, S, NH and $NR^1$;

each $R^1$ is the same or different and is an alkyl group having one to five carbon atoms which may optionally contain a heteroatom or a substituted or unsubstituted aryl group;

each A is selected from the group consisting of a single bond, a group of the formula; —$(CJ_2)_s$— and a group of the formula; —$(CJ_2)_sC(O)$—, wherein, J is defined above and each s is an integer from one to five;

the integer t is 1 or 2 and the integer u is 1 or 2;

each L is the same or different and is independently selected from the group consisting of: adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs and other non-naturally occurring nucleobases.

2. A purified PNA oligomer having greater than 6 sequential purine nucleobase containing subunits wherein said subunits have the formula:

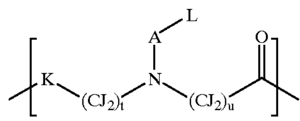

wherein, each J is the same or different and is selected from the group consisting of H, $R^1$, $OR^1$, $SR^1$, $NHR^1$, $NR^1_2$, F, Cl, Br and I;

each K is the same or different and is selected from the group consisting of O, S, NH and $NR^1$;

each $R^1$ is the same or different and is an alkyl group having one to five carbon atoms which may optionally contain a heteroatom or a substituted or unsubstituted aryl group;

each A is selected from the group consisting of a single bond, a group of the formula; —$(CJ_2)_s$— and a group of the formula; —$(CJ_2)_sC(O)$—, wherein, J is defined above and each s is an integer from one to five;

the integer t is 1 or 2 and the integer u is 1 or 2;

each L is the same or different and is independently selected from the group consisting of: adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs and other non-naturally occurring nucleobases.

3. A purified homopurine PNA oligomer comprising 6 or more nucleobase containing subunits wherein said subunits have the formula:

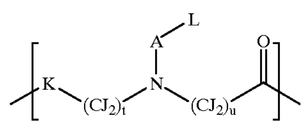

wherein, each J is the same or different and is selected from the group consisting of H, $R^1$, $OR^1$, $SR^1$, $NHR^1$, $NR^1_2$, F, Cl, Br and I;

each K is the same or different and is selected from the group consisting of O, S, NH and $NR^1$;

each $R^1$ is the same or different and is an alkyl group having one to five carbon atoms which may optionally contain a heteroatom or a substituted or unsubstituted aryl group;

each A is selected from the group consisting of a single bond, a group of the formula; —$(CJ_2)_s$— and a group of the formula; —$(CJ_2)_sC(O)$—, wherein, J is defined above and each s is an integer from one to five;

the integer t is 1 or 2 and the integer u is 1 or 2;

each L is the same or different and is independently selected from the group consisting of: adenine, cytosine, guanine, thymine, uridine, 5-methylcytosine, 2-aminopurine, 2-amino-6chloropurine, 2,6-diaminopurine, hypoxanthine, pseudoisocytosine, 2-thiouracil, 2-thiothymidine, other naturally occurring nucleobase analogs and other non-naturally occurring nucleobases.

4. A purified PNA oligomer having four or more sequential guanine containing subunits in a PNA oligomer having 6 or more nucleobase containing subunits wherein said subunits have the formula:

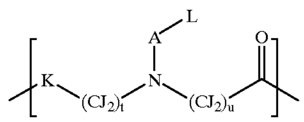

wherein, each J is the same or different and is selected from the group consisting of H, $R^1$, $OR^1$, $SR^1$, $NHR^1$, $NR^1_2$, F, Cl, Br and I;

each K is the same or different and is selected from the group consisting of O, S, NH and $NR^1$;

each $R^1$ is the same or different and is an alkyl group having one to five carbon atoms which may optionally contain a heteroatom or a substituted or unsubstituted aryl group;

each A is selected from the group consisting of a single bond, a group of the formula; —$(CJ_2)_s$— and a group of the formula; —$(CJ_2)_sC(O)$—, wherein, J is defined above and each s is an integer from one to five;

the integer t is 1 or 2 and the integer u is 1 or 2;

each L is the same or different and is independently selected from the group consisting of: adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs and other non-naturally occurring nucleobases.

5. The PNA oligomer of claim 1, wherein the PNA is labeled with one or more hydrophobic labels.

6. The PNA oligomer of claim 1, having a purity of greater than 80 percent.

7. The PNA oligomer of claim 1, wherein one or more uncharged, non-nucleophilic and achiral modifying moieties is linked to the PNA oligomer.

8. The PNA oligomer of claim 1, wherein one or more positively charged, non-nucleophilic and achiral modifying moieties is linked to the PNA oligomer.

9. The PNA oligomer of claim 2, having a purity of greater than 80 percent.

10. The PNA oligomer of claim 2, wherein the PNA is labeled with a hydrophobic label.

11. The PNA oligomer of claim 2, wherein one or more uncharged, non-nucleophilic and achiral modifying moieties is linked to the PNA oligomer.

12. The PNA oligomer of claim 2, wherein one or more positively charged, non-nucleophilic and achiral modifying moieties is linked to the PNA oligomer.

13. The PNA oligomer of claim 3, having a purity of greater than 80 percent.

14. The PNA oligomer of claim 3, wherein the PNA is labeled with a hydrophobic label.

15. The PNA oligomer of claim 3, wherein one or more uncharged, non-nucleophilic and achiral modifying moieties is linked to the PNA oligomer.

16. The PNA oligomer of claim 3, wherein one or more positively charged, non-nucleophilic and achiral modifying moieties is linked to the PNA oligomer.

17. The PNA oligomer of claim 4, having a purity of greater than 80 percent.

18. The PNA oligomer of claim 4, wherein the PNA is labeled with a hydrophobic label.

19. The PNA oligomer of claim 4, wherein one or more uncharged, non-nucleophilic and achiral modifying moieties is linked to the PNA oligomer.

20. The PNA oligomer of claim 4, wherein one or more positively charged, non-nucleophilic and achiral modifying moieties is linked to the PNA oligomer.

21. A PNA oligomer to which is linked one or more modifying moieties having the formula:

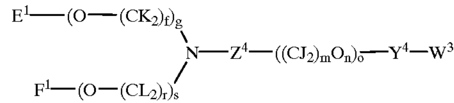

wherein, $Z^4$ is selected from the group consisting of: —C(O)—, —C(S)—, —$S(O_2)$— and a bond;

$W^3$ is selected from the group consisting of: —$Q^2$, —$C(O)Q^2$, —$C(S)Q^2$, and —$S(O_2)Q^2$;

$Y^4$ is selected from the group consisting of a bond and a group having the formula: —$(CI_2)_e$—, wherein e is a whole number from 1 to 10, provided that if $Y^4$ is a bond, then $W^3$ is selected from the group consisting of —$C(O)Q^2$, —$C(S)Q^2$, and —$S(O_2)Q^2$;

$E^1$ is selected from the group consisting of Pg5 and $R^1$;

$F^1$ is selected from the group consisting of Pg5 and $R^1$;

o is a whole number from 0 to 10;

each n is independently 0 or 1;

each f, g, m, r and s is independently an integer from 1 to 10;

each I, J, K and L is independently selected from the group consisting of: H, X and $R^1$;

wherein, each $R^1$ is selected from the group consisting of: —$CD_3$, —$CD_2CD_3$, —$CD_2CD_2CD_3$, —$CD_2CD(CD_3)_2$, and —$C(CD_3)_3$, wherein each D is independently selected from the group consisting of H, —O—Pg5 and X;

each Pg5 is independently a hydroxyl protecting group;

each X is independently selected from the group consisting of F, Cl, Br and I;

$Q^2$ is link to a subunit of the PNA oligomer.

22. The PNA oligomer of claim 1, wherein a PNA subunit consists of a naturally occurring or non-naturally occurring nucleobase attached to the aza nitrogen of a N-[2-(aminoethyl)]glycine backbone through a methylene carbonyl linkage.

23. The PNA oligomer of claim 1, wherein the polymer is completely achiral.

24. The PNA oligomer of claim 1, wherein the polymer comprises one or more linked modifying moieties having the formula:

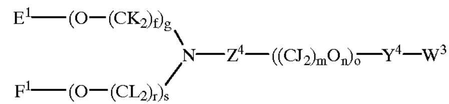

wherein, $Z^4$ is selected from the group consisting of: —C(O)—, —C(S)—, —$S(O_2)$— and a bond;

$W^3$ is selected from the group consisting of: —$Q^2$, —$C(O)Q^2$, —$C(S)Q^2$, and —$S(O_2)Q^2$;

$Y^4$ is selected from the group consisting of a bond and a group having the formula: —$(CI_2)_e$—, wherein e is a whole number from 1 to 10, provided that if $Y^4$ is a bond, then $W^3$ is selected from the group consisting of —$C(O)Q^2$, —$C(S)Q^2$, and —$S(O_2)Q^2$;

$E^1$ is selected from the group consisting of Pg5 and $R^1$;

$F^1$ is selected from the group consisting of Pg5 and $R^1$;

o is a whole number from 0 to 10;

each n is independently 0 or 1;

each f, g, m, r and s is independently an integer from 1 to 10;

each I, J, K and L is independently selected from the group consisting of: H, X and $R^1$;

wherein, each $R^1$ is selected from the group consisting of: $—CD_3$, $—CD_2CD_3$, $—CD_2CD_2CD_3$, $—CD_2CD(CD_3)_2$, and $—C(CD_3)_3$, wherein each D is independently selected from the group consisting of H, —O—Pg5 and X;

each Pg5 is independently a hydroxyl protecting group;

each X is independently selected from the group consisting of F, Cl, Br and I;

$Q^2$ is link to a subunit of the PNA oligomer.

25. The PNA oligomer of claim 24, wherein the one or more linked modifying moieties has the formula:

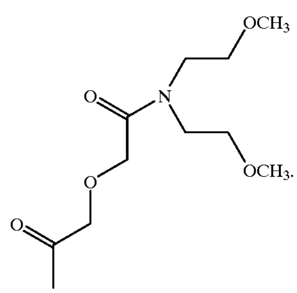

26. The PNA oligomer of claim 24, wherein the one or more linked modifying moieties have the formula:

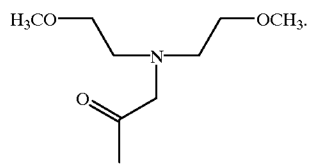

27. The PNA oligomer of claim 7, wherein the one or more modifying moieties have the formula:

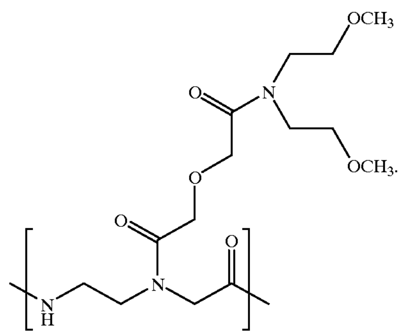

28. The PNA oligomer of claim 8, wherein the one or more modifying moieties have the formula:

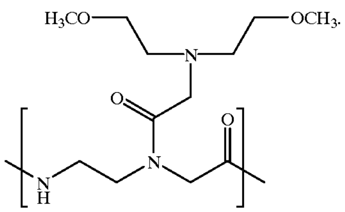

29. The PNA oligomer of claim 2, wherein a PNA subunit consists of a naturally occurring or non-naturally occurring nucleobase attached to the aza nitrogen of a N-[2-(aminoethyl)]glycine backbone through a methylene carbonyl linkage.

30. The PNA oligomer of claim 2, wherein the polymer is completely achiral.

31. The PNA oligomer of claim 2, wherein the polymer comprises one or more linked modifying moieties having the formula:

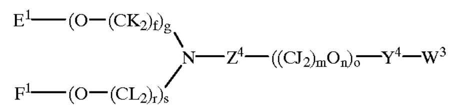

wherein, $Z^4$ is selected from the group consisting of: —C(O)—, —C(S)—, $—S(O_2)—$ and a bond;

$W^3$ is selected from the group consisting of: $—Q^2$, $—C(O)Q^2$, $—C(S)Q^2$, and $—S(O_2)Q^2$;

$Y^4$ is selected from the group consisting of a bond and a group having the formula: $—(CI_2)_e—$, wherein e is a whole number from 1 to 10, provided that if $Y^4$ is a bond, then $W^3$ is selected from the group consisting of $—C(O)Q^2$, $—C(S)Q^2$, and $—S(O_2)Q^2$;

$E^1$ is selected from the group consisting of Pg5 and $R^1$;

$F^1$ is selected from the group consisting of Pg5 and $R^1$;

o is a whole number from 0 to 10;

each n is independently 0 or 1;

each f, g, m, r and s is independently an integer from 1 to 10;

each I, J, K and L is independently selected from the group consisting of: H, X and $R^1$;

wherein, each $R^1$ is selected from the group consisting of: $—CD_3$, $—CD_2CD_3$, $—CD_2CD_2CD_3$, $—CD_2CD(CD_3)_2$, and $—C(CD_3)_3$, wherein each D is independently selected from the group consisting of H, —O—Pg5 and X;

each Pg5 is independently a hydroxyl protecting group;

each X is independently selected from the group consisting of F, Cl, Br and I;

$Q^2$ is link to a subunit of the PNA oligomer.

32. The PNA oligomer of claim 31, wherein the one or more linked modifying moieties have the formula:

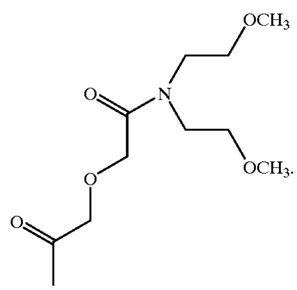

33. The PNA oligomer of claim 31, wherein the one or more linked modifying moieties have the formula:

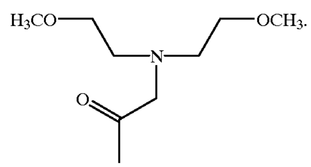

34. The PNA oligomer of claim 11, wherein the one or more modifying moieties have the formula:

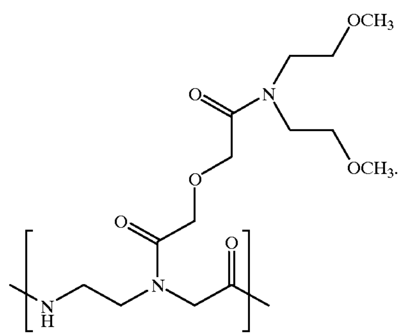

35. The PNA oligomer of claim 12, wherein the one or more modifying moieties have the formula:

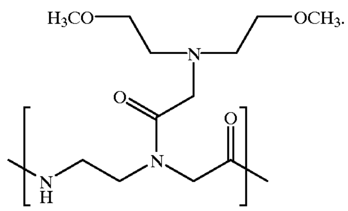

36. The PNA oligomer of claim 3, wherein a PNA subunit consists of a naturally occurring or non-naturally occuring nucleobase attached to the aza nitrogen of a N-[2-(aminoethyl)]glycine backbone through a methylene carbonyl linkage.

37. The PNA oligomer of claim 3, wherein the polymer is completely achiral.

38. The PNA oligomer of claim 3, wherein the polymer comprises one or more linked modifying moieties having the formula:

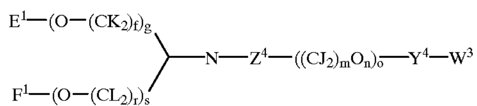

wherein, $Z^4$ is selected from the group consisting of: —C(O)—, —C(S)—, —$S(O_2)$— and a bond;

$W^3$ is selected from the group consisting of: —$Q^2$, —C(O)$Q^2$, —C$(S)^2$Q, and —$S(O_2)Q^2$;

$Y^4$ is selected from the group consisting of a bond and a group having the formula: —$(CI_2)_e$—, wherein e is a whole number from 1 to 10, provided that if $Y^4$ is a bond, then $W^3$ is selected from the group consisting of —C(O)$Q^2$, —C(S)$Q^2$, and —$S(O_2)Q^2$;

$E^1$ is selected from the group consisting of Pg5 and $R^1$;

$F^1$ is selected from the group consisting of Pg5 and $R^1$;

o is a whole number from 0 to 10;

each n is independently 0 or 1;

each f, g, m, r and s is independently an integer from 1 to 10;

each I, J, K and L is independently selected from the group consisting of: H, X and $R^1$;

wherein, each $R^1$ is selected from the group consisting of: —$CD_3$, —$CD_2CD_3$, —$CD_2CD_2CD_3$, —$CD_2CD(CD_3)_2$, and —$C(CD_3)_3$, wherein each D is independently selected from the group consisting of H, —O—Pg5 and X;

each Pg5 is independently a hydroxyl protecting group;

each X is independently selected from the group consisting of F, Cl, Br and I;

$Q^2$ is link to a subunit of the PNA oligomer.

39. The PNA oligomer of claim 38, wherein the one or more linked modifying moieties have the formula:

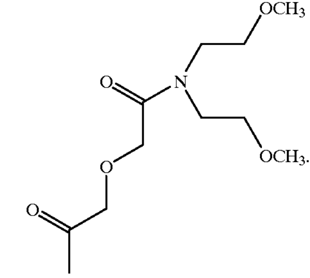

40. The PNA oligomer of claim 38, wherein the one or more linked modifying moieties have the formula:

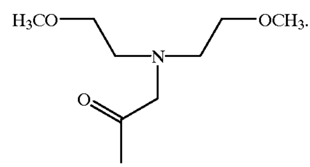

41. The PNA oligomer of claim 15, wherein the one or more modifying moieties have the formula:

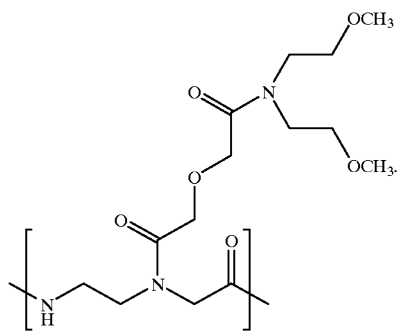

42. The PNA oligomer of claim 16, wherein the one or more modifying moieties have the formula:

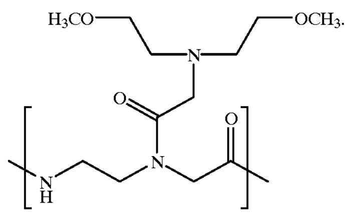

43. The PNA oligomer of claim 4, wherein a PNA subunit consists of a naturally occurring or non-naturally occurring nucleobase attached to the aza nitrogen of a N-[2-(aminoethyl)]glycine backbone through a methylene carbonyl linkage.

44. The PNA oligomer of claim 4, wherein the polymer is completely achiral.

45. The PNA oligomer of claim 4, wherein the polymer comprises one or more linked modifying moieties having the formula:

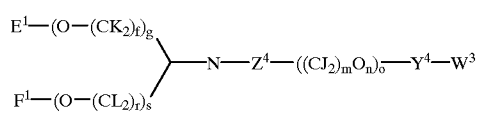

wherein, $Z^4$ is selected from the group consisting of: —C(O)—, —C(S)—, —$S(O_2)$— and a bond;

$W^3$ is selected from the group consisting of: —$Q^2$, —C(O)$Q^2$, —C(S)$Q^2$, and —$S(O_2)Q^2$;

$Y^4$ is selected from the group consisting of a bond and a group having the formula: —$(CI_2)_e$—, wherein e is a whole number from 1 to 10, provided that if $Y^4$ is a bond, then $W^3$ is selected from the group consisting of —C(O)$Q^2$, —C(S)$Q^2$, and —$S(O_2)Q^2$;

$E^1$ is selected from the group consisting of Pg5 and $R^1$;

$F^1$ is selected from the group consisting of Pg5 and $R^1$;

o is a whole number from 0 to 10;

each n is independently 0 or 1;

each f, g, m, r and s is independently an integer from 1 to 10;

each I, J, K and L is independently selected from the group consisting of: H, X and $R^1$;

wherein, each $R^1$ is selected from the group consisting of: —$CD_3$, —$CD_2CD_3$, —$CD_2CD_2CD_3$, —$CD_2CD(CD_3)_2$, and —$C(CD_3)_3$, wherein each D is independently selected from the group consisting of H, —O—Pg5 and X;

each Pg5 is independently a hydroxyl protecting group;

each X is independently selected from the group consisting of F, Cl, Br and I;

$Q^2$ is link to a subunit of the PNA oligomer.

46. The PNA oligomer of claim 45, wherein the one or more linked modifying moieties have the formula:

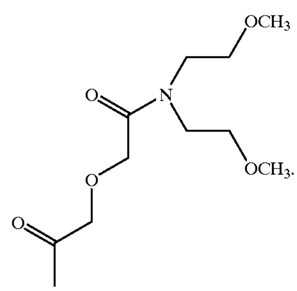

47. The PNA oligomer of claim 45, wherein the one or more linked modifying moieties have the formula:

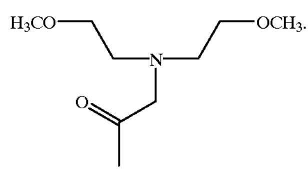

48. The PNA oligomer of claim 19, wherein the one or more modifying moieties have the formula:

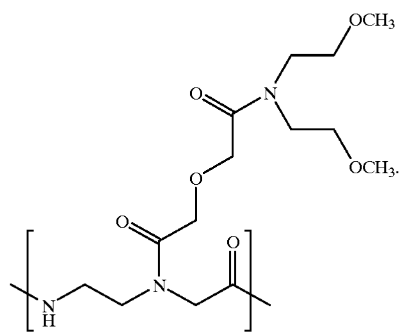

49. The PNA oligomer of claim 20, wherein the one or more modifying moieties have the formula:

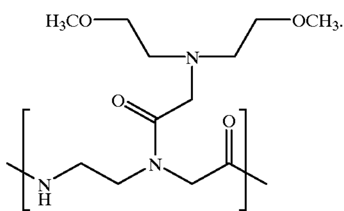

50. The PNA oligomer of claim 21, wherein the one or more linked modifying moieties have the formula:

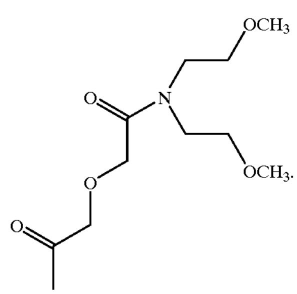

51. The PNA oligomer of claim 21, wherein the one or more linked modifying moieties have the formula:

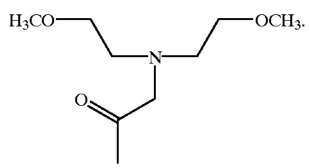

52. The PNA oligomer of claim 21, wherein the polymer is completely achiral.

53. The PNA oligomer of claim 21, wherein the PNA is labeled with one or more hydrophobic labels.

54. A PNA oligomer to which is lied, at a position adjacent to the nucleobase containing subunits, one or more achiral modifying moieties.

55. The PNA oligomer of claim 54, wherein the one or more achiral linked modifying moieties have the formula:

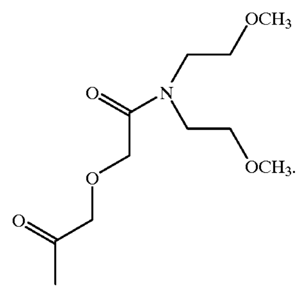

56. The PNA oligomer of claim 54, wherein the one or more linked achiral modifying moieties have the formula:

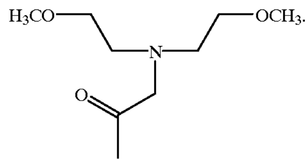

57. The PNA oligomer of claim 54, wherein the one or more achiral linked modifying moieties have the formula:

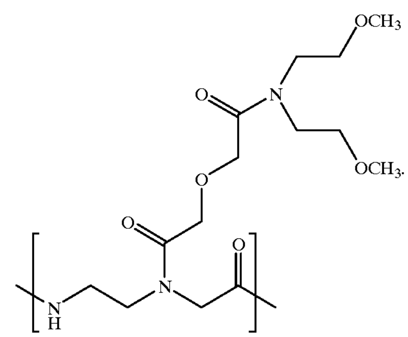

58. The PNA oligomer of claim 54, wherein the one or more achiral linked modifying moieties have the formula:

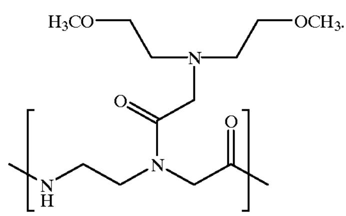

59. The PNA oligomer of claim 54, wherein the PNA has been purified such that it is greater than 80 percent pure.

60. The PNA oligomer of claim 54, wherein the PNA comprises one or more hydrophobic labels.

61. A completely achiral purified purine-rich PNA oligomer.

62. The PNA oligomer of claim 61, wherein the PNA comprises 6 or more sequential purine residues.

63. The PNA oligomer of claim 61, wherein the PNA is a homopurine polymer.

64. The PNA oligomer of claim 61, wherein the PNA comprises four or more sequential guanine containing subunits.

65. The PNA oligomer of claim 61, wherein the PNA comprises one or more linked modifying moieties having the formula:

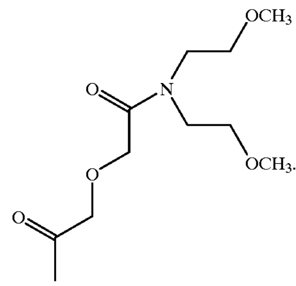

66. The PNA oligomer of claim 61, wherein the PNA comprises one or more linked modifying moieties having the formula:

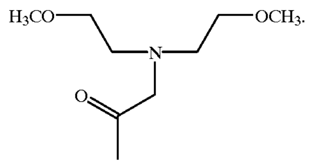

67. The PNA oligomer of claim 61, wherein the PNA comprises one or more achiral linked modifying moieties having the formula:

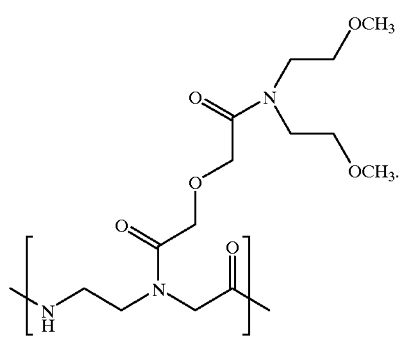

68. The PNA oligomer of claim 61, wherein the PNA comprises one or more achiral linked modifying moieties having the formula:

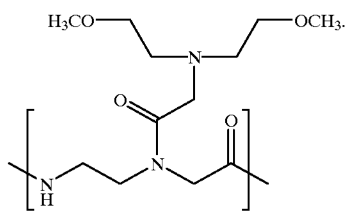

69. The PNA oligomer of claim 61, wherein the PNA has been purified such that it is greater than 80 percent pure.

70. The PNA oligomer of claim 61, wherein the PNA comprises one or more hydrophobic labels.

71. A purine-rich PNA oligomer comprising a hydrophobic label.

72. The PNA oligomer of claim 71, wherein the PNA comprises 6 or more sequential purine residues.

73. The PNA oligomer of claim 71, wherein the PNA is a homopurine polymer.

74. The PNA oligomer of claim 71, wherein the PNA comprises four or more sequential guanine containing subunits.

75. The PNA oligomer of claim 71, wherein the PNA comprises one or more linked achiral modifying moieties having the formula:

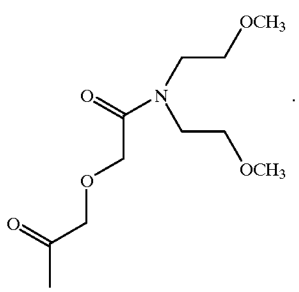

76. The PNA oligomer of claim 71, wherein the PNA comprises one or more linked achiral modifying moieties having the formula:

$H_3CO$ — N — $OCH_3$.

77. The PNA oligomer of claim 71, wherein the PNA comprises one or more linked achiral modifying moieties havng the formula:

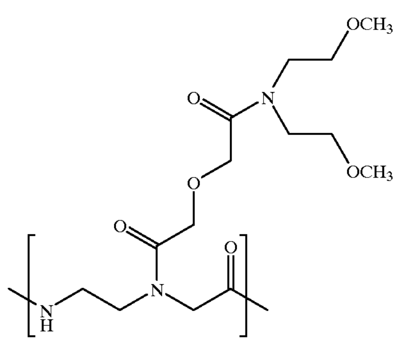

78. The PNA oligomer of claim 71, wherein the PNA comprises one or more linked achiral modifying moieties havng the formula:

$H_3CO$ — N — $OCH_3$.

79. A purine-rich PNA oligomer not having a linked chiral amino acid moiety.

80. The PNA oligomer of claim 79, wherein the PNA comprises 6 or more sequential purine residues.

81. The PNA oligomer of claim 79, wherein the PNA is a homopurine polymer.

82. The PNA oligomer of claim 79, wherein the PNA comprises four or more sequential guanine containing subunits.

83. The PNA oligomer of claim 79, wherein the PNA comprises one or more linked achiral modifying moieties having the formula:

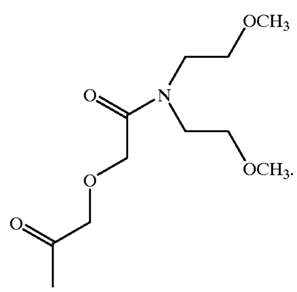

84. The PNA oligomer of claim 79, wherein the PNA comprises one or more linked achiral modifying moieties having the formula:

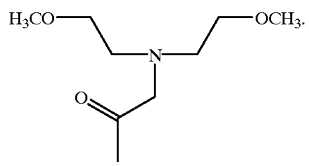

85. The PNA oligomer of claim 79, wherein the PNA comprises one or more linked achiral modifying moieties having the formula:

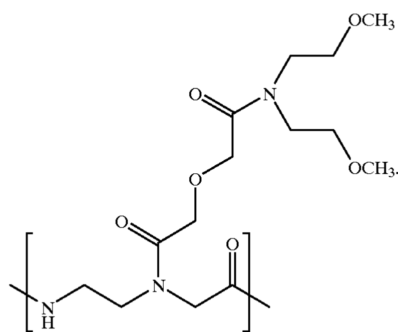

86. The PNA oligomer of claim 79, wherein the PNA comprises one or more linked achiral modifying moieties having the formula:

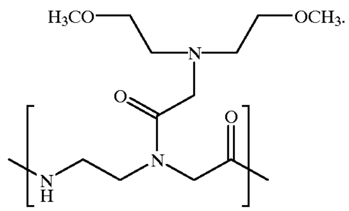

87. The PNA oligomer of claim 79, wherein the PNA has been purified such that it is greater than 80 percent pure.

88. The PNA oligomer of claim 71, wherein the PNA has been purified such that it is greater than 80 percent pure.

89. A PNA oligomer comprising one or more achiral, neutral and non-nucleophilic modifying moieties linked to the polymer at a position adjacent to the nucleobase containing subunits.

90. The PNA oligomer of claim 89, wherein the one or more achiral, neutral and non-nucleophilic modiying moieties have the formula:

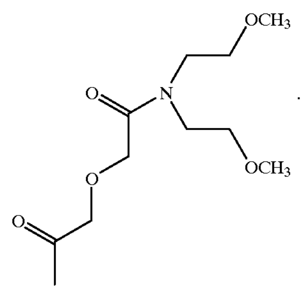

91. The PNA oligomer of claim 89, wherein the one or more achiral, neutral and non-nucleophilic modifying moieties have the formula:

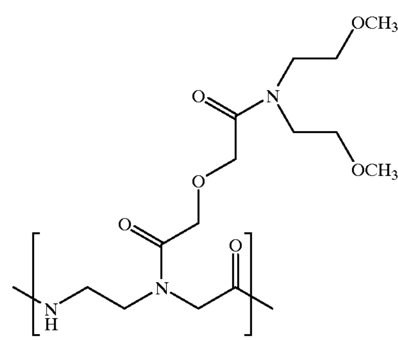

92. A PNA oligomer comprising one or more achiral, positively charged, non-nucleophilic modifying moieties linked to the polymer at a position adjacent to the nucleobase containing subunits.

93. The PNA oligomer of claim 92, wherein the one or more achiral, positively charged, non-nucleophilic modifying moieties have the formula:

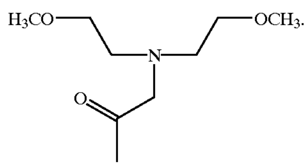

94. The PNA oligomer of claim 92, wherein the one or more achiral, positively charged, non-nucleophilic modifying moieties have the formula:

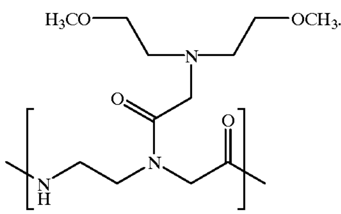

* * * * *

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence -continued

```
<220> FEATURE:
<223> OTHER INFORMATION: Description of Artificial Sequence: SYNTHETIC
      OLIGONUCLEOTIDE WHICH IS COMPLEMENTARY TO PNA;
      USED FOR Tm ANALYSIS

<400> SEQUENCE: 1

tcctacggga ggcag                                                    15
```